US007820883B2

(12) United States Patent
Walsh et al.

(10) Patent No.: US 7,820,883 B2
(45) Date of Patent: Oct. 26, 2010

(54) RESISTANCE TO AUXINIC HERBICIDES

(75) Inventors: Terence A. Walsh, Zionsville, IN (US); Glenn Hicks, Riverside, CA (US); Mary Honma, San Francisco, CA (US); John P. Davies, Portland, OR (US)

(73) Assignee: Dow AgroSciences LLC, Indianapolis, IN (US)

( * ) Notice: Subject to any disclaimer, the term of this patent is extended or adjusted under 35 U.S.C. 154(b) by 713 days.

(21) Appl. No.: 11/686,844

(22) Filed: Mar. 15, 2007

(65) Prior Publication Data

US 2007/0220629 A1 Sep. 20, 2007

Related U.S. Application Data

(60) Provisional application No. 60/783,015, filed on Mar. 15, 2006.

(51) Int. Cl.
*A01H 1/00* (2006.01)
*A01H 5/00* (2006.01)
*C12N 15/82* (2006.01)

(52) U.S. Cl. .............. 800/300; 800/278; 800/285; 800/286; 800/295; 800/298; 800/306; 800/312; 800/314; 800/317.3; 800/320; 800/320.2; 800/322; 435/410; 435/414; 435/415; 435/416; 435/418

(58) Field of Classification Search .............. None
See application file for complete search history.

(56) References Cited

U.S. PATENT DOCUMENTS

| | | | |
|---|---|---|---|
| 4,810,648 A | 3/1989 | Stalker et al. | |
| 4,987,071 A | 1/1991 | Cech et al. | |
| 5,094,945 A | 3/1992 | Comai | |
| 5,322,783 A | 6/1994 | Tomes et al. | |
| 5,378,619 A | 1/1995 | Rogers | |
| 5,459,255 A | 10/1995 | Cook et al. | |
| 5,538,880 A | 7/1996 | Lundquist et al. | |
| 5,539,083 A | 7/1996 | Cook et al. | |
| 5,543,508 A | 8/1996 | Haseloff et al. | |
| 5,550,318 A | 8/1996 | Adams et al. | |
| 5,563,055 A | 10/1996 | Townsend et al. | |
| 5,587,469 A | 12/1996 | Cook et al. | |
| 5,599,797 A | 2/1997 | Cook et al. | |
| 5,610,042 A | 3/1997 | Chang et al. | |
| 5,610,289 A | 3/1997 | Cook et al. | |
| 5,623,070 A | 4/1997 | Cook et al. | |
| 5,627,061 A | 5/1997 | Barry et al. | |
| 5,629,152 A | 5/1997 | Ravikumar | |
| 5,633,435 A | 5/1997 | Barry et al. | |
| 5,635,488 A | 6/1997 | Cook et al. | |
| 5,661,134 A | 8/1997 | Cook et al. | |
| 5,783,393 A | 7/1998 | Kellogg et al. | |
| 5,783,394 A | 7/1998 | Bestwick et al. | |
| 5,859,330 A | 1/1999 | Bestwick et al. | |
| 6,040,497 A | 3/2000 | Spencer et al. | |

2005/0108791 A1* 5/2005 Edgerton .............. 800/284

FOREIGN PATENT DOCUMENTS

| | | |
|---|---|---|
| WO | WO 84/02913 | 8/1994 |
| WO | WO 95/06128 | 3/1995 |
| WO | WO 97/10328 | 3/1997 |
| WO | WO 00/56863 | 9/2000 |
| WO | WO 03/011853 | 2/2003 |

OTHER PUBLICATIONS

AtABF5Blast.pdf.*
AtAFB4BLAST.pdf.*
ATNO.2andRICENO.8Blast.pdf.*
ATNO.2andRICENO.10Blast.pdf.*
Alonso et al., "Five components of the ethylene-response pathway identified in a screen for weak ethylene-insensitive mutants in Arabidopsis," *Proc Natl Acad Sci USA* 100 (5): 2992-2997, 2003.
Aufsatz et al., "RNA-directed DNA methylation in *Arabidopsis*," *Proc. Natl. Acad. Sci. U.S.A.* 99: 16499-16506, 2002.
Baldwin et al., "A comparison of gel-based, nylon filter and microarray techniques to detect differential RNA expression in plants," *Curr Opin Plant Biol.* 2(2): 96-103, 1999.
Baulcombe DC, "Fast forward genetics based on virus-induced gene silencing," *Current Opinion in Plant Biology* 2: 109-113, 1999.
Bert et al., "Comparative genetic analysis of quantitative traits in sunflower (*Helianthus annuus* L.). 2. Characterisation of QTL involved in developmental and agronomic traits," *Theor Appl Genet.* 107(1):181-189, 2003.
Block, et al., "Engineering herbicide resistance in plants by expression of a detoxifying enzyme." *EMBO J.* 6: 2513-2519, 1987.
Cannon et al., "Organ-specific modulation of gene expression in transgenic plants using antisense RNA," *Plant Mol Biol* 15: 39-47, 1990.
Chandler et al., "Two regulatory genes of the maize anthocyanin pathway are homologous: isolation of B utilizing R genomic sequences," *The Plant Cell* 1: 1175-1183, 1989.

(Continued)

*Primary Examiner*—Eileen B O Hara
(74) *Attorney, Agent, or Firm*—Donald R. Stuart; Klarquist Sparkman LLP; Eric J. Kraus

(57) ABSTRACT

The invention provides methods of identifying herbicidal auxins. The invention further provides auxin-herbicide-resistant plants and genes conferring auxin-herbicide resistance. This invention also provides a method of identifying other proteins that bind picolinate auxins from additional plant species. The invention further provides a method to identify the molecular binding site for picolinate auxins. The invention also includes the use of the picolinate herbicidal auxin target site proteins, and methods of discovering new compounds with herbicidal or plant growth regulatory activity. The invention also includes methods for producing plants that are resistant to picolinate herbicidal auxins. Specific examples of novel proteins associated with herbicide binding include AFB5, AFB4, and SGT1b.

17 Claims, 8 Drawing Sheets

OTHER PUBLICATIONS

Christou et al., "Inheritance and expression of foreign genes in transgenic soybean plants," *Proc Natl Acad Sci USA* 86: 7500-7504, 1989.

Chu et al., "Establishment of an Efficient Medium for Anther Culture of Rice Through Comparative Experiments on the Nitrogen Sources," *Scientia Sinica* 18: 659, 1975.

Colbert et al., "High-throughput screening for induced point mutations," *Plant Physiol* 126: 480-484, 2001.

De Block et al., "Transformation of *Brassica napus* and *Brassica oleracea* using *Agrobacterium tumefaciens* and the expression of the bar and neo genes in the transgenic plants," *Plant Physiol* 91: 694-701, 1989.

Dharmasiri et al., "Auxin action in a cell-free system," *Current biology* 13: 1418-1422, 2003.

Dharmasiri et al., "The F-box protein TIR1 is an auxin receptor," *Nature* 435: 441-445, 2005.

Dharmasiri et al., "Plant development is regulated by a family of auxin receptor F box proteins," *Developmental Cell* 9: 109-119, 2005.

Ebert et al., "Identification of an essential upstream element in the nopaline synthase promoter by stable and transient assays," *Proc. Natl. Acad. Sci. USA* 84: 5745-5749, 1987.

Eckhardt, "RNA Goes Mobile," *Plant Cell*, 14: 1433-1436, 2002.

Estelle and Somerville, "Auxin-resistant mutants of *Arabidopsis thaliana* with an altered morphology," *Mol Gen Genet* 206: 200-206, 1987.

Everett et al., "Genetic engineering of sunflower (*Helianthus annuus* L.)," *Bio/Technology* 5: 1201-1204, 1987.

Gagne et al., "The F-box subunit of the SCF E3 complex is encoded by a diverse superfamily of genes in *Arabidopsis*," *Proc Natl Acad Sci USA* 99: 11519-11524, 2002.

Gray et al., "Identification of an SCF ubiquitin-ligase complex required for auxin response in *Arabidopsis thaliana*," *Genes and Dev.* 13: 1678-1691, 1999.

Gray et al., "Auxin regulates $SCF^{TIR1}$-dependent degradation of AUX/IAA proteins," *Nature* 414: 271-276, 2001.

Gray et al., "*Arabidopsis* SGT1b is required for $SCF^{TIR1}$-mediated auxin response," *Plant Cell* 15: 1310-1319, 2003.

Jones et al., "Effective vectors for transformation, expression of heterologous genes and ASSAYING transposon excision in transgenic plants," *Transgenic Res.* 1: 285-97, 1992.

Kepinski and Leyser, "The *Arabidopsis* F-box protein TIR1 is an auxin receptor," *Nature* 435: 446-451, 2005.

Kumar et al., "MEGA3: Integrated software for Molecular Evolutionary Genetics Analysis and sequence alignment," *Briefings in Bioinformatics* 5: 150-163, 2004.

Lawton et al., "Expression of a soybean β-conclycinin gene under the control of the Cauliflower Mosaic Virus 35S and 19S promoters in transformed petunia tissues," *Plant Mol. Biol.* 9: 315-324, 1987.

Leyser et al., "*Arabidopsis* auxin-resistance gene AXR1 encodes a protein related to ubiquitin-activating enzyme E1," *Nature* 364: 161-164, 1993.

Lionneton et al., "Development of an AFLP-based linkage map and localization of QTLs for seed fatty acid content in condiment mustard (*Brassica juncea*)," *Genome* 45(6): 1203-1215, 2002.

McCallum et al., "Targeted screening for induced mutations," *Nature Biotechnology* 18: 455-457, 2000.

Nagpal et al., "AXR2 encodes a member of the Aux/IAA protein family," *Plant Physiol* 123: 563-573, 2000.

Nakamura et al., "Codon usage tabulated from the international DNA sequence databases; its status 1999," *Nucleic Acids Research* 27: 292, 1999.

Napoli et al., "Introduction of a chimeric chalcone synthase gene into petunia results in reversible co-suppression of homologous genes in trans," *Plant Cell* 2: 279-289, 1990.

Odell et al., "Identification of DNA sequences required for activity of the cauliflower MOSAIC virus 35S promoter," *Nature* 313: 810-812, 1985.

Pontier et al., "Trans-dominant suppression of plant TGA factors reveals their negative and positive roles in plant defense responses," *Plant J.* 27: 529-538, 2001.

Que et al., "The Frequency and Degree of Cosuppression by Sense Chalcone Synthase Transgenes Are Dependent on Transgene Promoter Strength and Are Reduced by Premature Nonsense Codons in the Transgene Coding Sequence," *Plant Cell* 9: 1357-1368, 1997.

Richmond & Somerville, "Chasing the dream: plant EST microarrays," *Curr Opin Plant Biol* 3: 108-116, 2000.

Risseeuw et al., "Protein interaction analysis of SCF ubiquitin E3 ligase subunits from *Arabidopsis*," *Plant Journal* 34: 753-767, 2003.

Ruegger et al., "The TIR1 protein of *Arabidopsis* functions in auxin response and is related to human SKP2 and yeast Grr1p," *Genes Dev* 12: 198-207, 1998.

Sathasivian et al., "Nucleotide sequence of a mutant acetolactate synthase gene from an imidazolinone-resistant *Arabidopsis thaliana* var. Columbia," *Nucl. Acids Res.* 18: 2188-2193, 1990.

Schwechheimer et al., "Multiple ubiquitin ligase-mediated processes require COP9 signalosome and AXR1 function," *Plant Cell* 14(10): 2553-2563, 2002.

Sheehy et al., "Reduction of polygalacturonase activity in tomato fruit by antisense RNA," *Proc Natl Acad Sci USA* 85: 8805-8809, 1988.

Smith et al., "Antisense RNA inhibition of polygalacturonase gene expression in transgenic tomatoes," *Nature* 334: 724-726, 1988.

Smith et al., "Expression of a truncated tomato polygalacturonase gene inhibits expression of the endogenous gene in transgenic plants," *Mol Gen Genet* 224: 477-481, 1990.

Tor et al., "*Arabidopsis* SGT1b is required for defense signaling conferred by several downy mildew resistance genes," *Plant Cell* 14: 993-1003, 2002.

Van Der Krol et al., "Modulation of eukaryotic gene expression by complementary RNA or DNA sequences," *BioTechniques* 6: 958-976, 1988.

Van Der Krol et al., "Flavonoid genes in petunia: addition of a limited number of gene copies may lead to a suppression of gene expression," *Plant Cell* 2: 291-299, 1990.

Van Hal et al., "The application of DNA microarrays in gene expression analysis," *J Biotechnol* 78: 271-280, 2000.

Walker et al., "DNA sequences required for anaerobic expression of the maize alcohol dehydrogenase 1 gene," *Proc. Natl. Acad. Sci. USA* 84: 6624-6628, 1987.

Waterhouse et al., "Virus resistance and gene silencing in plants can be induced by simultaneous expression of sense and antisense RNA," *Proc Natl Acad Sci USA* 95: 13959-13964, 1998.

Wilson et al., "A dominant mutation in *Arabidopsis* confers resistance to auxin, ethylene and abscisic acid," *Mol Gen Genet* 222: 377-383, 1990.

Yang et al., "Maize sucrose synthase-1 promoter directs phloem cell-specific expression of Gus gene in transgenic tobacco plants," *Proc. Natl. Acad. Sci. USA* 87: 4144-4148, 1990.

Zheng et al., "Structure of the Cul1-Rbx1-Skp1-F boxSkp2 SCF ubiquitin ligase complex," *Nature* 416: 703-709, 2002.

\* cited by examiner

FIG. 4

RESISTANCE TO AUXINIC HERBICIDES

REFERENCE TO RELATED APPLICATION(S)

This application claims the benefit of U.S. Provisional application No. 60/783,015, filed Mar. 15, 2006, which is incorporated herein in its entirety.

FIELD OF THE DISCLOSURE

The present invention relates to the field of plant biology and specifically to methods of identifying herbicidal auxins and herbicide resistant plants, and to nucleotide sequences conferring herbicide resistance to plants, particularly resistance to picolinate class of auxinic herbicides.

BACKGROUND OF THE DISCLOSURE

The use of herbicides for weed control is an extremely valuable agricultural practice to protect the yield of crop plants and to manage the growth of vegetation in pastures and other sites. However the use of many herbicides is becoming problematic through the advent of field resistance and also from increased toxicological and environmental concerns associated with certain pesticidal chemistries and modes of action. Thus there is a continuing need for new herbicidal chemistries.

There are currently a limited number of herbicidal classes that have proven to exhibit the desired attributes for a beneficial modern herbicide such as low incidence of resistance development and low potential for toxicological side effects. One such class is the auxinic herbicides that include such compounds as 2,4-D and picloram. This class can be further subdivided into compounds that contain a picolinate moiety (e.g., picloram, aminopyralid, clopyralid), those that contain an aryloxyacetate moiety (e.g., 2,4-D, fluroxypyr, triclopyr etc.) and others (e.g., dicamba). All of these compounds elicit plant symptoms similar to excessive treatment with the natural plant hormone indole acetic acid (IAA) and induce similar physiological events, eventually leading to plant death. Interestingly, the widespread use of auxinic herbicides for many years has not resulted in significant field resistance. In addition, the auxinic mode of action is specific to plants and many of the auxinic herbicides exhibit favorable environmental profiles. Thus methods for the discovery of new compounds that act via the auxinic mode of action would be of great benefit, particularly those with increased potency, wider spectrum, optimal soil persistency or low cost of manufacture.

Genes that confer resistance to certain herbicides have found utility in the development of herbicide-tolerant crops by transgenic or mutagenic selection methods. Many auxinic herbicides have broad spectrum herbicidal activity but their use is limited by the fact that the desired crop or pasture component species is sensitive to the herbicide. This is particularly the case for the picolinate class of auxinic herbicides. Thus there is an unfulfilled need for herbicide-tolerance mechanisms that would be applicable to the picolinate class of auxinic herbicides.

SUMMARY OF THE DISCLOSURE

The invention in various embodiments provides methods of identifying herbicidal auxins (reporter assays, co-crystal structures of picolinate auxins and other chemistries that interact with AFB4, AFB5 or SGT1b. Also provided are auxin herbicide resistant plants and genes conferring auxin-herbicide resistance. This disclosure also provides a method of identifying other proteins that bind picolinate auxins from additional plant species. These proteins may be identified by sequence similarity with AFB5 or SGT1b, the picolinate auxin target proteins disclosed here.

The invention in various embodiments further provides a method to identify the molecular binding site for picolinate auxins on AFB4 and AFB5 by performing domain swap experiments between AFB5 and the closely related F-box protein TIR1. Both AFB5 and TIR1 participate in auxin signal transduction; however TIR1 does not significantly interact with certain picolinate auxins. The binding site for the picolinate auxins may be identified by combining different portions of AFB5 and TIR1 and assaying for picolinate auxin binding to the chimeric protein.

As discussed in more detail below, AFB4 is another AFB protein of the subject invention. AFB4 shares about 80% amino acid identity with AFB5. AFB4 and AFB5 homologs are distinct in various ways (at the sequence level and in light of their unique properties, for example) from TIR1 and previously known AFB proteins such as AFB1, AFB2, and AFB3. AFB1 is about 45% identical to AFB4 and about 47% identical to AFB5. AFB3 is about 48% identical to AFB4 and about 49% identical to AFB5.

The disclosure also includes the use of the picolinate herbicidal auxin target site proteins in discovering new compounds with herbicidal or plant growth regulatory activity. In one embodiment, the proteins can be used in biochemical assays to identify compounds that effectively inhibit ligand-binding to the target protein or inhibit auxin functionality. In another embodiment the proteins may be crystallized in the presence or absence of the herbicide and the molecular structure of the proteins determined by X-ray crystallography. This structural information can be used to design or search for new chemical structures that effectively interact with the target protein.

The disclosure also includes methods for producing plants that are resistant to picolinate herbicidal auxins. This may be accomplished through the generation of transgenic plants with gene constructs that inhibit the expression of the target protein or by screening for plants that are resistant to the picolinate auxin and using molecular information about the gene encoding the target protein to identify the mutation responsible for the auxin resistance or in plant breeding experiments that may enable the movement of the resistance gene into other plant varieties.

Picolinate auxinic herbicides exert their herbicidal effects through specific interaction with certain proteins and these proteins do not interact significantly with other auxinic herbicides, such as 2,4-D. One such protein is AFB5. AFB5 shows sequence similarity to a reported auxin receptor, the F-box protein, TIR1, that has been shown to mediate the interaction of the natural hormone IAA (and the herbicide 2,4-D) to initiate the auxin signal transduction cascade (Dharmasiri et al., Nature 435:441-445, 2005; Kepinski and Leyser, Nature 435:446-451, 2005). TIR1 acts as the recognition component of an SCF E3-ubiquitin ligase complex that directs the proteosomal degradation of auxin-responsive transcriptional regulators. The advantage of the present invention is that AFB5 specifically mediates the interaction of picolinate herbicidal auxins and not IAA or 2,4-D such that loss of its function confers resistance to picolinate auxins specifically and stimulation of its function leads to a herbicidal signal cascade. Another protein discovered to have similar properties is SGT1b. This is also associated with SCF function and is involved in mediating protein-protein interactions.

A feature of this invention is that SGT1b function is specifically involved in picolinate auxin action.

The foregoing and other features and advantages will become more apparent from the following detailed description of several embodiments, which proceeds with reference to the accompanying figures.

BRIEF DESCRIPTION OF THE FIGURES

(FIG. 1A) DAS534, (FIG. 1B) 2,4-D, (FIG. 1C) picloram, (FIG. 1D) IAA.

(FIG. 2A) to (FIG. 2E) untreated seedlings, (FIG. 2F) to (FIG. 2J) seedlings grown in the presence of 5 nM DAS534. The primary visible effects at this sublethal concentration of auxin are loss of gravitropism, lack of cotyledon decurvature and increased hypocotyl elongation (FIG. 2F). Mutants R127 and R051 are resistant to this effect (FIG. 2G) and (FIG. 2I), whereas mutants transformed with the corresponding wild-type gene regain the response, (FIG. 2H) and (FIG. 2J). The R127 CsVMV:AFB5 line appears to have an increased response relative to Col-0 (FIG. 2H).

(FIG. 3A) mapping of R009, (FIG. 3B) mapping of R051.

FIG. 4. Comparison of the amino acid sequences of six TIR1-related F-box proteins from *Arabidopsis* and COI1. Sequences were aligned using CLUSTAL within the Vector NTI suite. The F-box domain is denoted by the hatched line and the N-terminal extension unique to AFB5 and AFB4 by the solid line. Identical residues in all five AFBs are shaded black, residues that have conservative substitutions in one or more AFBs are shaded gray. The sites of the three mutant alleles of AFB5 are shown in italics, and those previously described for TIR1 are shown with underlining (Ruegger et al., Genes Dev 12: 198-207, 1998; Alonso et al., Proc Natl Acad Sci USA. 100(5):2992-2997, 2003). AFB1 is gi|18412177, AFB2 is gi|18405102, AFB3 is gi|18391439, AFB4 is gi|42573021, AFB5 is gi|18423092, TIR1 is gi|18412567 and COI1 is gi|8405209.

(FIG. 5A) Effect of DAS534 on edm1 and R051. The deletion mutant line edm1 lacks seven genes (At4g11220 through At4g11280) including SGT1b (Tor et al., Plant Cell 14: 993-1003, 2002). Effect of DAS534 (FIG. 5B) and 2,4-D (FIG. 5C) on axr1-3, axr2-1 and tir1-1 compared with R009 and R051.

(FIG. 6A) The exons of SGT1b are shown as boxed regions. The mutations in R107, R051 and R118 occur at the 3' splicing sites of introns 6 and 7 of the gene. (FIG. 6B) The nucleotide sequences of the 3' intron-exon boundaries for introns 6 and exon 7 and for intron 7 and exon 8 are shown. The intron portion is shaded gray and the mutation sites are arrowed. The complete nucleotide sequences of At4g11260 can be found in gi|30698542 as the complement of sequences 6851273 through 6853848.

BRIEF DESCRIPTION OF THE SEQUENCES

Figure 1:
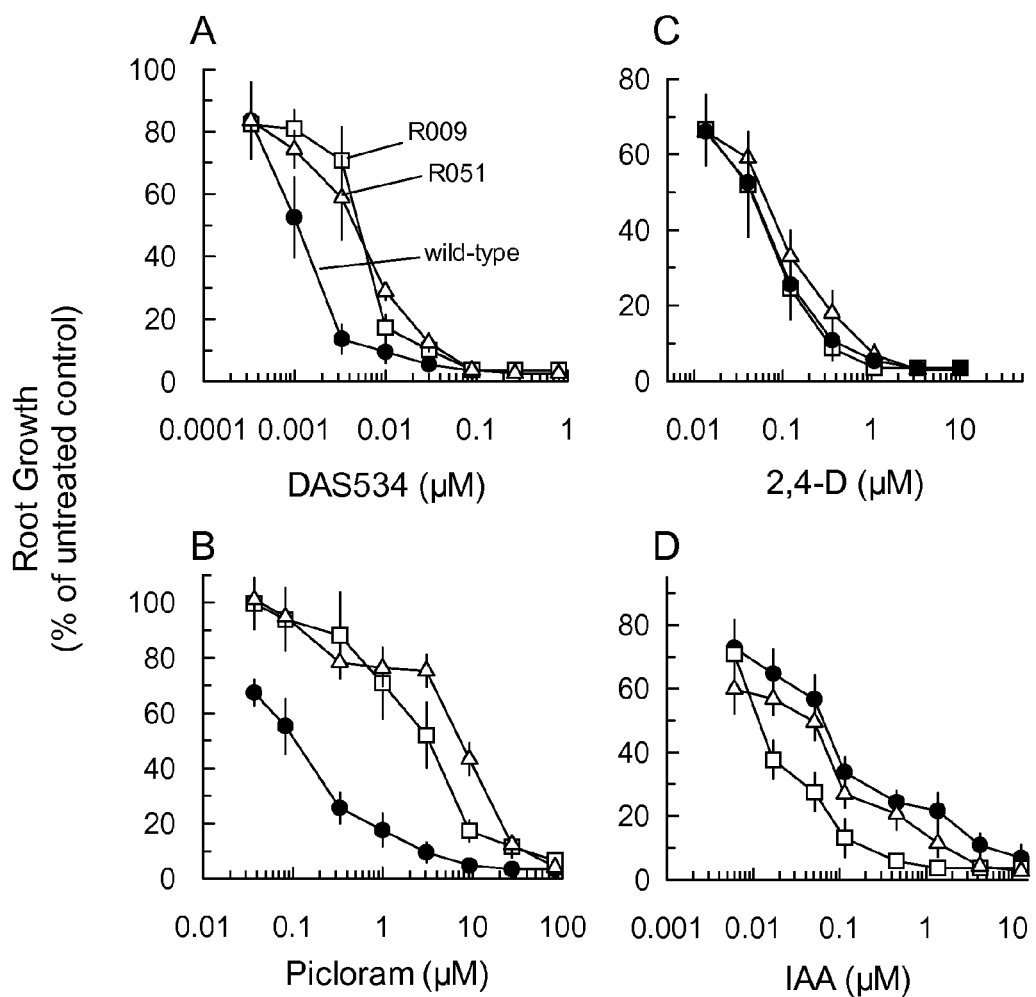
FIGS. 1A-1D. Differential effects of auxins on root growth of mutants from complementation Groups 1 and 2. Root lengths of *Arabidopsis* seedlings were measured 8 days after seeding on plates containing a range of concentrations of the test compounds and are plotted as a percentage of the root length of untreated plants in the same experiment. Typical root lengths for untreated controls were 21, 21 and 24 mm for wild-type, Group 1, and Group 2 plants respectively. The symbols used for wild type, R009 from complementation Group 1 and R051 from complementation Group 2 are denoted in FIG. 1A.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand.

In the accompanying sequence listing:

SEQ ID NO: 1 provides the nucleic acid sequence for the *Arabidopsis* gene identified herein as AFB5 and being a picolinate auxin receptor and associated with resistance to this class of herbicides (gi|30695799: 135-1994 *Arabidopsis thaliana* transport inhibitor response protein, putative (At5g49980) mRNA, complete cds).

SEQ ID NO: 2 provides the AFB5 protein sequence encoded by SEQ ID NO: 1 (gi|18423092|ref|NP_568718.1| transport inhibitor response protein, putative [*Arabidopsis thaliana*]).

SEQ ID NO: 3 provides the nucleic acid sequence for the *Arabidopsis* gene identified herein as SGT1b and being associated with picolinate auxin binding and resistance (gi|17017309|gb|AF439976.1| *Arabidopsis thaliana* SGT1b (SGT1b) mRNA, complete cds).

SEQ ID NO: 4 provides the SGT1b protein sequence encoded by SEQ ID NO: 3 (gi|17017310|gb|AAL33612.1|AF439976_1 SGT1b [*Arabidopsis thaliana*]).

SEQ ID NO: 5 provides the nucleic acid sequence for the *Arabidopsis* gene identified herein as AFB4 (gi|42573020|ref|NM_202878.1| *Arabidopsis thaliana* ubiquitin-protein ligase AT4G24390 transcript variant AT4G24390.2 mRNA, complete cds).

SEQ ID NO: 6 provides the AFB4 protein sequence encoded by SEQ ID NO: 5 (gi|42573021|ref|NP_974607.1| ubiquitin-protein ligase [*Arabidopsis thaliana*]).

SEQ ID NO: 7 provides the nucleic acid sequence of an AFB5 homolog from *Oryza sativa* (rice) (GenBank entry gi:34902411). (gi|34902411|ref|NM_187663.1| *Oryza sativa* (japonica cultivar-group), predicted mRNA).

SEQ ID NO: 8 provides the protein sequence encoded by SEQ ID NO: 7. (gi|34902412|ref|NP_912552.1| Putative F-box containing protein TIR1 [*Oryza sativa* (japonica cultivar-group)]).

SEQ ID NO: 9 provides the nucleic acid sequence of another AFB5 homolog from *Oryza sativa* (rice) (GenBank entry gi:51979369). (gi|51979369|ref|XM_507533.1| PREDICTED *Oryza sativa* (japonica cultivar-group), OJ1175_B01.8-1 mRNA).

SEQ ID NO: 10 provides the protein sequence encoded by SEQ ID NO: 9. (gi|51979370|ref|XP_507533.1| PREDICTED OJ1175_B01.8-1 gene product [*Oryza sativa* (japonica cultivar-group)]).

SEQ ID NO: 11 provides the nucleic acid sequence of an AFB5 homolog from Populus (gi|13249029|gb|AF139835.1|AF139835 *Populus tremula×Populus tremuloides* F-box containing protein TIR1 (TIR1) mRNA, complete cds).

SEQ ID NO: 12 provides the protein sequence encoded by SEQ ID NO: 11 (gi|13249030|gb|AAK16647.1|AF139835_1 F-box containing protein TIR1 [*Populus tremula×Populus tremuloides*]).

SEQ ID NO: 13 provides the amino acid sequence of the myc epitope.

DETAILED DESCRIPTION OF THE INVENTION

Terms.

Unless otherwise indicated, all technical and scientific terms used herein have the same meaning as they would to one skilled in the art of the present invention. Practitioners are particularly directed to Sambrook et al. (Molecular Cloning, Cold Spring Harbor, 1989) and Ausubel et al., (Current Protocols in Molecular Biology, 1993), for definitions and terms of the art. It is to be understood that this invention is not limited to the particular methodology, protocols, and reagents described, as these may vary.

In order to facilitate review of the various embodiments of the invention, the following explanations of specific terms are provided:

As used herein, the term "herbicide" refers to a chemical compound employed to kill or suppress the growth of plants, plant cells and tissues or to prevent or suppress the germination and growth of plant seeds.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

A "heterologous" nucleic acid construct or sequence has a portion of the sequence that is not native to the plant cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, microinjection, electroporation, or the like. A "heterologous" nucleic acid construct may contain a control sequence/DNA coding sequence combination that is the same as, or different from a control sequence/DNA coding sequence combination found in the native plant.

As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons) and non-transcribed regulatory sequence.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

As used herein, the term "gene expression" refers to the process by which a polypeptide is produced based on the nucleic acid sequence of a gene. The process includes both transcription and translation; accordingly, "expression" may refer to either a polynucleotide or polypeptide sequence, or both. Sometimes, expression of a polynucleotide sequence will not lead to protein translation. "Over-expression" refers to increased expression of a polynucleotide and/or polypeptide sequence relative to its expression in a wild-type (or other reference [e.g., non-transgenic]) plant and may relate to a naturally-occurring or non-naturally occurring sequence. "Ectopic expression" refers to expression at a time, place, and/or increased level that does not naturally occur in the non-altered or wild-type plant. "Under-expression" refers to decreased expression of a polynucleotide and/or polypeptide sequence, generally of an endogenous gene, relative to its expression in a wild-type plant. The terms "mis-expression" and "altered expression" encompass over-expression, under-expression, and ectopic expression.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, a "plant cell" refers to any cell derived from a plant, including cells from undifferentiated tissue (e.g., callus) as well as plant seeds, pollen, propagules and embryos. As used herein, the terms "native" and "wild-type" relative to a given plant trait or phenotype refers to the form in which that trait or phenotype is found in the same variety of plant in nature.

As used herein, the term "modified" regarding a plant trait, refers to a change in the phenotype of a transgenic plant relative to the similar non-transgenic plant. An "interesting phenotype (trait)" with reference to a transgenic plant refers to an observable or measurable phenotype demonstrated by a T1 and/or subsequent generation plant, which is not displayed by the corresponding non-transgenic (i.e., a genotypically similar plant that has been raised or assayed under similar conditions). An interesting phenotype may represent an improvement in the plant or may provide a means to produce improvements in other plants. An "improvement" is a feature that may enhance the utility of a plant species or variety by providing the plant with a unique and/or novel quality.

As used herein, a "mutant" polynucleotide sequence or gene differs from the corresponding wild type polynucleotide sequence or gene either in terms of sequence or expression, where the difference contributes to a modified plant phenotype or trait. Relative to a plant or plant line, the term "mutant" refers to a plant or plant line which has a modified plant phenotype or trait, where the modified phenotype or trait is associated with the modified expression of a wild type polynucleotide sequence or gene.

As used herein, the term "T1" refers to the generation of plants from the seed of T0 plants. The T1 generation is the first set of transformed plants that can be selected by application of a selection agent, e.g., an antibiotic or herbicide, for which the transgenic plant contains the corresponding resistance gene. The term "T2" refers to the generation of plants by self-fertilization of the flowers of T1 plants, previously selected as being transgenic. T3 plants are generated from T2 plants, etc. As used herein, the "direct progeny" of a given plant derives from the seed (or, sometimes, other tissue) of that plant and is in the immediately subsequent generation; for instance, for a given lineage, a T2 plant is the direct progeny of a T1 plant. The "indirect progeny" of a given plant derives from the seed (or other tissue) of the direct progeny of that plant, or from the seed (or other tissue) of subsequent generations in that lineage; for instance, a T3 plant is the indirect progeny of a T1 plant.

As used herein, the term "plant part" includes any plant organ or tissue, including, without limitation, seeds, embryos, meristematic regions, callus tissue, leaves, roots, shoots, gametophytes, sporophytes, pollen, and microspores. Plant cells can be obtained from any plant organ or tissue and cultures prepared therefrom. The class of plants which can be used in the methods of the present invention is generally as broad as the class of higher plants amenable to transformation techniques, including both monocotyledenous and dicotyledenous angiosperm as well as gymnosperm plants.

As used herein, the term "gene silencing" refers to lack of (or reduction of) gene expression as a result of, though not limited to, effects at a genomic (DNA) level such as chromatin re-structuring, or at the post-transcriptional level through effects on transcript stability or translation. Evidence suggests that RNA interference (RNAi) is a major process involved in transcriptional and posttranscriptional gene silencing. Because RNAi exerts its effects at the transcriptional and/or post-transcriptional level, it is believed that RNAi can be used to specifically inhibit alternative transcripts from the same gene.

As used herein, the terms "interfering with" or "inhibiting" (expression of a target sequence) refers to the ability of a small RNA, such as an siRNA or a miRNA, or other molecule, to measurably reduce the expression and/or stability of molecules carrying the target sequence. A target sequence can include a DNA sequence, such as a gene or the promoter region of a gene, or an RNA sequence, such as an mRNA. "Interfering with or inhibiting" expression contemplates reduction of the end-product of the gene or sequence, e.g., the expression or function of the encoded protein or a protein, nucleic acid, other biomolecule, or biological function influenced by the target sequence, and thus includes reduction in the amount or longevity of the mRNA transcript or other target sequence. In some embodiments, the small RNA or other molecule guides chromatin modifications which inhibit the expression of a target sequence. It is understood that the phrase is relative, and does not require absolute inhibition (suppression) of the sequence. Thus, in certain embodiments, interfering with or inhibiting expression of a target sequence requires that, following application of the small RNA or other molecule (such as a vector or other construct encoding one or more small RNAs), the sequence is expressed at least 5% less than prior to application, at least 10% less, at least 15% less, at least 20% less, at least 25% less, or even more reduced. Thus, in some particular embodiments, application of a small RNA or other molecule reduces expression of the target sequence by about 30%, about 40%, about 50%, about 60%, or more. In specific examples, where the small RNA or other molecule is particularly effective, expression is reduced by 70%, 80%, 85%, 90%, 95%, or even more.

As used herein, the term "Post-Transcriptional Gene Silencing" (PTGS) refers to a form of gene silencing in which the inhibitory mechanism occurs after transcription. This can result in either decreased steady-state level of a specific RNA target or inhibition of translation (Tusch1, ChemBiochem, 2:239-245, 2001). In the literature, the terms RNA interference (RNAi) and posttranscriptional cosuppression are often used to indicate posttranscriptional gene silencing.

As used herein, the term "regulating gene expression" refers to the process of controlling the expression of a gene by increasing or decreasing the expression, production, or activity of an agent that affects gene expression. The agent can be a protein, such as a transcription factor, or a nucleic acid molecule, such as a miRNA or an siRNA molecule, which when in contact with the gene or its upstream regulatory sequences, or a mRNA encoded by the gene, either increases or decreases gene expression.

As used herein, the term "RNA interference" (RNAi) refers to gene silencing mechanisms that involve small RNAs (including miRNA and siRNA) are frequently referred to under the broad term RNAi. Natural functions of RNAi include protection of the genome against invasion by mobile genetic elements such as transposons and viruses, and regulation of gene expression.

RNA interference results in the inactivation or suppression of expression of a gene within an organism. RNAi can be triggered by one of two general routes. First, it can be triggered by direct cellular delivery of short-interfering RNAs (siRNAs, usually ~21 nucleotides in length and delivered in a dsRNA duplex form with two unpaired nucleotides at each 3' end), which have sequence complementarity to a RNA that is the target for suppression. Second, RNAi can be triggered by one of several methods in which siRNAs are formed in vivo from various types of designed, expressed genes. These genes typically express RNA molecules that form intra- or intermolecular duplexes (dsRNA) or a "hairpin" configuration which are processed by natural enzymes (DICER or DCL) to form siRNAs. In some cases, these genes express "hairpin"-forming RNA transcripts with perfect or near-perfect base-pairing; some of the imperfect hairpin-forming transcripts yield a special type of small RNA, termed microRNA (miRNA). In either general method, it is the siRNAs (or miRNAs) that function as "guide sequences" to direct an RNA-degrading enzyme (termed RISC) to cleave or silence the target RNA. In some cases, it is beneficial to integrate an RNAi-inducing gene into the genome of a transgenic organism. An example would be a plant that is modified to suppress a specific gene by an RNAi-inducing transgene. In most methods that are currently in practice, RNAi is triggered in transgenic plants by transgenes that express a dsRNA (either intramolecular or hairpin, or intermolecular in which two transcripts anneal to form dsRNA).

As used herein, the term "RNA silencing" is a general term that is used to indicate RNA-based gene silencing or RNAi.

As used herein, the term "silencing agent" or "silencing molecule", refers to a specific molecule, which can exert an influence on a cell in a sequence-specific manner to reduce or silence the expression or function of a target, such as a target gene or protein. Examples of silence agents include nucleic acid molecules such as naturally occurring or synthetically generated small interfering RNAs (siRNAs), naturally occurring or synthetically generated microRNAs (miRNAs), naturally occurring or synthetically generated dsRNAs, and antisense sequences (including antisense oligonucleotides, hairpin structures, and antisense expression vectors), as well as constructs that code for any one of such molecules.

As used herein, the term "small interfering RNA" (siRNA) refers to a RNA of approximately 21-25 nucleotides that is processed from a dsRNA by a DICER enzyme (in animals) or a DCL enzyme (in plants). The initial DICER or DCL products are double-stranded, in which the two strands are typically 21-25 nucleotides in length and contain two unpaired bases at each 3' end. The individual strands within the double stranded siRNA structure are separated, and typically one of the siRNAs then are associated with a multi-subunit complex, the RNAi-induced silencing complex (RISC). A typical function of the siRNA is to guide RISC to the target based on base-pair complementarity.

As used herein, the term "transcriptional gene silencing" (TGS) refers to a phenomenon that is triggered by the formation of dsRNA that is homologous with gene promoter regions and sometimes coding regions. TGS results in DNA and histone methylation and chromatin remodeling, thereby causing transcriptional inhibition rather than RNA degradation. Both TGS and PTGS depend on dsRNA, which is cleaved into small (21-25 nucleotides) interfering RNAs (Eckhardt, Plant Cell, 14:1433-1436, 2002; Aufsatz et al., Proc. Natl. Acad. Sci. U.S.A., 99:16499-16506, 2002).

As used herein, "transgenic plant" includes a plant that comprises within its genome a heterologous polynucleotide. The heterologous polynucleotide can be either stably integrated into the genome, or can be extra-chromosomal. Preferably, the polynucleotide of the present invention is stably integrated into the genome such that the polynucleotide is passed on to successive generations. A plant cell, tissue, organ, or plant into which the heterologous polynucleotides have been introduced is considered "transformed", "transfected", or "transgenic". Direct and indirect progeny of transformed plants or plant cells that also contain the heterologous polynucleotide are also considered transgenic.

Various methods for the introduction of a desired polynucleotide sequence encoding the desired protein into plant cells are available and known to those of skill in the art and include, but are not limited to: (1) physical methods such as microinjection, electroporation, and microprojectile mediated delivery (biolistics or gene gun technology); (2) virus mediated delivery methods; and (3) *Agrobacterium*-mediated transformation methods.

The most commonly used methods for transformation of plant cells are the *Agrobacterium*-mediated DNA transfer process and the biolistics or microprojectile bombardment mediated process (i.e., the gene gun). Typically, nuclear transformation is desired but where it is desirable to specifically transform plastids, such as chloroplasts or amyloplasts, plant plastids may be transformed utilizing a microprojectile-mediated delivery of the desired polynucleotide.

*Agrobacterium*-mediated transformation is achieved through the use of a genetically engineered soil bacterium belonging to the genus *Agrobacterium*. A number of wild-type and disarmed strains of *Agrobacterium tumefaciens* and *Agrobacterium rhizogenes* harboring Ti or Ri plasmids can be used for gene transfer into plants. Gene transfer is done via the transfer of a specific DNA known as "T-DNA" that can be genetically engineered to carry any desired piece of DNA into many plant species.

*Agrobacterium*-mediated genetic transformation of plants involves several steps. The first step, in which the virulent *Agrobacterium* and plant cells are first brought into contact with each other, is generally called "inoculation". Following the inoculation, the *Agrobacterium* and plant cells/tissues are permitted to be grown together for a period of several hours to several days or more under conditions suitable for growth and T-DNA transfer. This step is termed "co-culture". Following co-culture and T-DNA delivery, the plant cells are treated with bactericidal or bacteriostatic agents to kill or inhibit the *Agrobacterium* remaining in contact with the explant and/or in the vessel containing the explant. If this is done in the absence of any selective agents to promote preferential growth of transgenic versus non-transgenic plant cells, then this is typically referred to as the "delay" step. If done in the presence of selective pressure favoring transgenic plant cells, then it is referred to as a "selection" step. When a "delay" is used, it is typically followed by one or more "selection" steps.

With respect to microprojectile bombardment (U.S. Pat. No. 5,550,318 (Adams et al.); U.S. Pat. No. 5,538,880 (Lundquist et. al.), U.S. Pat. No. 5,610,042 (Chang et al.); and PCT Publication WO 95/06128 (Adams et al.); each of which is specifically incorporated herein by reference in its entirety), particles are coated with nucleic acids and delivered into cells by a propelling force. Exemplary particles include those comprised of tungsten, platinum, and preferably, gold.

An illustrative embodiment of a method for delivering DNA into plant cells by acceleration is the Biolistics Particle Delivery System (BioRad, Hercules, Calif.), which can be used to propel particles coated with DNA or cells through a screen, such as a stainless steel or Nytex screen, onto a filter surface covered with monocot plant cells cultured in suspension.

Microprojectile bombardment techniques are widely applicable, and may be used to transform virtually any plant species. Examples of species that have been transformed by microprojectile bombardment include monocot species such as maize (International Publication No. WO 95/06128 (Adams et al.)), barley, wheat (U.S. Pat. No. 5,563,055 (Townsend et al.) incorporated herein by reference in its entirety), rice, oat, rye, sugarcane, and sorghum; as well as a number of dicots including tobacco, soybean (U.S. Pat. No. 5,322,783 (Tomes et al.), incorporated herein by reference in its entirety), sunflower, peanut, cotton, tomato, and legumes in general (U.S. Pat. No. 5,563,055 (Townsend et al.) incorporated herein by reference in its entirety).

To select or score for transformed plant cells regardless of transformation methodology, the DNA introduced into the cell contains a gene that functions in a regenerable plant tissue to produce a compound that confers upon the plant tissue resistance to an otherwise toxic compound. Genes of interest for use as a selectable, screenable, or scorable marker would include but are not limited to GUS, green fluorescent protein (GFP), luciferase (LUX), antibiotic or herbicide tolerance genes. Examples of antibiotic resistance genes include the penicillins, kanamycin (and neomycin, G418, bleomycin); methotrexate (and trimethoprim); chloramphenicol; kanamycin and tetracycline. Polynucleotide molecules encoding proteins involved in herbicide tolerance are known in the art, and include, but are not limited to a polynucleotide molecule encoding 5-enolpyruvylshikimate-3-phosphate synthase (EPSPS) described in U.S. Pat. No. 5,627,061 (Barry, et al.), U.S. Pat. No 5,633,435 (Barry, et al.), and U.S. Pat. No 6,040,497 (Spencer, et al.) and aroA described in U.S. Pat. No. 5,094,945 (Comai) for glyphosate tolerance; a polynucleotide molecule encoding bromoxynil nitrilase (Bxn) described in U.S. Pat. No. 4,810,648 (Duerrschnabel, et al.) for Bromoxynil tolerance; a polynucleotide molecule encoding phytoene desaturase (crtI) described in Misawa et al. (Plant J. 4:833-840, 1993) and Misawa et al. (Plant Journal 6: 481-489, 1994) for norflurazon tolerance; a polynucleotide molecule encoding acetohydroxyacid synthase (AHAS, aka ALS) described in Sathasiivan et al. (Nucl. Acids Res. 18:2188-2193, 1990) for tolerance to sulfonylurea herbicides; and the bar gene described in DeBlock, et al. (EMBO J. 6:2513-2519, 1987) for glufosinate and bialaphos tolerance.

The regeneration, development, and cultivation of plants from various transformed explants are well documented in the art. This regeneration and growth process typically includes the steps of selecting transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Cells that survive the exposure to the selective agent, or cells that have been scored positive in a screening assay, may be cultured in media that supports regeneration of plants. Developing plantlets are transferred to soil less plant growth mix, and hardened off, prior to transfer to a greenhouse or growth chamber for maturation.

The present invention can be used with any transformable cell or tissue. By transformable as used herein is meant a cell or tissue that is capable of further propagation to give rise to a plant. Those of skill in the art recognize that a number of plant cells or tissues are transformable in which after insertion of exogenous DNA and appropriate culture conditions the plant cells or tissues can form into a differentiated plant. Tissue suitable for these purposes can include but is not limited to immature embryos, scutellar tissue, suspension cell cultures, immature inflorescence, shoot meristem, nodal explants, callus tissue, hypocotyl tissue, cotyledons, roots, and leaves.

Any suitable plant culture medium can be used. Examples of suitable media would include but are not limited to MS-based media (Murashige and Skoog, Physiol. Plant, 15:473-497, 1962) or N6-based media (Chu et al., Scientia Sinica 18:659, 1975) supplemented with additional plant growth regulators including but not limited to auxins, cytokinins, ABA, and gibberellins. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared and modified. Those of skill in the art are aware that media and media supplements such as nutrients and growth regulators for use in transformation and regeneration and other culture conditions such as light intensity during incubation, pH, and incubation temperatures that can be optimized for the particular variety of interest.

One of ordinary skill will appreciate that, after an expression cassette is stably incorporated in transgenic plants and confirmed to be operable, it can be introduced into other plants by sexual crossing. Any of a number of standard breeding techniques can be used, depending upon the species to be crossed.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Identification of the Molecular Target Site for Picolinate Auxins.

Identification of Picolinate Auxin Resistant Mutants

Mutations conferring picolinate auxin-specific resistance can be identified by screening EMS-mutated M2 generation *Arabidopsis* seedlings for plants that can grow in the presence of a normally phytotoxic dose of a picolinate auxin. In a preferred embodiment, this can be a potent picolinate auxin such as a 6-phenyl substituted auxin as described in WO 03/011853A1. Seedling survivors can be recovered and the progeny of these plants further tested for lack of resistance to 2,4-D. This effectively eliminates previously discovered mutants such as axr1 that have non-selective auxin-resistance. The chemical resistance spectrum of mutants that are not resistant to 2,4-D can be characterized by testing with a variety of different auxin herbicides. Genetic inheritance tests can determine if the mutations are dominant or recessive and the sites of the mutations can be determined by genetic mapping.

The invention provides *Arabidopsis* nucleic acids encoding picolinate auxin resistance genes AFB5 and SGT1b, as presented in SEQ ID NO: 1 (GenBank entry gi:30695799) and SEQ ID NO: 3 (GenBank entry gi:17017309). The invention further provides AFB5 and SGT1b protein sequences, as presented in SEQ ID NO: 2 (gi:18423092) and SEQ ID NO: 4 (gi:17017310), respectively. Nucleic acids and/or proteins that are orthologs or paralogs of *Arabidopsis* AFB5 and SGT1b have been identified and are described in Example 8 below. These orthologs or paralogs include AFB4 from *Arabidopsis* (SEQ ID NOs 5 and 6), homolog of AFB5 from *Oryza sativa* (rice) (GenBank entries gi|51979369 and gi|34902411) (SEQ ID NOs 7, 8, 9 and 10) and an AFB5 homolog from Populus (GenBank entry gi|13249029 and gi|13249030) (SEQ ID NOs 11 and 12).

Across the entire length of the proteins, AFB4 and AFB5 share about 80% amino acid identity with each other and members of the AFB4 and AFB5 group all have at least 54% identity with all other members of the group. For example, the protein sequence from Populus has about 70% identity with AFB4 and about 73% identity with AFB5. All members of this group (SEQ ID NOs 5, 6, 7, 8, 9, 10, 11 and 12) are considered to be within, and usable according to, the subject invention.

As used herein, the term "AFB4, AFB5 and SGT1b polypeptides" refers to a full-length AFB4, AFB5 and SGT1b proteins or a fragments, derivatives (variants), or orthologs thereof that are "functionally active," meaning that the protein fragments, derivatives, or orthologs exhibit one or more or the functional activities associated with the polypeptide of SEQ ID NO: 2, SEQ ID NO: 4 or SEQ ID NO: 6. In one preferred embodiment, a functionally active AFB4, AFB5 and SGT1b polypeptides cause an auxin resistant phenotype when misexpressed in a plant. In a further preferred embodiment, misexpression of the AFB4, AFB5 or SGT1b polypeptides causes an auxin-resistant phenotype in a plant. In another embodiment, a functionally active AFB4, AFB5 or SGT1b polypeptide is capable of rescuing defective (including deficient) endogenous AFB4, AFB5 or SGT1b activity when expressed in a plant or in plant cells; the rescuing polypeptide may be from the same or from a different species as that with defective activity. In another embodiment, a functionally active fragment of a full length AFB4, AFB5 or SGT1b polypeptide (i.e., a native polypeptide having the sequence of SEQ ID NO: 2, SEQ ID NO: 4 or SEQ ID NO: 6 or naturally occurring orthologs thereof) retain one of more of the biological properties associated with the full-length AFB5 or SGT1b polypeptides, such as signaling activity, binding activity, catalytic activity, or cellular or extra-cellular localizing activity.

Functionally active variants of full-length AFB4, AFB5 or SGT1b polypeptides or fragments thereof include polypeptides with amino acid insertions, deletions, or substitutions that retain one of more of the biological properties associated with the full-length AFB4, AFB5 or SGT1b polypeptides. These polypeptides may be referred to as modified wild-type proteins, allelic variants or truncated polypeptides. In some cases, variants are generated that change the post-translational processing of an AFB4, AFB5 or SGT1b polypeptides. For instance, variants may have altered protein transport or protein localization characteristics or altered protein half-life compared to the native polypeptide.

Mutant forms of AFB4, AFB5 or SGT1b are referred to as AFB4-m, AFB5-m and SGT1b-m, respectively. The expression of AFB4-m, AFB5-m and SGT1b-m in plants may cause resistance to picolinate auxins.

As used herein, the term "AFB4 nucleic acid", "AFB5 nucleic acid" and "SGT1b nucleic acids encompass nucleic acids with the sequence provided in or complementary to the sequence provided in SEQ ID NO: 5, SEQ ID NO: 1 and SEQ ID NO: 3, respectively, as well as functionally active fragments, derivatives, or orthologs thereof. An AFB4, AFB5 or SGT1b nucleic acid of this invention may be DNA, derived from genomic DNA or cDNA, or RNA.

In one embodiment, a functionally active AFB4, AFB5 or SGT1b nucleic acid encodes or is complementary to a nucleic acid that encodes functionally active AFB4, AFB5 or SGT1b polypeptides, respectively. Included within this definition is genomic DNA that serves as a template for a primary RNA transcript (i.e., an mRNA precursor) that requires processing, such as splicing, before encoding the functionally active AFB4, AFB5 or SGT1b polypeptide. An AFB4, AFB5 or SGT1b nucleic acid can include other non-coding sequences, which may or may not be transcribed; such sequences include 5' and 3' UTRs, polyadenylation signals and regulatory sequences that control gene expression, among others, as are known in the art. Some polypeptides require processing events, such as proteolytic cleavage, covalent modification, etc., in order to become fully active. Accordingly, functionally active nucleic acids may encode the mature or the pre-processed AFB4, AFB5 or SGT1b polypeptide, or an intermediate form. An AFB4, AFB5 or SGT1b polynucleotide can also include heterologous coding sequences, for example, sequences that encode a marker included to facilitate the purification of the fused polypeptide, or a transformation marker.

In another embodiment, a functionally active AFB4, AFB5 or SGT1b nucleic acid is capable of being used in the generation of loss-of-function AFB4, AFB5 or SGT1b phenotypes, for instance, via antisense suppression, co-suppression, etc.

Identification of Orthologs that Bind Picolinate Auxins

Although AFB4, AFB5 and SGT1b genes were discovered in Arabidopsis and the gene and protein information disclosed herein is information derived from the Arabidopsis thaliana sequences, this invention is intended to encompass nucleic acid and protein sequences from other species of plants that are similar to AFB4 (At4g24390; SEQ ID NO: 6), AFB5 (At5g49980; SEQ ID NO: 2) and SGT1b (At4g11260; SEQ ID NO: 4). Some examples are provided below in Example 8.

In one preferred embodiment, a AFB4, AFB5 or SGT1b nucleic acid used in the methods of this invention comprises a nucleic acid sequence that encodes or is complementary to a sequence that encodes AFB4, AFB5 or SGT1b polypeptides having at least 50%, 60%, 70%, 75%, 80%, 85%, 90%, 95% or more sequence identity to the polypeptide sequence presented in SEQ ID NO: 2 or SEQ ID NO: 4.

In another embodiment an AFB4, AFB5 or SGT1b polypeptide of the invention comprises a polypeptide sequence with at least 50% or 60% identity to the AFB4, AFB5 or SGT1b polypeptide sequence of SEQ ID NO: 6, SEQ ID NO: 2 or SEQ ID NO: 4, respectively, and may have at least 70%, 80%, 85%, 90% or 95% or more sequence identity to the AFB4, AFB5 or SGT1b polypeptide sequence of SEQ ID NO: 6, SEQ ID NO: 2 or SEQ ID NO: 4, respectively. In another embodiment, AFB4, AFB5 or SGT1b polypeptides comprise a polypeptide sequence with at least 50%, 60%, 70%, 80%, 85%, 90% or 95% or more sequence identity to a functionally active fragment of the polypeptide presented in SEQ ID NO: 6, SEQ ID NO: 2 or SEQ ID NO: 4, such as a F-box domain or a SGT1 domain, respectively. In yet another embodiment, an AFB4, AFB5 or SGT1b polypeptide comprises a polypeptide sequence with at least 50%, 60%, 70%, 80%, or 90% identity to the polypeptide sequence of SEQ ID NO: 6, SEQ ID NO: 2 or SEQ ID NO: 4 over its entire length and comprises F box domain or SGT1 domain, respectively.

In another aspect, an AFB4, AFB5 or SGT1 b polynucleotide sequence is at least 50% to 60% identical over its entire length to the AFB4, AFB5 or SGT1b nucleic acid sequences presented as SEQ ID NO: 5, SEQ ID NO: 1 or SEQ ID NO: 3, respectively, or nucleic acid sequences that are complementary to such a AFB4, AFB5 or SGT1b sequences, and may comprise at least 70%, 80%, 85%, 90% or 95% or more sequence identity to the AFB4, AFB5 or SGT1b sequence presented as SEQ ID NO: 5, SEQ ID NO: 1 and SEQ ID NO: 3 or a functionally active fragment thereof, or complementary sequences.

As used herein, "percent (%) sequence identity" with respect to a specified subject sequence, or a specified portion thereof, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. 215:403-410, 1997) with search parameters set to default values. The HSP S and HSP S2 parameters are dynamic values and are established by the program itself depending upon the composition of the particular sequence and composition of the particular database against which the sequence of interest is being searched. A "% identity value" is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation. A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Derivative nucleic acid molecules of the subject nucleic acid molecules include sequences that hybridize to the nucleic acid sequence of SEQ ID NO: 5, SEQ ID NO: 1 or SEQ ID NO: 3. The stringency of hybridization can be controlled by temperature, ionic strength, pH, and the presence of denaturing agents such as formamide during hybridization and washing. Conditions routinely used are well known (see, e.g., Current Protocol in Molecular Biology, Vol. 1, Chap. 2.10, John Wiley & Sons, Publishers, 1994; Sambrook et al., Molecular Cloning, Cold Spring Harbor, 1989). In some embodiments, a nucleic acid molecule of the invention is capable of hybridizing to a nucleic acid molecule containing the nucleotide sequence of SEQ ID NO: 5, SEQ ID NO: 1 or SEQ ID NO: 3 under stringent hybridization conditions that are: prehybridization of filters containing nucleic acid for 8 hours to overnight at 65° C. in a solution comprising 6× single strength citrate (SSC) (1× SSC is 0.15 M NaCl, 0.015 M Na citrate; pH 7.0), 5× Denhardt's solution, 0.05% sodium pyrophosphate and 100 µg/ml herring sperm DNA; hybridization for 18-20 hours at 65° C. in a solution containing 6× SSC, 1× Denhardt's solution, 100 µg/ml yeast tRNA and 0.05% sodium pyrophosphate; and washing of filters at 65° C. for 1 h in a solution containing 0.1× SSC and 0.1% SDS (sodium dodecyl sulfate). In other embodiments, moderately stringent hybridization conditions are used that are: pretreatment of filters containing nucleic acid for 6 h at 40° C. in a solution containing 35% formamide, 5× SSC, 50 mM Tris-HCl (pH 7.5), 5 mM EDTA, 0.1% PVP, 0.1% Ficoll, 1% BSA, and 500 µg/ml denatured salmon sperm DNA; hybridization for 18-20 h at 40° C. in a solution containing 35% formamide, 5× SSC, 50 mM Tris-HCl (pH 7.5), 5 mM EDTA, 0.02% PVP, 0.02% Ficoll, 0.2% BSA, 100 µg/ml salmon sperm DNA, and 10% (wt/vol) dextran sulfate; followed by washing twice for 1 hour at 55° C. in a solution containing 2× SSC and 0.1% SDS. Alternatively, low stringency conditions can be used that comprise: incubation for 8 hours to overnight at 37° C. in a solution comprising 20% formamide, 5× SSC, 50 mM sodium phosphate (pH 7.6), 5× Denhardt's solution, 10% dextran sulfate, and 20 µg/ml denatured sheared salmon sperm DNA; hybridization in the same buffer for 18 to 20 hours; and washing of filters in 1× SSC at about 37° C. for 1 hour.

As a result of the degeneracy of the genetic code, a number of polynucleotide sequences encoding an AFB4, AFB5 or SGT1b polypeptides can be produced. For example, codons may be selected to increase the rate at which expression of the polypeptide occurs in a particular host species, in accordance with the optimum codon usage dictated by the particular host organism (see, e.g., Nakamura et al. N A R 27: 292, 1999). Such sequence variants may be used in the methods of this invention.

The methods of the invention may use orthologs of the Arabidopsis AFB4, AFB5 or SGT1b. Methods of identifying the orthologs in other plant species are known in the art. Normally, orthologs in different species retain the same function, due to presence of one or more protein motifs and/or 3-dimensional structures. In evolution, when a gene duplication event follows speciation, a single gene in one species, such as Arabidopsis, may correspond to multiple genes (paralogs) in another. As used herein, the term "orthologs" encompasses paralogs. When sequence data is available for a particular plant species, orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen MA and Bork P, Proc Natl Acad Sci, 95:5849-5856, 1998; Huynen MA et al., Genome Research, 10:1204-1210, 2000). Programs for multiple sequence alignment, such as CLUSTAL (Thompson JD et al, Nucleic Acids Res 22:4673-4680, 1994) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. Nucleic acid hybridization methods may also be used to find orthologous genes and are preferred when sequence data are not available. Degenerate PCR and screening of cDNA or genomic DNA libraries are common methods for finding related gene sequences and are well known in the art (see, e.g., Sambrook et al., Molecular Cloning, Cold Spring Harbor, 1989; Dieffenbach and Dveksler, PCR Methods and Applications 3: S2-S7, 1993). For instance, methods for generating a cDNA library from the plant species of interest and probing the library with partially homologous gene probes are described in Sambrook et al., (Molecular Cloning, Cold Spring Harbor, 1989). A highly conserved portion of the Arabidopsis AFB4, AFB5 or SGT1b coding sequences may be used as probes. AFB4, AFB5 or SGT1b ortholog nucleic acids may hybridize to the nucleic acid of SEQ ID NO: 5, SEQ ID NO: 1 or SEQ ID NO: 3 under high, moderate, or low stringency conditions. After amplification or isolation of a segment of a putative ortholog, that segment may be cloned and sequenced by standard techniques and utilized as a probe to isolate a complete cDNA or genomic clone. Alternatively, it is possible to initiate an EST project to generate a database of sequence information for the plant species of interest. In another approach, antibodies that specifically bind known AFB4, AFB5 or SGT1b polypeptides are used for ortholog isolation (see, e.g., Harlow & Lane, Cold Spring Harbor Laboratory, NY, 1988, 1999). Western blot analysis can determine that AFB4, AFB5 or SGT1b orthologs (i.e., an orthologous protein) is present in a crude extract of a particular plant species. When reactivity is observed, the sequence encoding the candidate ortholog may be isolated by screening expression libraries representing the particular plant species. Expression libraries can be constructed in a variety of commercially available vectors, including lambda gt11, as described in Sambrook, et al., (Molecular Cloning, Cold Spring Harbor, 1989). Once the candidate ortholog(s) are identified by any of these means, candidate orthologous sequence are used as bait (the "query") for the reverse BLAST against sequences from Arabidopsis or other species in which AFB4, AFB5 or SGT1b nucleic acids and/or polypeptide sequences have been identified.

AFB4, AFB5 or SGT1b nucleic acids and polypeptides may be obtained using any available method. For instance, techniques for isolating cDNA or genomic DNA sequences of interest by screening DNA libraries or by using polymerase chain reaction (PCR), as previously described, are well known in the art. Alternatively, nucleic acid sequence may be synthesized. Any known method, such as site directed mutagenesis (Kunkel et al., Methods in Enzymology 204: 125-139, 1991), may be used to introduce desired changes into a cloned nucleic acid.

In general, the methods of the invention involve incorporating the desired form of the AFB4, AFB5 or SGT1b nucleic acids into a plant expression vector for transformation of in plant cells, and the AFB4, AFB5 or SGT1b polypeptides are expressed in the host plant.

An "isolated" AFB4, AFB5 or SGT1b nucleic acid molecule or protein is other than in the form or setting in which it is found in nature. An "isolated" polynucleotide is and separated from least one contaminant nucleic acid molecule with which it is ordinarily associated in the natural source of the AFB4, AFB5 or SGT1b nucleic acid. However, an isolated AFB4, AFB5 or SGT1b nucleic acid molecule includes AFB4, AFB5 or SGT1b nucleic acid molecules contained in cells that ordinarily express AFB4, AFB5 or SGT1b where, for example, the nucleic acid molecule is in a chromosomal location different from that of natural cells.

Chemical Structures of Picolinate Auxins, and Identification of the Binding Site for Picolinate Auxins on AFB4 or AFB5

The binding site of picolinate auxins on AFB4 or AFB5 may be identified by dissecting functional domains of the protein. Assays described in Dharmasiri et al. (2005 Nature 435:441-445) and Kepinski and Leyser (Nature, 435:446-451, 2005) have demonstrated that the natural auxin IAA binds directly to TIR1. Similar assays will be used to demonstrate that picolinate auxins bind to AFB4 or AFB5. Briefly, fusion proteins of AFB4 or AFB5 and the myc epitope will be made and tested for ability to interact with an IAA protein in a picolinate auxin-dependent manner. The interaction of AFB4 or AFB5 and AUX/IAA proteins may be tested in vitro by "pull down" experiments. *Arabidopsis* has approximately 25 AUX/IAA proteins and AFB5 may interact with some or all of them. AUX2 and AUX3 are commonly used in "pull down" experiments with TIR1 and can be used in experiments with AFB4 or AFB5. In "pull down" experiments, antibodies to one protein are used to immunoprecipitate a protein complex. The precipitated proteins are separated by electrophoresis and other proteins in the complex are detected by immunoblot analysis. The "pull down" experiments may be performed with the cloned proteins and antiserum specific for them used for immunoprecipitation and immunodetection. Alternatively epitopes recognized by commercially available antiserum may be fused to the proteins and a commercially available antisera used. For example, sequences encoding the myc epitope (EQKLISEEDL) (SEQ ID NO: 13) may be fused with sequences encoding AFB4 or AFB5 such that the myc epitope is fused at the N or preferably at the C terminus of the AFB4 or AFB5 protein forming AFB4-myc or AFB5-myc fusion proteins, respectively. Similarly, sequences encoding the glutathione S transferase (GST) protein may be fused to sequences encoding the AUX2 protein such that the GST protein is fused at the C terminus of the AUX2 protein. The AFB4-myc or AFB5-myc fusion protein is made by transcribing and translating the gene in a non-plant system. Transcripts encoding the AFB4-myc or AFB5-myc fusion protein may be translated in a cell free system, such as the wheat germ or reticulate lysate systems or the AFB5-myc gene may be transformed into *E. coli*, yeast, insect cells or some other appropriate host and the fusion protein purified from cell extracts. The AUX2-GST fusion protein may be purified similarly. The interaction of the AFB4-myc or AFB5-myc protein with AUX2-GST fusion may be tested by incubating the two proteins in the presence and absence of picolinate auxins such as DAS534, immunoprecipitating protein complexes with the commercially available myc antiserum, resuspending the immunoprecipitate and separating the proteins by electrophoresis. Immunoblot analysis using anti-GST antiserum will determine how much of the AUX2-GST fusion protein is interacting with the AFB4-myc or AFB5-myc protein. Detecting more AUX2-GST protein when DAS534 is included in the assay will indicate that DAS534 stimulates the interaction of AFB4 or AFB5 and AUX2. As a control, similar experiments can be done with TIR1-myc fusion proteins. The TIR1/AUX2 interaction is stimulated weakly or not at all by picolinate auxins.

To determine which portion of the AFB4 or AFB5 protein interacts with picolinate auxins, fusion proteins composed of portions of AFB5 and TIR1 can be constructed. For example the N-terminal portion of TIR1 encoding the F-box can be attached to the C terminal portion of AFB5 encoding the leucine rich repeat (LRR) domain. If the fusion protein should interact less strongly with AUX2 in the presence of picolinate auxins, than the wild-type protein, it may indicate that picolinate auxins interact with the AFB4 or AFB5 in the F-box portion of the protein. Similarly, the N-terminal, F-box encoding portion of AFB4 or AFB5 is fused with the C-terminal, LRR domain encoding portion of TIR1 and be used in "pull down" experiments. In this case, if the fusion protein interacts with AUX2 more strongly than the wild-type TIR1 protein, it will indicate that picolinate auxins interact with F-box proteins through the F-box domain. Using chimeric AFB4-TIR1 or AFB5-TIR1 fusion proteins similar to the ones described above, the picolinate auxin binding site on AFB5 may be determined.

The herbicide DAS534 (compound 173 in PCT publication WO 2003011853), 4-amino-3-chloro-5-fluoro-6-(4-chlorophenyl)pyridine-2-carboxylic acid, has the following chemical structure:

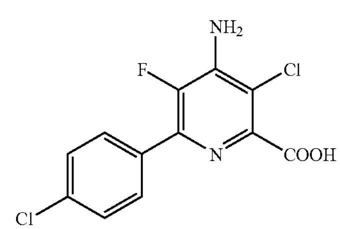

"Picolinate auxins" contain the core structure, 3-chloro-2-picolinic acid:

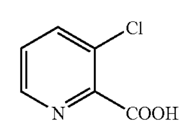

"Aryloxyalkanoate auxins" contain the core structures, 4-chlorophenoxyacetic acid or 2-(4-chlorophenoxy)-propionic acid or 5-chloro-2-pyridinyloxyacetic acid:

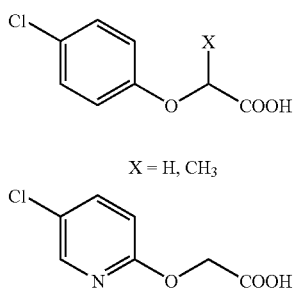

Functional Assay of AFB5 to Identify other Herbicidal Compounds

The "pull down" experiments described above can be used to identify other compounds that stimulate interaction between AFB5 and AUX/IAA proteins. In these experiments, test compounds would be added to the mixture of AFB4 or AFB5 and AUX2. Antiserum to the AFB4 or AFB5 protein would be used to immunoprecipitate protein complexes. These complexes would be resuspended and the proteins separated by electrophoresis. Immunodetection using antiserum to the AUX2 protein would be used to quantitate the amount of AUX2 protein interacting with AFB4 or AFB5. Compounds that stimulate the interaction would be evaluated for auxinic activity on whole plants. Although any compounds could be screened in this assay, the preferred embodiment would be compounds that contain a picolinate or similar moiety.

Ligand-binding Assay of AFB5 to Identify Herbicidal Compounds

Binding of compounds to AFB4 or AFB5 can be detected by ligand displacement techniques wherein a picolinate auxin is labeled with a radioisotope such as tritium or with a tag such as biotin or with a fluorescent moiety. The amount of binding of the picolinate auxin to AFB4 or AFB5 can be detected by separation of the protein from the medium by immunoprecipitation or other protein capture methods. Alternatively alterations in a fluorescent signal from a fluorescence-tagged picolinate on binding to AFB4 or AFB5 can provide a signal for ligand-binding. These detection methods for ligand-binding provide convenient and high-throughput techniques for screening compounds to identify those that inhibit binding of the tagged picolinate auxin to AFB4 or AFB5. These experiments may be facilitated by heterologous expression of AFB4 or AFB5 proteins in a suitable host system such as E. coli or Saccharomyces cerevisiae or via baculovirus expression in insect cell cultures.

Combining in Vitro Assays to Identify Potent Broad Spectrum Auxins

There is redundancy in auxin receptors (AFBs) at the gene and protein level. Current herbicidal auxins interact only with a subset of these proteins for example 2,4-D interacts with TIR1 and close homologs whereas picloram preferentially interacts with AFB4 or AFB5. Consequently a preferred embodiment is to select compounds for optimization by identifying those that interact with TIR1, AFB4 and AFB5 in biochemical ligand-binding or functional assays. This will identify compounds such as DAS534 that interact strongly with both classes of receptor and thus have the potential for increased potency and/or broader spectrum.

Co-crystals of Picolinates and AFB4 or AFB5

Purification of AFB4 or AFB5, especially from heterologous expression systems, allows the protein to be crystallized either on its own or within the E3 protein ligase complex with which it associates. See for example the crystallization of the SCF complex described in Zheng et al. (Nature 416:703-708, 2002). The protein structure can then be determined by X-ray crystallography. Crystallization can be done in the presence and absence of a picolinate auxin ligand by co-crystallography or by ligand-soaking into preformed crystals. This enables the binding region involved in the protein-ligand interaction to be discerned. The features of this molecular interaction can then be used for the design and synthesis of novel compounds that can occupy the site to effect herbicidal activity. Alternatively, the binding pocket can be used as a template to computationally screen and identify compounds with the potential to bind to the site. These can then be experimentally verified as binding to the protein by further in vitro or in vivo assays.

Generation of Genetically Modified Plants with a Picolinate Auxin-resistant Phenotype AFB4, AFB5 or SGT1b nucleic acids and polypeptides may be used in the generation of genetically modified plants having an auxin-resistant phenotype. As used herein, an "auxin resistant phenotype" may refer to resistance to any naturally occurring or synthetic molecule that elicits auxinic herbicidal symptoms when applied to plants. A preferred embodiment is for resistance to compounds containing a picolinate or similar moiety.

The methods described herein are generally applicable to all plants. Although EMS mutagenesis and gene identification was carried out in Arabidopsis, the AFB4, AFB5 and SGT1b genes (or an ortholog, variant or fragment thereof) may be expressed in any type of plant. In a preferred embodiment, the invention is directed to plants known as row crops. Examples of row crop species include soybean (Glycine max), rapeseed and canola (including Brassica napus, B. campestris), sunflower (Helianthus annuus), cotton (Gossypium hirsutum), corn (Zea mays), cocoa (Theobroma cacao), safflower (Carthamus tinctorius), oil palm (Elaeis guineensis), coconut palm (Cocos nucifera), flax (Linum usitatissimum), castor (Ricinus communis), sorghum (Sorghum bicolor) and peanut (Arachis hypogaea). The invention may also be directed to fruit-and vegetable-bearing plants, grain-producing plants, nut-producing plants, rapid cycling Brassica species, alfalfa (Medicago sativa), tobacco (Nicotiana spp.), turfgrass (Poaceae family), clover (Trifolium spp.) and other forage crops.

The auxin-resistant phenotype may be generated by expressing AFB4, AFB5 or SGT1b gene in antisense or hairpin RNAS, by over-expressing AFB4, AFB5 or SGT1b and causing co-suppression, or by developing a dominant negative protein that inhibits the function of the native protein. Antisense RNAs are formed when the coding sequences of a protein encoding nucleic acid are expressed in the opposite orientation. These RNAs can hybridize with mRNAs transcribed from endogenous genes and inhibit their expression. Hairpin RNAs are formed when all or a portion of the coding sequences of a gene are cloned in the sense and antisense orientation in the same transcription unit. Upon transcription of these constructs, the transcript forms a hairpin structure and triggers a transcript degradation pathway that targets both the hairpin-encoding gene and the endogenous gene. This degradation pathway can effectively silence endogenous gene expression (Smith et al. Nature 407:319-320, 2000). Co-suppression is caused by the over-expression of a transgene; high level of expression can cause the degradation of transcripts from the native gene (Que et al. Plant Cell 9:1357-1368, 1997). Dominant negative mutants may be generated by over-expressing a mutant form of the protein (Pontier et al., Plant Cell 27:529-538, 2001). Since AFB4, AFB5 and SGT1b interact with components of the SCF complex, over-expression of mutant forms of the proteins may disrupt the auxin-responsive SCF complex, prevent auxin signaling and cause the transgenic plants to be auxin resistant.

The skilled artisan will recognize that a wide variety of transformation techniques exist in the art, and new techniques are continually becoming available. Any technique that is suitable for the target host plant can be employed within the scope of the present invention. For example, the constructs can be introduced in a variety of forms including, but not limited to as a strand of DNA, in a plasmid, or in an artificial chromosome. The introduction of the constructs into the target plant cells can be accomplished by a variety of techniques, including, but not limited to Agrobacterium-mediated transformation, electroporation, microinjection, microprojectile bombardment calcium-phosphate-DNA co-precipitation or liposome-mediated transformation of a heterologous nucleic acid. The transformation of the plant is preferably permanent, i.e. by integration of the introduced expression constructs into the host plant genome, so that the introduced constructs are passed onto successive plant generations. Depending upon the intended use, a heterologous nucleic acid construct comprising an AFB4, AFB5 or SGT1b polynucleotide may encode the entire protein or a biologically active portion thereof.

In one embodiment, binary Ti-based vector systems may be used to transfer polynucleotides. Standard Agrobacterium binary vectors are known to those of skill in the art, and many are commercially available (e.g., pBI121 Clontech Laboratories, Palo Alto, Calif.). A construct or vector may include a plant promoter to express the nucleic acid molecule of choice. In a preferred embodiment, the promoter is a plant promoter.

The optimal procedure for transformation of plants with Agrobacterium vectors will vary with the type of plant being transformed. Exemplary methods for Agrobacterium-mediated transformation include transformation of explants of hypocotyl, shoot tip, stem or leaf tissue, derived from sterile seedlings and/or plantlets. Such transformed plants may be reproduced sexually, or by cell or tissue culture. Agrobacterium transformation has been previously described for a large number of different types of plants and methods for such transformation may be found in the scientific literature. Of particular relevance are methods to transform commercially important crops, such as rapeseed (De Block et al., Plant Physiol 91: 694-701, 1989), sunflower (Everett et al., Bio/Technology 5: 1201-1204, 1987), and soybean (Christou et al., Proc Natl Acad Sci USA 86: 7500-7504, 1989; Kline et al., Nature 327: 70-73, 1987).

Expression (including transcription and translation) of AFB4, AFB5 or SGT1b may be regulated with respect to the level of expression, the tissue type(s) where expression takes place and/or developmental stage of expression. A number of heterologous regulatory sequences (e.g., promoters and enhancers) are available for controlling the expression of an AFB4, AFB5 or SGT1b nucleic acid. These include constitutive, inducible and regulatable promoters, as well as promoters and enhancers that control expression in a tissue- or temporal-specific manner. Exemplary constitutive promoters include, but are not limited to, the raspberry E4 promoter (U.S. Pat. Nos. 5,783,393 and 5,783,394), the nopaline synthase (NOS) promoter (Ebert et al., Proc. Natl. Acad. Sci. (U.S.A.) 84:5745-5749, 1987), the octopine synthase (OCS) promoter (which is carried on tumor-inducing plasmids of Agrobacterium tumefaciens), the caulimovirus promoters such as the cauliflower mosaic virus (CaMV) 19S promoter (Lawton et al., Plant Mol. Biol. 9:315-324, 1987) and the CaMV 35S promoter (Odell et al., Nature 313:810-812, 1985 and Jones et al, Transgenic Res. 1(6):285-297, 1992), the melon actin promoter (published PCT application WO0056863), the figwort mosaic virus 35S-promoter (U.S. Pat. No. 5,378,619), the light-inducible promoter from the small subunit of ribulose-1,5-bis-phosphate carboxylase (ss-RUBISCO), the Adh promoter (Walker et al., Proc. Natl. Acad. Sci. (U.S.A.) 84:6624-6628, 1987), the sucrose synthase promoter (Yang et al., Proc. Natl. Acad. Sci. (U.S.A.) 87:4144-4148, 1990), the R gene complex promoter (Chandler et al., The Plant Cell 1: 1175-1183, 1989), the chlorophyll a/b binding protein gene promoter the CsVMV promoter (Verdaguer et al., Plant Mol Biol 37: 1055-1067, 1998), these promoters have been used to create DNA constructs that have been expressed in plants; see, e.g., PCT publication WO 84/02913. Exemplary tissue-specific promoters include the tomato E4 and E8 promoters (U.S. Pat. No. 5,859,330) and the tomato 2AII gene promoter (Van Haaren et al., Plant Mol Biol 21: 625-640, 1993).

In yet another aspect, in some cases it may be desirable to inhibit the expression of endogenous AFB4, AFB5 or SGT1b in a host cell. Exemplary methods for practicing this aspect of the invention include, but are not limited to antisense suppression (Smith, et al., Mol Gen Genet 224: 477-481, 1988; van der Krol et al., BioTechniques 6: 958-976, 1988); co-suppression (Napoli, et al., Plant Cell 2: 279-289, 1990); ribozymes (PCT Publication WO 97/10328); and combinations of sense and antisense (Waterhouse, et al., Proc Natl Acad Sci USA 95: 13959-13964, 1998). Methods for the suppression of endogenous sequences in a host cell typically employ the transcription or transcription and translation of at least a portion of the sequence to be suppressed. Such sequences may be homologous to coding as well as non-coding regions of the endogenous sequence. Antisense inhibition may use the entire cDNA sequence (Sheehy et al., Proc Natl Acad Sci USA 85: 8805-8809, 1988), a partial cDNA sequence including fragments of 5' coding sequence, (Cannon et al., Plant Mol Biol 15: 39-47, 1990), or 3' non-coding sequences (Ch'ng et al., Proc Natl Acad Sci USA 86: 10006-10010, 1989). Cosuppression techniques may use the entire cDNA sequence (Napoli et al., Plant Cell 2: 279-289, 1990; van der Krol et al., Plant Cell 2: 291-299, 1990), or a partial cDNA sequence (Smith et al., Mol Gen Genet 224: 477-481, 1990).

AFB4, AFB5 or SGT1b activity can be decreased by decreasing in the expression levels of AFB4, AFB5 or SGT1b and/or decreasing the activity of AFB4, AFB5, or SGT1b collectively these are referred to as "gene down-regulation mechanisms". Decreased activity of AFB4, AFB5 or SGT1b can be obtained, for example, by decreasing expression of the AFB4, AFB5 or SGT1b polypeptides, or variants or fragments thereof. For example, a nucleotide sequence may be introduced into a cell or plant that encodes a protein that leads to decreased AFB4, AFB5, or SGT1b expression, such as a protein that interferes with the AFB4, AFB5 or SGT1b promoter. Alternatively, a non protein-encoding nucleotide sequence that decreases (inhibits) expression of AFB4, AFB5 or SGT1b, or variant or fragment thereof, may be introduced into a cell or plant. The inhibitory nucleotide sequence may hybridize to a nucleotide sequence encoding the AFB4, AFB5 or SGT1b polypeptide, or variant or fragment thereof. Inhibitory nucleotide sequences include, but are not limited to, an antisense nucleotide sequence, a siRNA or a ribozyme. A chemical compound that is capable of decreasing AFB4, AFB5 or SGT1b expression may be introduced into the cell or plant.

In one embodiment, inhibition of AFB4, AFB5, or SGT1b activity is obtained through the use of antisense technology. Antisense oligonucleotides as a method of suppression are well known in the art. Although the exact mechanism by which antisense RNA molecules interfere with gene expression has not been elucidated, it is believed that antisense RNA molecules bind to the endogenous mRNA molecules and thereby inhibit translation of the endogenous mRNA.

Herein is provided a means to alter levels of expression of AFB4, AFB5, or SGT1b by the use of a synthetic antisense oligonucleotide compound that inhibits translation of mRNA encoding AFB4, AFB5, or SGT1b. Synthetic antisense oligonucleotides, or other antisense chemical structures designed to recognize and selectively bind to mRNA, are constructed to be complementary to portions of the nucleotide sequence shown in SEQ ID NO: 1, SEQ ID NO: 3 and SEQ ID NO: 5. In addition, the antisense oligonucleotide may be designed for administration only to certain selected cell populations by targeting the antisense oligonucleotide to be recognized by specific cellular uptake mechanisms that bind and take up the antisense oligonucleotide only within certain selected cell populations. For example, the antisense oligonucleotide may be designed to bind to transporter found only in a certain cell type. The antisense oligonucleotide may be designed to inactivate the AFB4, AFB5, or SGT1b mRNA by (1) binding to the AFB4, AFB5, or SGT1b mRNA and thus inducing degradation of the mRNA by intrinsic cellular mechanisms such as RNase I digestion, (2) by inhibiting translation of the mRNA target by interfering with the binding of translation-regulating factors or of ribosomes, or (3) by inclusion of other chemical structures, such as ribozyme sequences or reactive chemical groups, which either degrade or chemically modify the target mRNA. Synthetic antisense oligonucleotide drugs have been shown to be capable of the properties described above when directed against mRNA targets (Cohen, Trends Pharmacol. Sci. 10:435-437, 1989). In addition, coupling of ribozymes to antisense oligonucleotides is a promising strategy for inactivating target mRNA (Sarver et al., Science 247: 1222-1225, 1990). In this manner, an antisense oligonucleotide directed to AFB4, AFB5, or SGT1b can be used to reduce AFB4, AFB5, or SGT1b expression in particular target cells.

The introduced sequence need not be the full-length AFB4, AFB5, or SGT1b cDNA (SEQ ID NO: 5, SEQ ID NO: 1 and SEQ ID NO: 3, respectively) and need not be exactly homologous to the equivalent sequence found in the cell type to be transformed. The sequence may comprise a flanking region of AFB4, AFB5, or SGT1b. Flanking regions of AFB4, AFB5, or SGT1b in any target plant may be obtained using the sequences provided herein.

In one embodiment, portions or fragments of the AFB4, AFB5, or SGT1b cDNA (SEQ ID NO: 5, SEQ ID NO: 1 and SEQ ID NO: 3, respectively) could be used to knock out expression of the AFB4, AFB5, or SGT1b gene. Generally, however, where the introduced sequence is of shorter length, a higher degree of identity to the native AFB4, AFB5, or SGT1b sequence will be needed for effective antisense suppression. In other embodiments, the introduced antisense sequence in the vector may be at least 15 nucleotides in length, and improved antisense suppression typically will be observed as the length of the antisense sequence increases. In yet other embodiments, the length of the antisense sequence in the vector advantageously may be greater than 100 nucleotides, and can be up to about the full length of the AFB4, AFB5, or SGT1b cDNA or gene. In another embodiment, for suppression of the AFB4, AFB5, or SGT1b gene itself, transcription of an antisense construct results in the production of RNA molecules that are the reverse complement of mRNA molecules transcribed from the endogenous AFB4, AFB5, or SGT1b gene in the cell.

In one embodiment, the oligonucleotide is at least about 10 nucleotides in length, such as, greater than about 20 bases in length, greater than about 30 bases in length, greater than about 40 bases in length, greater than about 50 bases in length, greater than about 100 bases in length, greater than about 200 bases in length or greater than about 300 bases in length. In one embodiment, the oligonucleotide has a ribozyme activity.

In one specific, non-limiting embodiment, a nucleotide sequence from an AFB4, AFB5, or SGT1b encoding sequence is arranged in reverse orientation relative to the promoter sequence in the transformation vector.

The synthesis of effective anti-sense inhibitors is known. Synthetic antisense oligonucleotides may be produced, for example, in a commercially available oligonucleotide synthesizer. Numerous approaches have been previously described and generally involve altering the backbone of the polynucleotide to increase its stability in vivo. Exemplary oligonucleotides and methods of synthesis are described in U.S. Pat. Nos. 5,661,134; 5,635,488; and 5,599,797 (phosphorothioate linkages), U.S. Pat. Nos. 5,587,469 and 5,459,255 (N-2 substituted purines), U.S. Pat. No. 5,539,083 (peptide nucleic acids) and U.S. Pat. Nos. 5,629,152; 5,623,070; and 5,610,289 (miscellaneous approaches).

In another embodiment, suppression of endogenous AFB4, AFB5, or SGT1b expression can be achieved using ribozymes. Ribozymes are synthetic RNA molecules that possess highly specific endoribonuclease activity. The production and use of ribozymes are disclosed in U.S. Pat. No. 4,987,071 to Cech and U.S. Pat. No. 5,543,508 to Haselhoff. In one embodiment, the inclusion of ribozyme sequences within antisense RNAs may be used to confer RNA cleaving activity on the antisense RNA, such that endogenous mRNA molecules that bind to the antisense RNA are cleaved, which in turn leads to an enhanced antisense inhibition of endogenous gene expression. In yet another embodiment, dominant negative mutant forms of AFB4, AFB5, or SGT1b may be used to block endogenous AFB4, AFB5, or SGT1b activity.

Decreased activity of AFB4, AFB5, or SGT1b may also be obtained by decreasing the activity of the AFB4, AFB5, or SGT1b protein with or without decreasing expression levels. For example, a nucleotide sequence encoding a protein that inhibits or inactivates AFB4, AFB5, or SGT1b activity may be introduced into the cell or plant.

In one embodiment, a mutant or variant of AFB4, AFB5, or SGT1b is introduced or expressed in a cell. The variant of AFB4, AFB5, or SGT1b optionally may have increased expression or decreased expression. Cells may have AFB4, AFB5, or SGT1b null mutations, AFB4, AFB5, or SGT1b missense mutations, AFB4, AFB5, or SGT1b truncation mutations, or inactivation of AFB4, AFB5, or SGT1b. In one embodiment, a mutant AFB4, AFB5, or SGT1b is expressed in a cell but is incapable of localizing to the correct subcellular location. In another embodiment, a mutant AFB4, AFB5, or SGT1b is incapable of binding to one or more of its intracellular binding partners. In yet another embodiment, a mutation in the upstream regulatory region of the AFB4, AFB5, or SGT1b gene abrogates the expression of the protein. In another embodiment, a mutant AFB4, AFB5, or SGT1b is incapable of forming an active SCF complex.

It is possible that mutations in the AFB4, AFB5, or SGT1b gene are not included in the cDNA but rather are located in other regions of the AFB4, AFB5, or SGT1b gene. Mutations located outside of the ORF that encode the AFB4, AFB5, or SGT1b protein are not likely to affect the functional activity of the proteins, but rather are likely to result in altered levels of the proteins in the cell. For example, mutations in the promoter region of the AFB4, AFB5, or SGT1b gene may prevent transcription of the gene and therefore lead to the complete absence of the AFB4, AFB5, or SGT1b protein, or absence of certain transcripts of the protein, in the cell.

Additionally, mutations within introns in the genomic sequence may also prevent expression of the AFB4, AFB5, or SGT1b protein. Following transcription of a gene containing introns, the intron sequences are removed from the RNA molecule, in a process termed splicing, prior to translation of the RNA molecule that results in production of the encoded protein. When the RNA molecule is spliced to remove the introns, the cellular enzymes that perform the splicing function recognize sequences around the intron/exon border and in this manner recognize the appropriate splice sites. If a mutation exists within the sequence of the intron near and exon/intron junction, the enzymes may not recognize the junction and may fail to remove the intron. If this occurs, the encoded protein will likely be defective. Thus, mutations inside the intron sequences within the AFB4, AFB5, or SGT1b gene (termed "splice site mutations") may also lead to defects in transporter activity. However, knowledge of the exon structure and intronic splice site sequences of the AFB4, AFB5, or SGT1b gene is required to define the molecular basis of these abnormalities. The provision herein of AFB4, AFB5, or SGT1b cDNA sequences enables the cloning of the entire AFB4, AFB5, or SGT1b gene (including the promoter and other regulatory regions and the intron sequences) from any target plant, and the determination of its nucleotide sequence.

Standard molecular and genetic tests may be performed to further analyze the association between a gene and an observed phenotype. Exemplary techniques are described below.

1. DNA/RNA Analysis

The stage- and tissue-specific gene expression patterns in mutant versus wild-type lines may be determined, for instance, by in situ hybridization. Analysis of the methylation status of the gene, especially flanking regulatory regions, may be performed. Other suitable techniques include overexpression, ectopic expression, expression in other plant species and gene knock-out (reverse genetics, targeted knock-out, viral induced gene silencing [VIGS, see Baulcombe D, Current Opinion in Plant Biology 2: 109-113, 1999]).

In one preferred application, expression profiling (generally by microarray analysis) is used to simultaneously measure differences or induced changes in the expression of many different genes. Techniques for microarray analysis are well known in the art (Schena M et al., Science 270:467-470, 1995; Baldwin et al., Curr Opin Plant Biol. 2(2):96-103, 1999; Dangond F, Physiol Genomics 2:53-58, 2000; van Hal NL et al., J Biotechnol 78:271-280, 2000; Richmond & Somerville, Curr Opin Plant Biol 3:108-116, 2000). Expression profiling of individual tagged lines may be performed. Such analysis can identify other genes that are coordinately regulated as a consequence of the over-expression of the gene of interest, which may help to place an unknown gene in a particular pathway.

2. Gene Product Analysis

Analysis of gene products may include recombinant protein expression, antisera production, immunolocalization, biochemical assays for catalytic or other activity, analysis of phosphorylation status, and analysis of interaction with other proteins via yeast two-hybrid assays.

3. Pathway Analysis

Pathway analysis may include placing a gene or gene product within a particular biochemical, metabolic or signaling pathway based on its mis-expression phenotype or by sequence homology with related genes. Alternatively, analysis may comprise genetic crosses with wild-type lines and other mutant lines (creating double mutants) to order the gene in a pathway, or determining the effect of a mutation on expression of downstream "reporter" genes in a pathway.

Generation of Mutated Plants with a Picolinate-resistance Phenotype

The invention further provides a method of identifying plants that have mutations in endogenous AFB4, AFB5 or SGT1b that confer auxin resistance. In one method, called "TILLING" (for Targeting Induced Local Lesions IN Genomes), mutations are induced in the seed of a plant of interest, for example, using EMS treatment. The resulting plants are grown and self-fertilized, and the progeny are used to prepare DNA samples. Gene specific PCR is used to identify whether a mutated plant has an AFB4, AFB5 or SGT1b mutation. Plants having AFB4, AFB5 or SGT1b mutations may then be tested for auxin resistance, or alternatively, plants may be tested for auxin resistance, and then AFB4, AFB5 or SGT1b—specific PCR is used to determine whether a resistant plant has a mutated AFB4, AFB5 or SGT1b gene. TILLING can identify mutations that may alter the expression of specific genes or the activity of proteins encoded by these genes (see Colbert et al., Plant Physiol 126:480-484, 2001; McCallum et al., Nature Biotechnology 18:455-457, 2000).

In another method, a candidate gene/Quantitative Trait Locus (QTLs) approach can be used in a marker-assisted breeding program to identify alleles of or mutations in AFB4, AFB5 or SGT1b or orthologs that may confer auxin resistance (see Bert et al., Theor Appl Genet., 107(l):181-9, 2003; and Lionneton et al., Genome. 45(6):1203-15, 2002). Thus, in a further aspect of the invention, an AFB4, AFB5 or SGT1b nucleic acid is used to identify whether a plant having an auxin-resistant phenotype has a mutation in endogenous AFB4, AFB5 or SGT1b or has a particular allele that causes auxin resistance.

While the invention has been described with reference to specific methods and embodiments, it will be appreciated that various modifications and changes may be made without departing from the invention. All publications cited herein are expressly incorporated herein by reference for the purpose of describing and disclosing compositions and methodologies that might be used in connection with the invention. All cited patents, patent applications, and sequence information in referenced public databases are also incorporated by reference.

Following are examples that illustrate procedures for practicing embodiments of the invention. These examples should not be construed as limiting. All percentages are by weight and all solvent mixture proportions are by volume unless otherwise noted.

EXAMPLE 1

Identification and Genetic Characterization of Mutants Resistant to DAS534

To identify mutants resistant to picolinate auxins, EMS-mutagenized M2 seedlings were screened for resistance to DAS534, a 6-phenylpicolinate auxin (Compound 173 in WO 03/011853A1). The seedlings were grown on agarose medium containing 10 nM DAS534. This concentration was sufficient to produce marked auxinic effects on the seedlings including significant inhibition (60%) of root growth. From a total of 780,100 EMS M2 seedlings, 125 putative resistant mutants were identified by visual inspection. Seeds were recovered from 33 of these plants. Selection of lines for further study was based on the strength of resistance, elimination of potential siblings and the health and fertility of adult plants. To avoid recovering alleles of previously characterized mutants, we preferentially selected lines that showed low or no cross resistance to 0.045 μM 2,4-D. Seven lines resistant to DAS534 had negligible resistance to 2,4-D at this concentration (R009; R024; R045; R127; R051; R107; R118) and were further evaluated. One additional line (R090) showing robust resistance to both DAS534 and 2,4-D was also identified.

The mutants were crossed with wild-type Col-0 plants and the progeny were analyzed for resistance to DAS534. The $F_1$ plants that resulted from these crosses were all sensitive to DAS534 indicating that the mutations in all of the resistant lines were recessive to the wild type allele. To determine the number of genetic loci identified in this screen, complementation tests were performed by crossing the herbicide-resistant mutants with each other and the known auxin-resistant mutant axr1-3 in a pair-wise fashion. Analysis of the F1 progeny from these crosses by testing for resistance to 10 nM DAS534 revealed that three distinct DAS534-resistant loci were present in the DAS534-resistant mutants. Complementation Group 1 contained the mutants R009, R024, R045 and R127, and complementation Group 2 contained the mutants R051, R107 and R118. All seven selectively-resistant mutant lines were phenotypically normal when grown on agarose medium or in soil and they had normal fertility. The seedlings exhibited normal gravitropism and had normal morphology under etiolating conditions. Group 2 mutants typically exhibited slightly longer roots (~15%) than wild type plants when grown on agarose medium lacking herbicide. Complementation Group 3 contained the mutant R090 which was resistant to both DAS534 and 2,4-D as well as the known auxin-resistant mutant axr1-3. As the mutations in R090 and axr1-3 appeared to be allelic, R090 was not examined further.

EXAMPLE 2

Chemical Selectivity of Picolinate Auxin Resistant Mutants

The dose responses of root growth of the mutant lines treated with a variety of auxins were measured to define the level and chemical spectrum of resistance in detail. Mutant lines from complementation Groups 1 and 2 had 6 to 8-fold resistance to DAS534 (FIG. 1A). No significant differences in resistance between lines within each complementation group were noted (data not shown). The mutants were very cross-resistant to the picolinate auxin herbicide picloram (FIG. 1B) showing 26 to 60-fold increases in $GR_{50}$ over that of wild type. Group 2 mutants were slightly more resistant than Group 1 lines. In contrast to the response to DAS534 and picloram, the lines from both complementation groups showed negligible resistance to 2,4-D (FIG. 1C) and a slight increase in sensitivity to IAA (FIG. 1D). The fold resistance levels of the mutants are summarized in Table 1.

Figure 2:
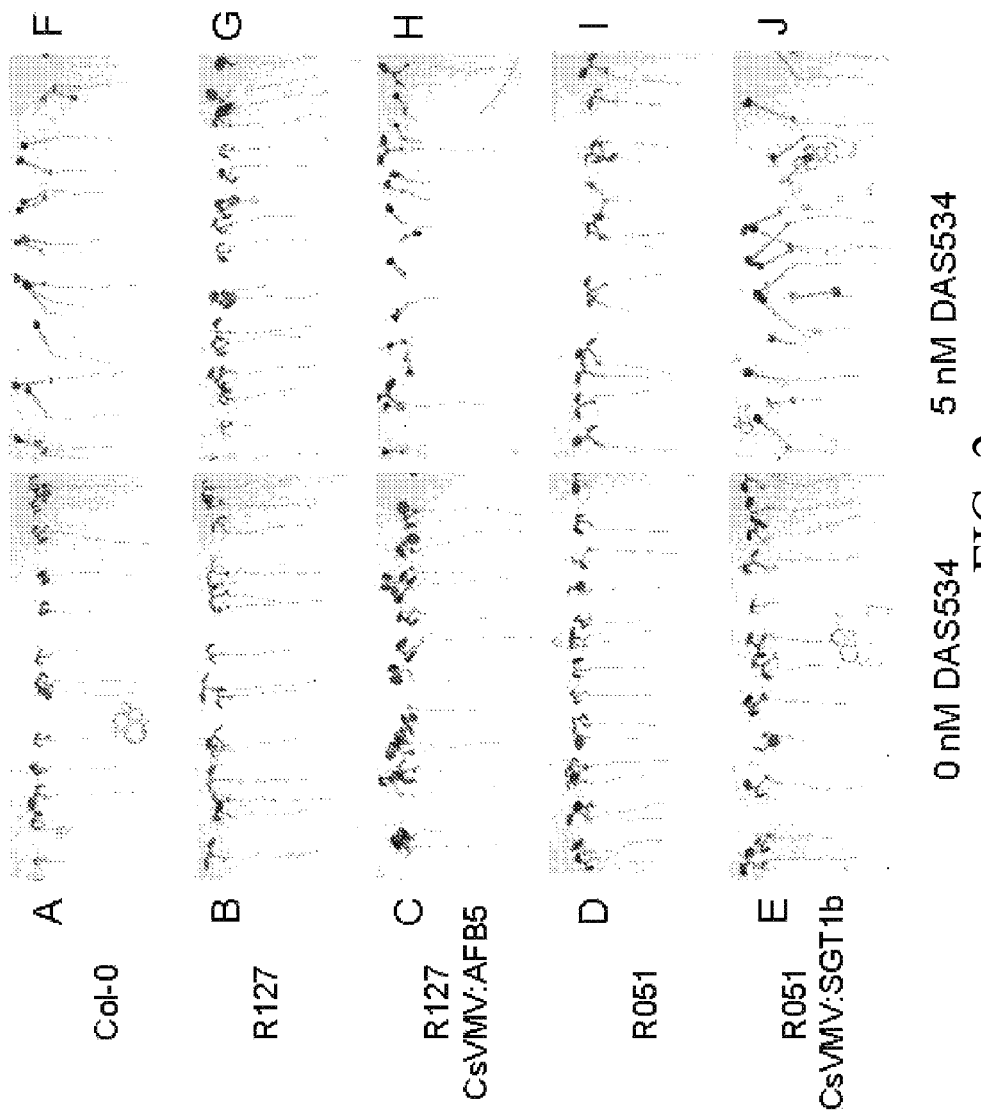
FIGS. 2A-2J. DAS534-resistant mutants and complementation with AFB5 and SGT1b.

Wild-type, Group 1 and Group 2 seedlings growing on 5 nM DAS534 are shown in FIG. 2. At this concentration of DAS534, wild-type plants show slight agravitopism, have elongated hypocotyls and are unable to fully expand their cotyledons (FIG. 2A and FIG. 2F) whereas hypocotyl elongation and cotyledon expansion in the Group 1 mutant R127 and Group 2 mutant R051 are unaffected by DAS534 (FIGS. 2B, 2D, 2G and 2I).

Four additional herbicidal compounds were also tested on the Group 1 line, R127. R127 had 50-fold resistance to the picolinate auxinic herbicide clopyralid. However, it showed no resistance to the benzoate auxin dicamba or to a close analog of the aryloxyacetate auxin, fluroxypyr or to 1-naphthylacetic acid (1-NAA). It also exhibited no difference in response to the auxin transport inhibitor, napthylphthalamic acid (NPA).

In summary, the Group 1 and Group 2 mutants displayed clear chemical selectivity in their resistance profiles toward the picolinate class of auxin herbicides.

EXAMPLE 3

Mapping and Identification of DAS534-Resistance Mutations

To identify the genes involved in this chemical selectivity, one mutation from each complementation group (R009 from Group 1 and R051 from Group 2) was genetically mapped. To generate the mapping population, a homozygous mutant $M_3$ line (from the Col-0 accession) was crossed with a wild-type plant of the Ler accession and the resulting $F_1$ plants were allowed to self-fertilize and produce $F_2$ seed. The $F_2$ seed were germinated on solid medium containing a sublethal concentration of DAS534. Plants resistant to the herbicide were removed from the herbicide-containing medium and allowed to recover on solid medium lacking the herbicide for seven days and then transplanted to soil. When the plants were at the rosette stage, a single leaf was removed and genomic DNA was isolated and used in mapping experiments with molecular genetic markers.

Figure 3:
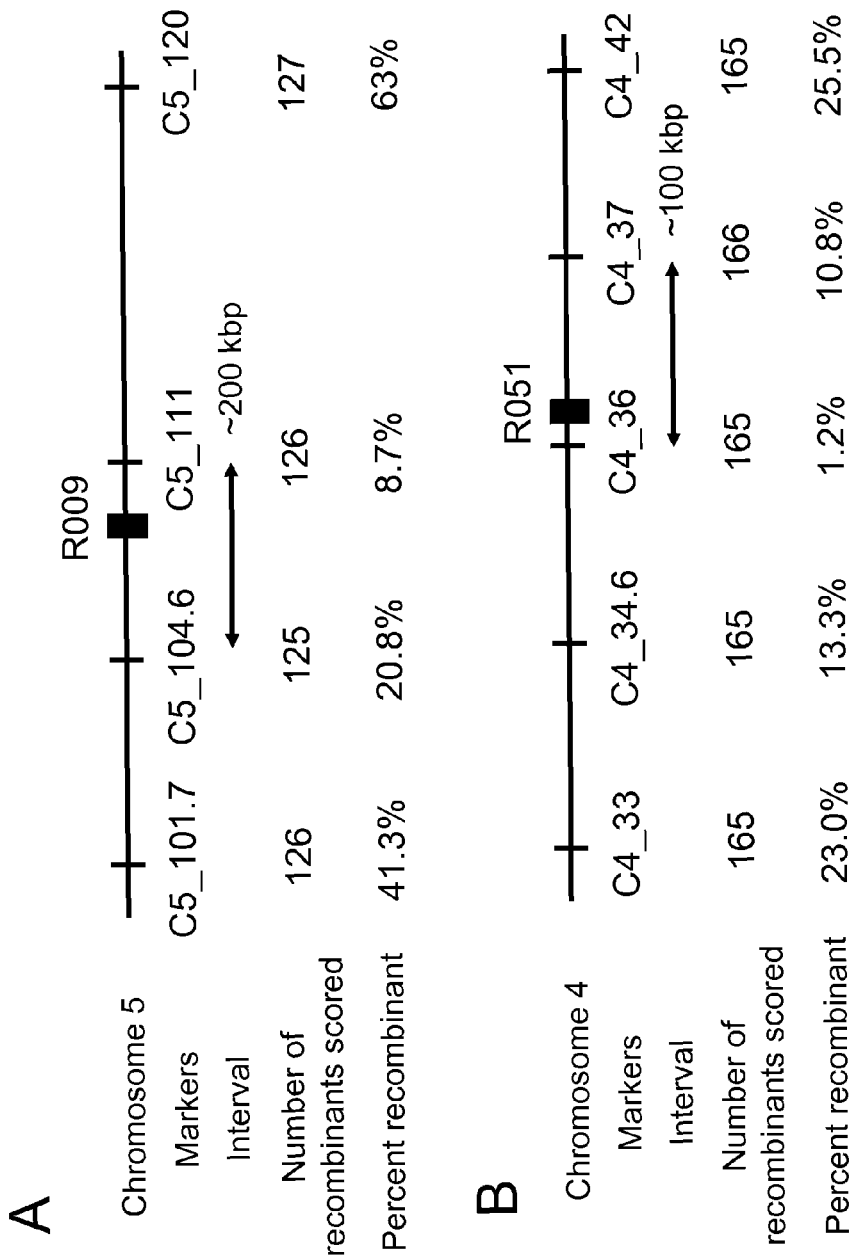
FIGS. 3A-3B. Map-based cloning of the resistance mutations in R009 and R051. The horizontal line represents the chromosome, the vertical hatched lines show the position of the markers used in fine mapping experiments.
Figure 4:
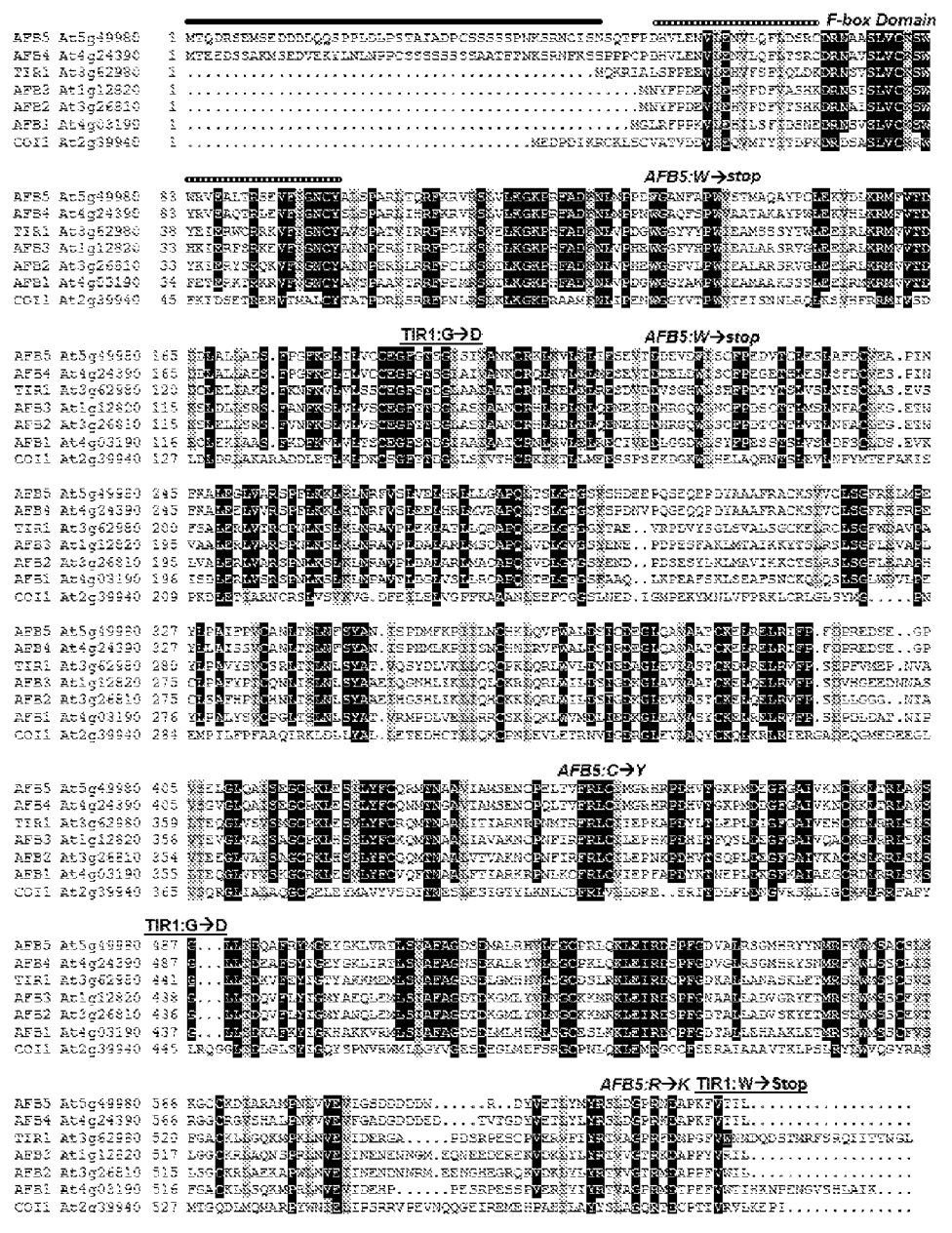

The mutation in R009 was mapped to a 200 kb interval around 105 cM on chromosome 5 between the markers C5_104.6 and C5_111 (FIG. 3). This interval contains 47 genes including At5g49980 annotated by the *Arabidopsis* Information Resource as a homolog of TIR1. TIR1 is an F-box protein involved in 2,4-D and IAA-mediated SCF function and has recently been shown to be a receptor for auxin (Dharmasiri et al., Nature. 435(7041):441-445, 2005). tir1 mutants are resistant to 2,4-D and IAA (Ruegger et al., Genes Dev 12: 198-207, 1998). Because of this possible linkage to auxin function, At5g49980 was PCR amplified from genomic DNA from the four Group 1 mutant lines and Col-0 plants and compared by DNA sequence analysis. All four DAS534-resistant lines contained G to A mutations in At5g49980 relative to the Col-0 sequence resulting in changes in the encoded polypeptide. The mutations in the deduced amino acid sequences from R024 and R127 introduce stop codons at amino acid residues 220 and 124, respectively. The mutations in R009 and R045 introduce amino acid changes in the encoded polypeptide sequence producing an R to K mutation at position 609 in R009 and a C to Y mutation at position 451 in R045 (FIG. 4).

There are six members of the F-box protein subclass that includes TIR1 in the *Arabidopsis* genome (Gagne et al., Proc Natl Acad Sci USA 99: 11519-11524, 2002). The three closest homologs have been named AFB1, 2 and 3 (Dharmasiri et al., Dev Cell. 9(1):109-119, 2005). For consistency, we have denoted the two remaining homologs (At4g24390 and At5g49980) as AFB4 and AFB5 respectively. DNA and protein sequences for AFB4 are provided as SEQ ID NOS:5 and 6, respectively. To confirm that the picolinate auxin resistant phenotypes in Group 1 mutants were caused by the identified lesions in AFB5, the auxin-resistance phenotype was complemented by transformation of the R127 mutant line with a construct containing a wild-type copy of AFB5 driven by the CsVMV promoter (Verdaguer et al., Plant Mol Biol 37: 1055-1067, 1998). T1 plants containing the transgene were selected, allowed to self-fertilize and set seed. T2 seeds that were segregating for the transgene were germinated on medium containing 10 nM DAS534 and the seedlings were scored for sensitivity to the herbicide. Ten independent transformants were identified that restored auxin sensitivity to the mutant (FIG. 2H). Some of these transformants appeared to be hypersensitive to DAS534 because their roots were significantly shorter than those of wild-type plants when grown on herbicide-containing medium. These data confirm that the mutation in AFB5 is indeed responsible for the resistance phenotype in Group 1 mutants. As the DAS534-resistant mutants in complementation Group 1 are resistant to picolinate auxins and not to 2,4-D and all contain lesions in the leucine rich F-box protein AFB5, this protein appears to be specifically involved in mediating the effects of picolinate auxins.

Figure 5:
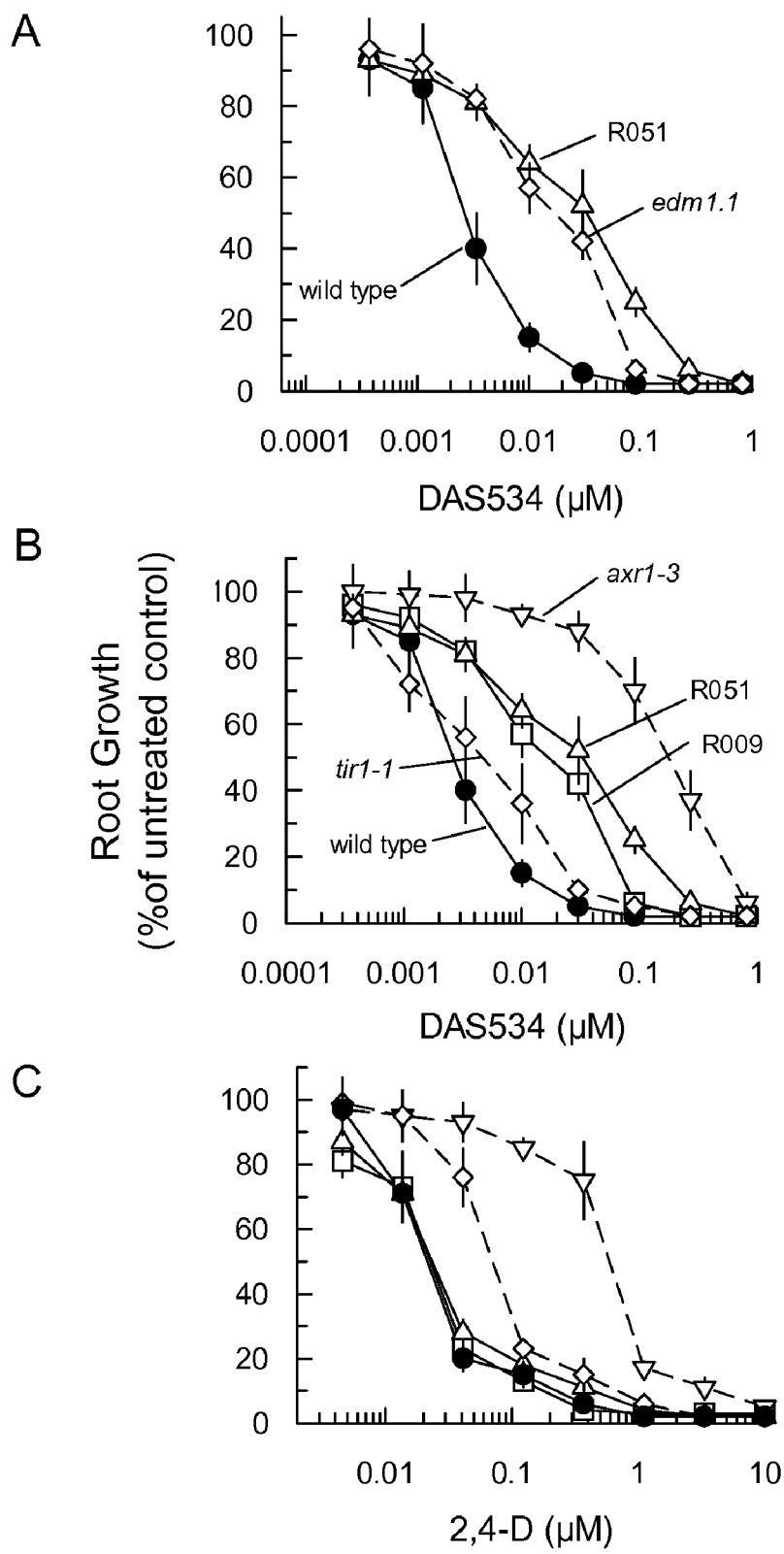
FIGS. 5A-5C. Comparison of the effect of DAS534 and 2,4-D on previously characterized mutants. Measurements were performed as described in FIG. 2. Typical root lengths for untreated controls were 20, 39 and 31 mm for tir1-1, axr2-1 and axr1-3 plants respectively.
Figure 6:
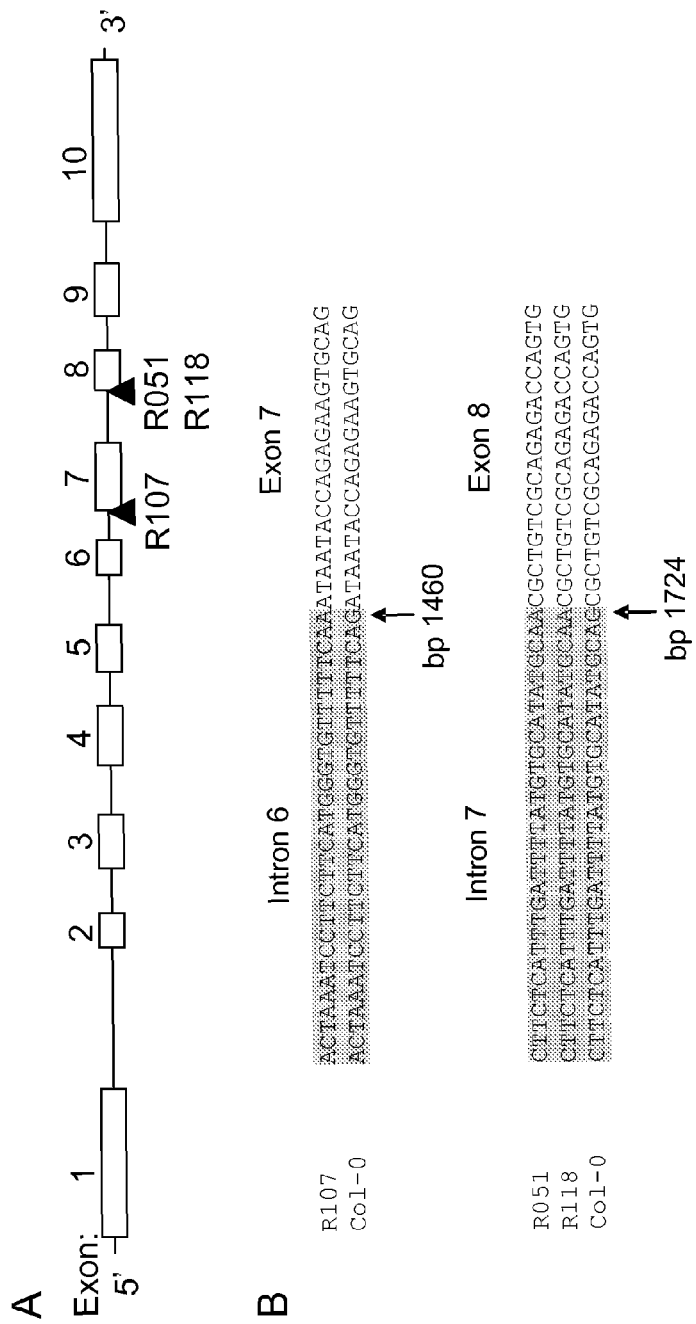
FIGS. 6A-6B. Mutation sites in the SGT1b (At4g11260) gene that confer resistance to DAS534.

The R051 mutation was mapped to a 100 kb interval on chromosome 4 around 36 cM between markers C4_36 and C4_37 (FIG. 3). This interval contains 17 genes including At4g11260 which encodes the tetratricopeptide-repeat containing protein, SGT1b (SEQ ID NO: 4). A mutation in SGT1b has recently been shown to enhance the level of resistance to 2,4-D in the tir1 mutant background (Gray et al., Plant Cell 15: 1310-1319, 2003). The deletion mutant line edm1 lacks seven genes (At4g11220 through At4g11280) including SGT1b (Tor et al., Plant Cell 14: 993-1003, 2002). We found that this deletion mutant had a similar level of resistance to DAS534 as the Group 2 mutant R051 (FIG. 5A). It was also very cross-resistant to picloram (20-fold, data not shown) similar to the Group 2 mutants. To determine if the DAS534-resistant mutants in complementation Group 2 contained mutations in SGT1b, At4g11260 was PCR amplified from genomic DNA from all three of the mutants. Sequence analysis showed that all three mutants contained lesions producing alterations of the 3' intron splice sites of At4g11260. Mutants R051 and R118 contained G to A transitions that disrupt the 3' splice site of intron 7 whereas mutant R107 contained a G to A transition that disrupts the 3' splice site of intron 6 (FIG. 6).

To confirm that the mutations in At4g11260 were responsible for the DAS534-resistant phenotype, the mutant R051 was transformed with a construct containing the wild type At4g11260 gene driven by the constitutive CsVMV promoter (Verdaguer et al., Plant Mol Biol 37: 1055-1067, 1998). T2 seed were tested for DAS534 sensitivity. Using the same process as was employed for identification of AFB5 transformants, ten independent transformants were identified that were sensitive to DAS534 confirming that the lesions in At4g11260 are responsible for the resistance to DAS534. An example of a R051 line containing the transgene that restores sensitivity to DAS534 is shown in FIG. 2J.

EXAMPLE 4

Comparison of the Phenotypes of Picolinate Auxin Resistant Mutants with other Auxin Resistant Mutants The mutations presently identified in AFB5 and SGT1b conferring picolinate-selective resistance implicate the SCF ubiquitin ligase complex in the molecular mode of action of these herbicides. Several other mutants associated with this complex (e.g., tir1, axr1) or its ubiquitination targets (e.g., axr2) in the auxin response have been characterized and possess varying phenotypes and levels of resistance to 2,4-D or IAA (Leyser et al., Nature 364: 161-164, 1993; Ruegger et al., Genes Dev 12: 198-207, 1998; Nagpal et al., Plant Physiol 123: 563-573, 2000). However, their chemical resistance profile to picolinate auxins has not been previously established.

The mutant axr1-3 is defective in the rubinylation mechanism required to activate SCF complexes. This mutant had a high level of resistance to DAS534 as well as to 2,4-D (FIG. 5B and 5C) and so there was no indication of significant chemical selectivity between these two auxin classes in this mutant. The axr1-3 mutant was also very resistant to picloram (160-fold). The relative degree of resistance of axr1-3 to the picolinate auxins was higher than that of Group 1 and Group 2 mutants indicating that this mutation has a more profound overall effect on auxinic responses. This is consistent with its general role in the activation of SCF complexes (Schwechheimer et al., Plant Cell. 14(10):2553-2563, 2002).

Mutants containing lesions in the F-box protein tir1 have significantly lower levels of resistance to 2,4-D than axr1 (FIG. 5C) suggesting that additional SCF complex components may also be involved in the 2,4-D response (Ruegger et al., Genes Dev 12: 198-207, 1998; Dharmasiri et al., Nature 435:441-445, 2005). It was presently found that the modest level of resistance of tir1-1 to DAS534 was approximately equivalent to that of 2,4-D thus the marked chemical selectivity observed with the Group 1 and 2 mutants was not apparent with this mutant. The tir1-1 mutant was slightly more resistant to picloram than DAS534 but this resistance is considerably less than the resistance of either Group 1 or Group 2 mutants to this compound. The resistance levels of tir1-1 and axr1-3 to 2,4-D in our study were similar to those previously described (Estelle & Somerville, Mol Gen Genet 206: 200-206, 1987; Ruegger et al., Genes Dev 12: 198-207, 1998), validating that the results from the subject assay system are comparable to previous work using slightly different assay methodologies.

AXR2 is one of the short-lived AUX/IAA transcriptional regulators targeted for SCF-mediated ubiquitination and mutations in these loci have been found to confer a dominant 2,4-D resistance phenotype (Wilson et al., Mol Gen Genet 222: 377-383, 1990; Nagpal et al., Plant Physiol 123: 563-573, 2000). The roots of axr2 are agravitropic and elongated relative to wild type, corresponding to a loss of auxin regulation. The level of resistance of axr2-1 to DAS534 was similar to that found with 2,4-D and picloram and so there was no marked chemical specificity in resistance.

In summary, none of the three previously described auxin-resistant mutants that were tested showed the differential pattern of no or low resistance to 2,4-D and high levels of resistance to picolinate auxins that we identified in the Group 1 and 2 mutants from our picolinate auxin resistance screen.

EXAMPLE 5

Resistance Phenotype of afb5 sgt1B Double Mutants

Mutations in either AFB5 or SGT1b cause similar levels of resistance to DAS534. Plants containing homozygous mutations in both AFB5 and SGT1b were generated to determine if the level of resistance to DAS534 was similar or increased over that of the single mutant lines. Genomic DNA was isolated from ninety-five F2 plants generated from a cross of R009 and R051. The At5g49980 (AFB5) and At4g11260 (SGT1b) genes were amplified by PCR and evaluated by DNA sequence analysis for mutations. Eight plants containing double mutations were identified and three of them were compared with the single mutant parental lines for resistance to DAS534, picloram and 2,4-D. The single and double mutants exhibited similar levels of resistance (5 to 10-fold, data not shown), thus the resistance mechanisms in afb5 and sgt1b are not additive. The double mutants also exhibited no obvious deleterious phenotype in growth or fertility, similar to the single mutants. These data therefore suggest that AFB5 and SGT1b are involved in the same response pathway to DAS534.

EXAMPLE 6

Functional Assay for AFB5

A biochemical pull-down assay to monitor the picolinate auxin-response of AFB5 is constructed using the methods described in Dharmasiri et al. (Curr. Biol. 13:1418-1422, 2003). However, plant extracts for the assays are made from transgenic *Arabidopsis* afb5 plants expressing myc-tagged AFB5 rather than tir1 plants expressing TIR1-myc. The recovery of AFB5-myc is monitored by immunoblotting with anti-c-myc antibody. Test compounds are added into the assay mixture and the reduction in recovery of AFB5-Myc is monitored.

EXAMPLE 7

Ligand-Binding Assay for AFB5

A biochemical assay to monitor ligand-binding by AFB5 is constructed using the methods described in Dharmasiri et al. (Nature 435:441-445, 2005) and Kepinski and Leyser (Nature, 435:446-451, 2005). However, plant extracts for the assays are made from transgenic *Arabidopsis* afb5 plants expressing myc-tagged AFB5 rather than tir1 plants expressing TIR1-myc. Also [$^3$H]-picloram, [$^3$ H]DAS534 or other tritiated picolinate auxin is used as the radioligand instead of [$^3$H]IAA or [$^3$ H]2,4-D. Test compounds are added into the assay mixture and the displacement of binding of tritiated picolinate auxin is monitored.

EXAMPLE 8

Sequence Comparisons and Identification of Additional Homologs

BLAST searches of the NCBI databases using the AtAFB5 sequence identified six AFBs in the *Arabidopsis* genome (AtTIR1, AtAFB1-5), 4 AFB homologs from the rice (*Oryza sativa*) genome, and a homolog of AFB5 from Populus. All of these sequences were aligned using CLUSTALW within the AlignX module of Vector NTI.

Figure 7:
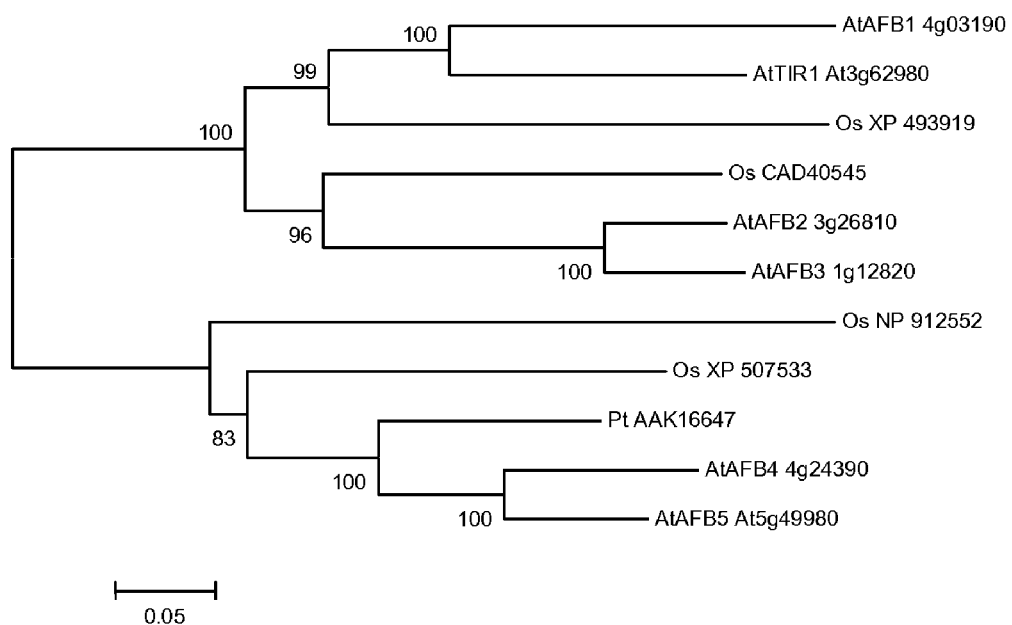
FIG. 7 illustrates a phylogenetic analysis showing that AFB5 (and four related AFBs, including AFB4) are distinct from previously characterized TIR1 (and six related proteins, including AFB1, AFB2, and AFB3). AtAFB1 4g03190 is gi|18412177, AtAFB2 3g26810 is gi|8405102, AtAFB3 1g12820 is gi|18391439, AtAFB4 4g24390 is gi|42573021, AtAFB5 At5g49980 is gi|18423092, AtTIR1 At3g62980 is gi|18412567, Os XP 493919 is gi|50949123, Os CAD40545 is gi|21740736, Os NP 912552 is gi|34902412, Os XP 507533 is gi|51979370 and Pt AAK16647 is gi|13249030.

From this CLUSTAL alignment, a phylogenetic analysis was performed using the neighbor-joining method in MEGA3.1 (S Kumar et al. (2004) Briefings in Bioinformatics 5:150-163) (% bootstrap values from 1000 iterations are shown). As illustrated in FIG. 7, this shows that AFB5, AFB4, and 4 other related AFBs (Os NP 912552, Os XP 507533, Pt AAK16647) are distinct from previously characterized TIR1 and 5 TIR1-related AFBs (AtAFB 1 4g03190, AtTIR1 At3g62980, Os XP 493919, Os CA D40545, AtAFB2 3g26810, and AtAFB3 1g12820). Members of the TIR1 group share at least 42% amino acid identity with all other members of that group.

Across the entire proteins, AFB4 and AFB5 share about 80% amino acid identity with each other. Members of the AFB4 and AFB5 group all have at least 54% identity with all other members of the group. The protein sequence from Populus has about 70% identity with AFB4 and about 73% identity with AFB5. All members of this group are considered to be within, and usable according to, the subject invention. The mRNA and protein sequences, respectively, of the four AFB5 homologs are attached as SEQ ID NOS: 7 and 8 (*Oryza sativa* (rice) (Genbank entry gi:3490241 1), SEQ ID NOS: 9 and 10 (*Oryza sativa* (rice) (Genbank entry gi:51979369), and SEQ ID NOS:11 and 12 (from Populus).

EXAMPLE 9

Resistance of AFB5 Mutant to Foliar Application of Picolinate Auxin Herbicides

Figure 8:
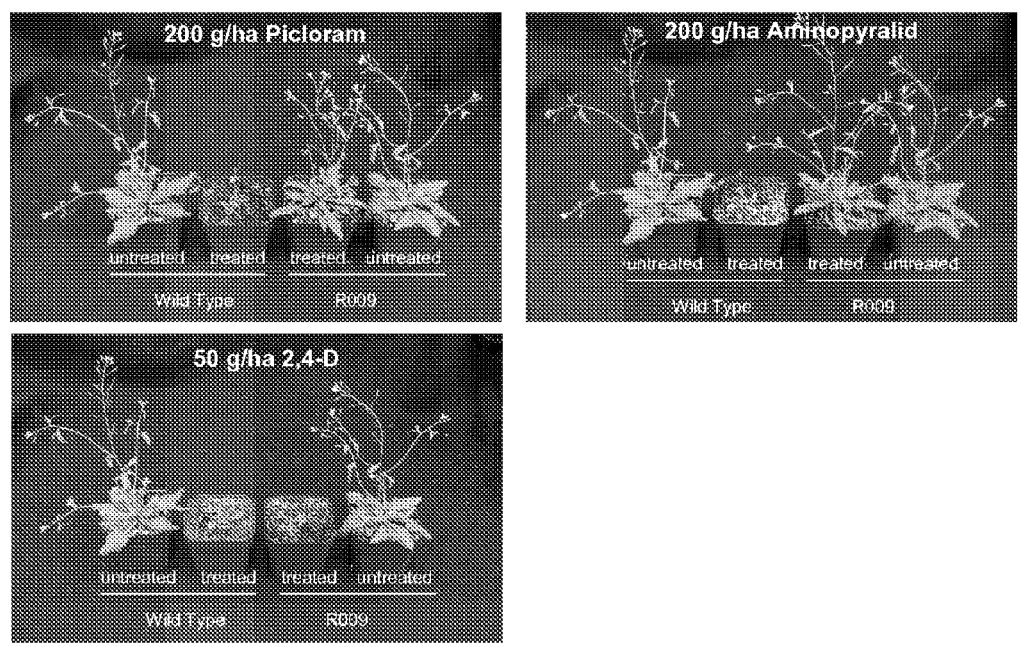
FIG. 8 shows a comparison of the effect of a foliar application of 200 g/ha picloram (A), 200 g/ha aminopyralid (B) or 50 g/ha 2,4-D (C) on wild type Col-0 and mutant R009 *Arabidopsis* plants. Pictures were taken 12 days after treatment of 17-day old plants.

*Arabidopsis* seedlings were grown for two weeks in a growth chamber (23° C.; continuous light at 120-150 µE m$^{-2}$ sec$^{-1}$), then taken to the greenhouse for three days after which plants were sprayed with herbicide using a track-sprayer to deliver the appropriate rate. Plants were then grown in the greenhouse for 12 days (22° C. under supplemented light with a 14 h: 10 h light-dark cycle) prior to photography and evaluation. A foliar spray application of picloram or aminopyralid at 200 g/ha on wild type Col-0 *Arabidopsis* plants growing in the greenhouse produced profound morphological effects and severely inhibited plant growth, whereas the applications had minimal effect on the Group 1 mutant R009 (FIG. 8). This is in contrast to the effect of 2,4-D which induces auxinic symptoms and growth reduction to a similar extent on both wild type and mutant plants at 50 g/ha. Thus the chemical selectivity of resistance seen in seedling plate assays is maintained in adult plants with foliar exposure to the auxin herbicides.

ADDITIONAL REFERENCES

Balko et al. (2003) Preparation of 6-aryl-4-aminopicolinic acids as herbicides with excellent crop selectivity. 2002-US24120: 84

Klein et al. (1987) High-velocity microprojectiles for delivering nucleic acids into living cells. Nature (London, United Kingdom) 327: 70-73

Smith et al. (1988) Antisense RNA inhibition of polygalacturonase gene expression in transgenic tomatoes. Nature (London, United Kingdom) 334: 724-726

We claim:

1. A transgenic plant having increased resistance to a picolinate auxin herbicide, as compared to a corresponding wild-type plant, wherein the transgenic plant comprises at least one characteristic selected from the group consisting of:
   a) the transgenic plant does not express wild-type AFB5 protein comprising at least 90% amino acid identity with the sequence of SEQ ID NO: 2, wherein the wild-type protein is expressed in the wild-type plant; and
   b) the resistance is due to inhibited expression of the wild-type AFB5 gene encoding the wild-type AFB5 protein comprising at least 90% amino acid identity with the sequence of SEQ ID NO: 2.

2. The transgenic plant of claim 1 wherein the wild-type AFB5 protein has at least 95% amino acid identity with the sequence of SEQ ID NO: 2.

3. A method of controlling weeds, the method comprising applying a picolinate auxin herbicide to a field, the field comprising at least one transgenic plant according to claim 1.

4. A transgenic seed produced by a transgenic plant according to claim 1.

5. A method of controlling weeds, the method comprising planting at least one seed according to claim 3 in the field, and applying a picolinate auxin herbicide to the field after planting the seed in the field.

6. The transgenic plant of claim 1 wherein the plant is a row crop.

7. The transgenic plant of claim 6, the transgenic plant selected from the group consisting of soybean (*Glycine max*), rapeseed and canola (including *Brassica napus* and *B. campestris*), sunflower (*Helianthus annuus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*), sorghum (*Sorghum bicolor*), and peanut (*Arachis hypogaea*).

8. The transgenic plant of claim 1 wherein the transgenic plant is selected from a fruit-bearing plant, a vegetable-bearing plant, a grain-producing plant, a nut-producing plant, a rapid cycling *Brassica species*, alfalfa (*Medicago sativa*), tobacco (*Nicotiana spp.*), turfgrass (Poaceae family), clover (*Trifolium spp.*), and forage crops.

9. The transgenic plant of claim 1 wherein the plant is selected from the group consisting of *Arabidopsis*, rice, and poplar.

10. The method of claim 5 wherein the herbicide comprises DAS534, picloram, aminopyralid, or clopyralid.

11. The transgenic plant of claim 1 wherein the expression is inhibited by a gene down-regulation mechanism.

12. The transgenic plant of claim 11 wherein the expression is inhibited by antisense RNA encoded by SEQ ID NO: 1 or a fragment thereof expressed in opposite orientation as compared to the wild-type gene.

13. The transgenic plant of claim 11 wherein the expression is inhibited by a nucleic acid molecule having a hairpin configuration, wherein the wild-type gene comprises a coding sequence, and the nucleic acid molecule having the hairpin configuration comprises all or part of the coding sequence cloned in sense and antisense orientations in a single transcription unit.

14. The transgenic plant of claim 11 wherein the transgenic plant further comprises an additional AFB5 gene, and the expression is inhibited by over-expression of the additional gene, which causes co-suppression of the wild-type AFB5 gene; and wherein production of the wild-type AFB5 protein is inhibited.

15. The transgenic plant of claim 12 wherein the plant comprises a dsRNA molecule effective for RNAi.

16. The transgenic plant of claim 14 wherein the plant comprises a dsRNA molecule effective for RNAi.

17. The transgenic plant of claim 1, wherein the wild-type AFB5 protein comprises the amino acid sequence of SEQ ID NO: 2.

* * * * *

UNITED STATES PATENT AND TRADEMARK OFFICE
CERTIFICATE OF CORRECTION

PATENT NO. : 7,820,883 B2                                                 Page 1 of 1
APPLICATION NO. : 11/686844
DATED : October 26, 2010
INVENTOR(S) : Walsh et al.

It is certified that error appears in the above-identified patent and that said Letters Patent is hereby corrected as shown below:

In the Claims:

In Claim 5 (Col. 77, line 35), "claim 3" should be --claim 4--.

Signed and Sealed this
Eighth Day of November, 2011

David J. Kappos
Director of the United States Patent and Trademark Office

SEQUENCE LISTING

<160> NUMBER OF SEQ ID NOS: 13

<210> SEQ ID NO 1
<211> LENGTH: 1860
<212> TYPE: DNA
<213> ORGANISM: Arabidopsis thaliana
<220> FEATURE:
<221> NAME/KEY: CDS

<222> LOCATION: (1)..(1860)

<400> SEQUENCE: 1

```
atg aca caa gat cgc tca gaa atg tct gaa gat gac gat gac caa caa      48
Met Thr Gln Asp Arg Ser Glu Met Ser Glu Asp Asp Asp Gln Gln
1               5                  10                  15 tct cca ccg ttg gat cta ccc tct acc gcc ata gct gat cct tgc tca      96
Ser Pro Pro Leu Asp Leu Pro Ser Thr Ala Ile Ala Asp Pro Cys Ser
            20                  25                  30 tct tcc tct tca cca aac aaa tct cgt aac tgt atc tca aat tct caa     144
Ser Ser Ser Ser Pro Asn Lys Ser Arg Asn Cys Ile Ser Asn Ser Gln
        35                  40                  45 act ttc cct gac cat gtt ctc gaa aac gta ctt gag aac gtt ctt cag     192
Thr Phe Pro Asp His Val Leu Glu Asn Val Leu Glu Asn Val Leu Gln
50                  55                  60 tta gat tca aga tgt gac cgt aac gct gct tct cta gtt tgc aaa         240
Phe Leu Asp Ser Arg Cys Asp Arg Asn Ala Ala Ser Leu Val Cys Lys
65                  70                  75                  80 tct tgg tgg cgt gtt gaa gct ttg act cga tct gag gtt ttt att ggt     288
Ser Trp Trp Arg Val Glu Ala Leu Thr Arg Ser Glu Val Phe Ile Gly
                85                  90                  95 aac tgt tac gct ctt tct ccg gcg agg ttg act cag aga ttc aag cgt     336
Asn Cys Tyr Ala Leu Ser Pro Ala Arg Leu Thr Gln Arg Phe Lys Arg
            100                 105                 110 gtt agg tct ctt gtg ctg aaa ggg aaa cct agg ttt gct gat ttc aat     384
Val Arg Ser Leu Val Leu Lys Gly Lys Pro Arg Phe Ala Asp Phe Asn
        115                 120                 125 ctc atg cct cct gat tgg ggt gct aat ttt gct cct tgg gtt tct act     432
Leu Met Pro Pro Asp Trp Gly Ala Asn Phe Ala Pro Trp Val Ser Thr
130                 135                 140 atg gct caa gct tat cct tgt ctt gag aaa gtt gat ttg aag agg atg     480
Met Ala Gln Ala Tyr Pro Cys Leu Glu Lys Val Asp Leu Lys Arg Met
145                 150                 155                 160 ttt gtt act gat gat gat tta gct ctt ctt gct gac tct ttt cct ggg     528
Phe Val Thr Asp Asp Asp Leu Ala Leu Leu Ala Asp Ser Phe Pro Gly
                165                 170                 175 ttt aaa gag ctt atc ttg gtt tgt tgt gaa ggt ttt ggt act agt ggt     576
Phe Lys Glu Leu Ile Leu Val Cys Cys Glu Gly Phe Gly Thr Ser Gly
            180                 185                 190 atc tct att gtt gcc aac aag tgc aga aag ctg aaa gtg ctt gat ttg     624
Ile Ser Ile Val Ala Asn Lys Cys Arg Lys Leu Lys Val Leu Asp Leu
        195                 200                 205 att gag tct gag gtc acg gat gat gaa gtg gat tgg atc tct tgt ttc     672
Ile Glu Ser Glu Val Thr Asp Asp Glu Val Asp Trp Ile Ser Cys Phe
210                 215                 220 cct gag gat gta act tgt ttg gag tct tta gct ttt gac tgt gtg gaa     720
Pro Glu Asp Val Thr Cys Leu Glu Ser Leu Ala Phe Asp Cys Val Glu
225                 230                 235                 240 gct cct atc aat ttt aag gcg ctt gag ggt ctt gtt gct agg tca ccg     768
Ala Pro Ile Asn Phe Lys Ala Leu Glu Gly Leu Val Ala Arg Ser Pro
                245                 250                 255 ttc ttg aag aaa ctt agg cta aac agg ttt gtg tct ctt gtg gag cta     816
Phe Leu Lys Lys Leu Arg Leu Asn Arg Phe Val Ser Leu Val Glu Leu
            260                 265                 270 cat cgt ctg cta ctt gga gct cca cag ctt act agt ctt ggg act ggt     864
His Arg Leu Leu Leu Gly Ala Pro Gln Leu Thr Ser Leu Gly Thr Gly
        275                 280                 285 tca ttt agc cat gat gag gaa cct cag agt gag caa gaa cca gat tat     912
Ser Phe Ser His Asp Glu Glu Pro Gln Ser Glu Gln Glu Pro Asp Tyr
290                 295                 300
```

```
gct gct gca ttt cgt gct tgt aaa tct gta gtt tgc ttg tca ggg ttt      960
Ala Ala Ala Phe Arg Ala Cys Lys Ser Val Val Cys Leu Ser Gly Phe
305                 310                 315                 320 aga gag ttg atg ccg gag tat ctt cca gct atc ttt ccg gtg tgc gct     1008
Arg Glu Leu Met Pro Glu Tyr Leu Pro Ala Ile Phe Pro Val Cys Ala
                325                 330                 335 aat ctc acc tcc ctg aac ttc agt tat gct aac att tct cct gac atg     1056
Asn Leu Thr Ser Leu Asn Phe Ser Tyr Ala Asn Ile Ser Pro Asp Met
            340                 345                 350 ttc aag ccc atc ata ctc aat tgc cac aaa ctc cag gtg ttc tgg gcc     1104
Phe Lys Pro Ile Ile Leu Asn Cys His Lys Leu Gln Val Phe Trp Ala
        355                 360                 365 ctt gat tca ata tgt gat gaa gga cta cag gca gtt gca gcc act tgc     1152
Leu Asp Ser Ile Cys Asp Glu Gly Leu Gln Ala Val Ala Ala Thr Cys
    370                 375                 380 aag gaa ctc cgt gaa ctc agg atc ttc cct ttt gat cct cgg gaa gac     1200
Lys Glu Leu Arg Glu Leu Arg Ile Phe Pro Phe Asp Pro Arg Glu Asp
385                 390                 395                 400 agt gaa ggt cct gtc tct gaa tta ggc ctc caa gca atc tcc gag ggt     1248
Ser Glu Gly Pro Val Ser Glu Leu Gly Leu Gln Ala Ile Ser Glu Gly
                405                 410                 415 tgt agg aaa cta gaa tct att ctc tac ttt tgc cag cgc atg act aat     1296
Cys Arg Lys Leu Glu Ser Ile Leu Tyr Phe Cys Gln Arg Met Thr Asn
            420                 425                 430 gcc gct gtg ata gcc atg tca gag aac tgt cca gag ctt act gtg ttt     1344
Ala Ala Val Ile Ala Met Ser Glu Asn Cys Pro Glu Leu Thr Val Phe
        435                 440                 445 agg ctg tgc ata atg ggt cga cat agg cct gac cat gta aca gga aag     1392
Arg Leu Cys Ile Met Gly Arg His Arg Pro Asp His Val Thr Gly Lys
    450                 455                 460 cct atg gac gag gga ttt ggt gcc att gtt aaa aac tgc aag aag cta     1440
Pro Met Asp Glu Gly Phe Gly Ala Ile Val Lys Asn Cys Lys Lys Leu
465                 470                 475                 480 act cgc ctt gca gtg tcg gga ttg ctg aca gat caa gct ttt agg tat     1488
Thr Arg Leu Ala Val Ser Gly Leu Leu Thr Asp Gln Ala Phe Arg Tyr
                485                 490                 495 atg ggt gag tat ggg aaa ttg gtc cgt acg ctt tca gta gct ttt gca     1536
Met Gly Glu Tyr Gly Lys Leu Val Arg Thr Leu Ser Val Ala Phe Ala
            500                 505                 510 ggg gac agt gac atg gct ctg aga cat gtc cta gaa ggt tgc cct aga     1584
Gly Asp Ser Asp Met Ala Leu Arg His Val Leu Glu Gly Cys Pro Arg
        515                 520                 525 ctg cag aaa ctt gag ata agg gac agt ccc ttt gga gat gtt gca tta     1632
Leu Gln Lys Leu Glu Ile Arg Asp Ser Pro Phe Gly Asp Val Ala Leu
    530                 535                 540 cgg tct ggt atg cat cgc tat tac aac atg agg ttt gtt tgg atg tca     1680
Arg Ser Gly Met His Arg Tyr Tyr Asn Met Arg Phe Val Trp Met Ser
545                 550                 555                 560 gca tgt agc ttg tct aag gga tgc tgc aag gat att gca cga gca atg     1728
Ala Cys Ser Leu Ser Lys Gly Cys Cys Lys Asp Ile Ala Arg Ala Met
                565                 570                 575 ccg aat cta gtt gtg gaa gta att gga tcg gat gat gat gat gac aat     1776
Pro Asn Leu Val Val Glu Val Ile Gly Ser Asp Asp Asp Asp Asp Asn
            580                 585                 590 agg gat tat gtc gag act tta tac atg tat cgg tct ctt gat ggt cca     1824
Arg Asp Tyr Val Glu Thr Leu Tyr Met Tyr Arg Ser Leu Asp Gly Pro
        595                 600                 605 agg aat gat gca cca aag ttc gtc acg att tta tag                     1860
Arg Asn Asp Ala Pro Lys Phe Val Thr Ile Leu
```

610                 615

<210> SEQ ID NO 2
<211> LENGTH: 619
<212> TYPE: PRT
<213> ORGANISM: Arabidopsis thaliana

<400> SEQUENCE: 2

Met Thr Gln Asp Arg Ser Glu Met Ser Glu Asp Asp Asp Gln Gln
1               5                   10                  15

Ser Pro Pro Leu Asp Leu Pro Ser Thr Ala Ile Ala Asp Pro Cys Ser
                20                  25                  30

Ser Ser Ser Ser Pro Asn Lys Ser Arg Asn Cys Ile Ser Asn Ser Gln
            35                  40                  45

Thr Phe Pro Asp His Val Leu Glu Asn Val Leu Glu Asn Val Leu Gln
    50                  55                  60

Phe Leu Asp Ser Arg Cys Asp Arg Asn Ala Ala Ser Leu Val Cys Lys
65              70                  75                  80

Ser Trp Trp Arg Val Glu Ala Leu Thr Arg Ser Glu Val Phe Ile Gly
                85                  90                  95

Asn Cys Tyr Ala Leu Ser Pro Ala Arg Leu Thr Gln Arg Phe Lys Arg
                100                 105                 110

Val Arg Ser Leu Val Leu Lys Gly Lys Pro Arg Phe Ala Asp Phe Asn
                115                 120                 125

Leu Met Pro Pro Asp Trp Gly Ala Asn Phe Ala Pro Trp Val Ser Thr
    130                 135                 140

Met Ala Gln Ala Tyr Pro Cys Leu Glu Lys Val Asp Leu Lys Arg Met
145                 150                 155                 160

Phe Val Thr Asp Asp Asp Leu Ala Leu Leu Ala Asp Ser Phe Pro Gly
                165                 170                 175

Phe Lys Glu Leu Ile Leu Val Cys Cys Glu Gly Phe Gly Thr Ser Gly
                180                 185                 190

Ile Ser Ile Val Ala Asn Lys Cys Arg Lys Leu Lys Val Leu Asp Leu
            195                 200                 205

Ile Glu Ser Glu Val Thr Asp Asp Glu Val Asp Trp Ile Ser Cys Phe
    210                 215                 220

Pro Glu Asp Val Thr Cys Leu Glu Ser Leu Ala Phe Asp Cys Val Glu
225                 230                 235                 240

Ala Pro Ile Asn Phe Lys Ala Leu Glu Gly Leu Val Ala Arg Ser Pro
                245                 250                 255

Phe Leu Lys Lys Leu Arg Leu Asn Arg Phe Val Ser Leu Val Glu Leu
                260                 265                 270

His Arg Leu Leu Leu Gly Ala Pro Gln Leu Thr Ser Leu Gly Thr Gly
            275                 280                 285

Ser Phe Ser His Asp Glu Glu Pro Gln Ser Gln Glu Pro Asp Tyr
    290                 295                 300

Ala Ala Ala Phe Arg Ala Cys Lys Ser Val Val Cys Leu Ser Gly Phe
305                 310                 315                 320

Arg Glu Leu Met Pro Glu Tyr Leu Pro Ala Ile Phe Pro Val Cys Ala
                325                 330                 335

Asn Leu Thr Ser Leu Asn Phe Ser Tyr Ala Asn Ile Ser Pro Asp Met
                340                 345                 350

Phe Lys Pro Ile Ile Leu Asn Cys His Lys Leu Gln Val Phe Trp Ala
            355                 360                 365

```
Leu Asp Ser Ile Cys Asp Glu Gly Leu Gln Ala Val Ala Thr Cys
    370             375                 380

Lys Glu Leu Arg Glu Leu Arg Ile Phe Pro Phe Asp Pro Arg Glu Asp
385                 390                 395                 400

Ser Glu Gly Pro Val Ser Glu Leu Gly Leu Gln Ala Ile Ser Glu Gly
                405                 410                 415

Cys Arg Lys Leu Glu Ser Ile Leu Tyr Phe Cys Gln Arg Met Thr Asn
            420                 425                 430

Ala Ala Val Ile Ala Met Ser Glu Asn Cys Pro Glu Leu Thr Val Phe
        435                 440                 445

Arg Leu Cys Ile Met Gly Arg His Arg Pro Asp His Val Thr Gly Lys
    450                 455                 460

Pro Met Asp Glu Gly Phe Gly Ala Ile Val Lys Asn Cys Lys Lys Leu
465                 470                 475                 480

Thr Arg Leu Ala Val Ser Gly Leu Leu Thr Asp Gln Ala Phe Arg Tyr
                485                 490                 495

Met Gly Glu Tyr Gly Lys Leu Val Arg Thr Leu Ser Val Ala Phe Ala
            500                 505                 510

Gly Asp Ser Asp Met Ala Leu Arg His Val Leu Glu Gly Cys Pro Arg
        515                 520                 525

Leu Gln Lys Leu Glu Ile Arg Asp Ser Pro Phe Gly Asp Val Ala Leu
    530                 535                 540

Arg Ser Gly Met His Arg Tyr Tyr Asn Met Arg Phe Val Trp Met Ser
545                 550                 555                 560

Ala Cys Ser Leu Ser Lys Gly Cys Cys Lys Asp Ile Ala Arg Ala Met
                565                 570                 575

Pro Asn Leu Val Val Glu Val Ile Gly Ser Asp Asp Asp Asp Asp Asn
            580                 585                 590

Arg Asp Tyr Val Glu Thr Leu Tyr Met Tyr Arg Ser Leu Asp Gly Pro
        595                 600                 605

Arg Asn Asp Ala Pro Lys Phe Val Thr Ile Leu
    610                 615

<210> SEQ ID NO 3
<211> LENGTH: 1290
<212> TYPE: DNA
<213> ORGANISM: Arabidopsis thaliana
<220> FEATURE:
<221> NAME/KEY: CDS
<222> LOCATION: (1)..(1074)

<400> SEQUENCE: 3 atg gcc aag gaa tta gca gag aaa gct aaa gaa gct ttt cta gat gat      48
Met Ala Lys Glu Leu Ala Glu Lys Ala Lys Glu Ala Phe Leu Asp Asp
1               5                   10                  15 gac ttc gat gtt gct gtt gac tta tac tcc aaa gcc att gac ttg gat      96
Asp Phe Asp Val Ala Val Asp Leu Tyr Ser Lys Ala Ile Asp Leu Asp
            20                  25                  30 ccc aat tgc gcc gcc ttc ttc gcc gat cgt gct cag gcc aac atc aaa     144
Pro Asn Cys Ala Ala Phe Phe Ala Asp Arg Ala Gln Ala Asn Ile Lys
        35                  40                  45 atc gat aac ttc act gaa gct gtt gta gat gcg aac aaa gcc att gag     192
Ile Asp Asn Phe Thr Glu Ala Val Val Asp Ala Asn Lys Ala Ile Glu
    50                  55                  60 ttg gag cca acg ttg gca aaa gcc tat ctc aga aag ggc act gct tgt     240
Leu Glu Pro Thr Leu Ala Lys Ala Tyr Leu Arg Lys Gly Thr Ala Cys
65                  70                  75                  80
```

-continued

| | |
|---|---|
| atg aag cta gaa gaa tat agt act gct aaa gca gcc ctg gaa aag gga<br>Met Lys Leu Glu Glu Tyr Ser Thr Ala Lys Ala Ala Leu Glu Lys Gly<br>                     85                     90                    95 | 288 |
| gct tct gtt gca ccg aat gaa cca aag ttt aag aag atg ata gat gaa<br>Ala Ser Val Ala Pro Asn Glu Pro Lys Phe Lys Lys Met Ile Asp Glu<br>        100                  105                  110 | 336 |
| tgc gat ctt cgt att gca gaa gaa gag aaa gat ttg gtt cag ccg atg<br>Cys Asp Leu Arg Ile Ala Glu Glu Glu Lys Asp Leu Val Gln Pro Met<br>       115                  120                  125 | 384 |
| cca ccg agt ttg cct tca agc tct aca aca cca cta gca acg gaa gct<br>Pro Pro Ser Leu Pro Ser Ser Ser Thr Thr Pro Leu Ala Thr Glu Ala<br>130                    135                  140 | 432 |
| gat gct cct cct gtt cca att cct gca gca cct gcc aaa ccg atg ttc<br>Asp Ala Pro Pro Val Pro Ile Pro Ala Ala Pro Ala Lys Pro Met Phe<br>145                    150                  155                  160 | 480 |
| agg cac gag ttc tac cag aaa cca gaa gaa gcg gtg gtg aca att ttc<br>Arg His Glu Phe Tyr Gln Lys Pro Glu Glu Ala Val Val Thr Ile Phe<br>                      165                  170                  175 | 528 |
| gcc aaa aaa gta cct aag gag aac gta act gtc gag ttt ggt gag cag<br>Ala Lys Lys Val Pro Lys Glu Asn Val Thr Val Glu Phe Gly Glu Gln<br>                    180                  185                  190 | 576 |
| att ctg agt gtt gtc att gat gtt gct gga gag gaa gct tat cat ctc<br>Ile Leu Ser Val Val Ile Asp Val Ala Gly Glu Glu Ala Tyr His Leu<br>            195                  200                  205 | 624 |
| cag ccg aga ttg ttc ggg aag ata ata cca gag aag tgc aga ttt gaa<br>Gln Pro Arg Leu Phe Gly Lys Ile Ile Pro Glu Lys Cys Arg Phe Glu<br>          210                  215                  220 | 672 |
| gta ttg tcg acc aaa gtt gag atc cgt ctt gcg aaa gca gag ata atc<br>Val Leu Ser Thr Lys Val Glu Ile Arg Leu Ala Lys Ala Glu Ile Ile<br>225                    230                  235                  240 | 720 |
| acc tgg gcc tcc ctt gaa tat ggt aaa ggg caa agt gtt ttg ccc aaa<br>Thr Trp Ala Ser Leu Glu Tyr Gly Lys Gly Gln Ser Val Leu Pro Lys<br>                    245                  250                  255 | 768 |
| ccc aat gtc tca tca gcg ctg tcg cag aga cca gtg tac cca tct tct<br>Pro Asn Val Ser Ser Ala Leu Ser Gln Arg Pro Val Tyr Pro Ser Ser<br>              260                  265                  270 | 816 |
| aag cca gca aaa gac tgg gac aag ttg gaa gct gaa gtg aag aaa cag<br>Lys Pro Ala Lys Asp Trp Asp Lys Leu Glu Ala Glu Val Lys Lys Gln<br>       275                  280                  285 | 864 |
| gag aag gat gag aag ctt gat gga gat gca gct atg aac aaa ttt ttc<br>Glu Lys Asp Glu Lys Leu Asp Gly Asp Ala Ala Met Asn Lys Phe Phe<br>290                    295                  300 | 912 |
| agc gac ata tac tcg agt gca gat gaa gac atg agg cgg gca atg aac<br>Ser Asp Ile Tyr Ser Ser Ala Asp Glu Asp Met Arg Arg Ala Met Asn<br>305                    310                  315                  320 | 960 |
| aaa tca ttt gca gag tcg aat ggg acg gta ctg tcg aca aac tgg aaa<br>Lys Ser Phe Ala Glu Ser Asn Gly Thr Val Leu Ser Thr Asn Trp Lys<br>                    325                  330                  335 | 1008 |
| gaa gtt ggg act aag aaa gtg gag agc act cca cca gat ggc atg gag<br>Glu Val Gly Thr Lys Lys Val Glu Ser Thr Pro Pro Asp Gly Met Glu<br>              340                  345                  350 | 1056 |
| ctc aag aag tgg gag tat tgatcttctt aaaatcccct tttctggttt<br>Leu Lys Lys Trp Glu Tyr<br>       355 | 1104 |
| ttgttaaaaa aaagtctgac aaatcttttg aactttaag gtgttttttt tttttggttt | 1164 |
| ctgctcgaat ttgtctctct ccattcttgc gttgtggtct caaagaacgt tctgatactt | 1224 |
| tgattttgta ttagaaaact aaaactcgca agtctgttgt tttggaaaaa aaaaaaaaaa | 1284 |
| aaaaaa | 1290 |

<210> SEQ ID NO 4
<211> LENGTH: 358
<212> TYPE: PRT
<213> ORGANISM: Arabidopsis thaliana

<400> SEQUENCE: 4

Met Ala Lys Glu Leu Ala Glu Lys Ala Lys Glu Ala Phe Leu Asp Asp
1               5                   10                  15

Asp Phe Asp Val Ala Val Asp Leu Tyr Ser Lys Ala Ile Asp Leu Asp
                20                  25                  30

Pro Asn Cys Ala Ala Phe Phe Ala Asp Arg Ala Gln Ala Asn Ile Lys
            35                  40                  45

Ile Asp Asn Phe Thr Glu Ala Val Val Asp Ala Asn Lys Ala Ile Glu
50                  55                  60

Leu Glu Pro Thr Leu Ala Lys Ala Tyr Leu Arg Lys Gly Thr Ala Cys
65                  70                  75                  80

Met Lys Leu Glu Glu Tyr Ser Thr Ala Lys Ala Ala Leu Glu Lys Gly
                85                  90                  95

Ala Ser Val Ala Pro Asn Glu Pro Lys Phe Lys Met Ile Asp Glu
            100                 105                 110

Cys Asp Leu Arg Ile Ala Glu Glu Lys Asp Leu Val Gln Pro Met
            115                 120                 125

Pro Pro Ser Leu Pro Ser Ser Thr Thr Pro Leu Ala Thr Glu Ala
            130                 135                 140

Asp Ala Pro Pro Val Pro Ile Pro Ala Ala Pro Ala Lys Pro Met Phe
145                 150                 155                 160

Arg His Glu Phe Tyr Gln Lys Pro Glu Glu Ala Val Val Thr Ile Phe
                165                 170                 175

Ala Lys Lys Val Pro Lys Glu Asn Val Thr Val Glu Phe Gly Glu Gln
            180                 185                 190

Ile Leu Ser Val Val Ile Asp Val Ala Gly Glu Glu Ala Tyr His Leu
            195                 200                 205

Gln Pro Arg Leu Phe Gly Lys Ile Ile Pro Glu Lys Cys Arg Phe Glu
210                 215                 220

Val Leu Ser Thr Lys Val Glu Ile Arg Leu Ala Lys Ala Glu Ile Ile
225                 230                 235                 240

Thr Trp Ala Ser Leu Glu Tyr Gly Lys Gly Gln Ser Val Leu Pro Lys
                245                 250                 255

Pro Asn Val Ser Ser Ala Leu Ser Gln Arg Pro Val Tyr Pro Ser Ser
            260                 265                 270

Lys Pro Ala Lys Asp Trp Asp Lys Leu Glu Ala Glu Val Lys Lys Gln
            275                 280                 285

Glu Lys Asp Glu Lys Leu Asp Gly Asp Ala Ala Met Asn Lys Phe Phe
290                 295                 300

Ser Asp Ile Tyr Ser Ser Ala Asp Glu Asp Met Arg Arg Ala Met Asn
305                 310                 315                 320

Lys Ser Phe Ala Glu Ser Asn Gly Thr Val Leu Ser Thr Asn Trp Lys
                325                 330                 335

Glu Val Gly Thr Lys Lys Val Ser Thr Pro Pro Asp Gly Met Glu
            340                 345                 350

Leu Lys Lys Trp Glu Tyr
        355

```
<210> SEQ ID NO 5
<211> LENGTH: 2554
<212> TYPE: DNA
<213> ORGANISM: Arabidopsis thaliana
<220> FEATURE:
<221> NAME/KEY: CDS
<222> LOCATION: (152)..(2023)

<400> SEQUENCE: 5
gagagagtcc aaacaccaag accagctcct ttttcaccta tctctcttct tcatctgaat      60
cagattttgt atcagaaaga gagcacctga gctcataaat tctggataag atcaaagtca     120
gagtctttct tgttttcat cacttacttg t atg aca gaa gaa gat agc tca         172
                                  Met Thr Glu Glu Asp Ser Ser
                                   1               5 gct aaa atg tca gag gat gtt gag aaa tat ctc aac tta aat cca cct       220
Ala Lys Met Ser Glu Asp Val Glu Lys Tyr Leu Asn Leu Asn Pro Pro
         10                  15                  20 tgc tcc tcc tcc tcc tct tct tcc tcc gcc gct aca ttc acg aac aag       268
Cys Ser Ser Ser Ser Ser Ser Ser Ser Ala Ala Thr Phe Thr Asn Lys
 25                  30                  35 tct cga aat ttc aaa tct tct ccc ccg ccg tgt cca gat cat gtc ctt       316
Ser Arg Asn Phe Lys Ser Ser Pro Pro Pro Cys Pro Asp His Val Leu
 40                  45                  50                  55 gag aac gtt tta gag aac gtg ctt cag ttc ctc act tcc aga tgc gat       364
Glu Asn Val Leu Glu Asn Val Leu Gln Phe Leu Thr Ser Arg Cys Asp
                 60                  65                  70 cgc aac gca gtc tca ttg gtc tgc aga tcg tgg tat cgc gtc gag gct       412
Arg Asn Ala Val Ser Leu Val Cys Arg Ser Trp Tyr Arg Val Glu Ala
             75                  80                  85 cag act cga tta gag gtt ttt att gga aac tgt tac tcg ctc tct cct       460
Gln Thr Arg Leu Glu Val Phe Ile Gly Asn Cys Tyr Ser Leu Ser Pro
         90                  95                 100 gct cgg ctt att cac cgg ttc aag cgt gtt agg tct ctt gtg ctt aaa       508
Ala Arg Leu Ile His Arg Phe Lys Arg Val Arg Ser Leu Val Leu Lys
    105                 110                 115 ggg aaa cct agg ttt gct gat ttt aat ctc atg cct cct aat tgg gga       556
Gly Lys Pro Arg Phe Ala Asp Phe Asn Leu Met Pro Pro Asn Trp Gly
120                 125                 130                 135 gct caa ttc tct cct tgg gtt gct gct aca gct aag gct tat cct tgg       604
Ala Gln Phe Ser Pro Trp Val Ala Ala Thr Ala Lys Ala Tyr Pro Trp
                140                 145                 150 ctc gag aag gtt cat ttg aag cgt atg ttt gtt acg gat gat gat ttg       652
Leu Glu Lys Val His Leu Lys Arg Met Phe Val Thr Asp Asp Asp Leu
            155                 160                 165 gct ctt ctt gct gag tcg ttt cct ggg ttc aaa gag ctt act ttg gtc       700
Ala Leu Leu Ala Glu Ser Phe Pro Gly Phe Lys Glu Leu Thr Leu Val
        170                 175                 180 tgc tgt gaa ggt ttt ggg act agt ggt att gct att gtt gct aac aaa       748
Cys Cys Glu Gly Phe Gly Thr Ser Gly Ile Ala Ile Val Ala Asn Lys
    185                 190                 195 tgc agg cag cta aag gtc ctt gat ttg atg gag tca gaa gtc aca gat       796
Cys Arg Gln Leu Lys Val Leu Asp Leu Met Glu Ser Glu Val Thr Asp
200                 205                 210                 215 gat gag ttg gat tgg att tct tgt ttt cct gag ggt gaa act cat ctg       844
Asp Glu Leu Asp Trp Ile Ser Cys Phe Pro Glu Gly Glu Thr His Leu
                220                 225                 230 gag tct ttg tct ttt gac tgt gtt gaa tcc cct atc aat ttc aag gca       892
Glu Ser Leu Ser Phe Asp Cys Val Glu Ser Pro Ile Asn Phe Lys Ala
            235                 240                 245 ttg gag gag ctc gtg gtt agg tca cca ttc ttg aag aaa ctt aga acg       940
```

```
                Leu Glu Glu Leu Val Val Arg Ser Pro Phe Leu Lys Lys Leu Arg Thr
                        250                 255                 260 aac agg ttt gtt tcc ctt gaa gag ctg cat cga cta atg gtt cga gcg       988
Asn Arg Phe Val Ser Leu Glu Glu Leu His Arg Leu Met Val Arg Ala
        265                 270                 275 ccg cag tta acg agt ctt ggg acg ggg tca ttt agt cca gac aat gtg      1036
Pro Gln Leu Thr Ser Leu Gly Thr Gly Ser Phe Ser Pro Asp Asn Val
280                 285                 290                 295 cct cag gga gaa caa caa ccg gat tat gca gct gct ttt cgt gct tgt      1084
Pro Gln Gly Glu Gln Gln Pro Asp Tyr Ala Ala Ala Phe Arg Ala Cys
                    300                 305                 310 aaa tcc ata gtt tgt ctc tca gga ttc agg gaa ttt aga ccg gaa tac      1132
Lys Ser Ile Val Cys Leu Ser Gly Phe Arg Glu Phe Arg Pro Glu Tyr
        315                 320                 325 ctc cta gcc atc tct tca gtt tgt gct aat ctc acc tct ctt aac ttc      1180
Leu Leu Ala Ile Ser Ser Val Cys Ala Asn Leu Thr Ser Leu Asn Phe
        330                 335                 340 agt tat gct aac att tct cct cac atg ctc aag ccc atc ata agc aac      1228
Ser Tyr Ala Asn Ile Ser Pro His Met Leu Lys Pro Ile Ile Ser Asn
345                 350                 355 tgt cac aat atc cga gtc ttc tgg gct ctt gac tcg ata cgt gat gaa      1276
Cys His Asn Ile Arg Val Phe Trp Ala Leu Asp Ser Ile Arg Asp Glu
360                 365                 370                 375 gga cta cag gca gtg gct gcc aca tgc aag gag ctc cgt gag ctt cgg      1324
Gly Leu Gln Ala Val Ala Ala Thr Cys Lys Glu Leu Arg Glu Leu Arg
                    380                 385                 390 att ttc cct ttt gat cct cgt gaa gac agt gaa ggt cct gtc tcg gga      1372
Ile Phe Pro Phe Asp Pro Arg Glu Asp Ser Glu Gly Pro Val Ser Gly
                395                 400                 405 gta ggc ctc caa gca att tca gag ggc tgt agg aaa ctg gaa tct atc      1420
Val Gly Leu Gln Ala Ile Ser Glu Gly Cys Arg Lys Leu Glu Ser Ile
        410                 415                 420 ctg tac ttt tgc cag aat atg acc aat gga gct gtg aca gcc atg tcg      1468
Leu Tyr Phe Cys Gln Asn Met Thr Asn Gly Ala Val Thr Ala Met Ser
        425                 430                 435 gag aac tgc ccg cag ctt act gtg ttt aga ctt tgc ata atg ggt cgc      1516
Glu Asn Cys Pro Gln Leu Thr Val Phe Arg Leu Cys Ile Met Gly Arg
440                 445                 450                 455 cat agg cct gac cac gtg aca gga aag cca atg gac gat gga ttt ggt      1564
His Arg Pro Asp His Val Thr Gly Lys Pro Met Asp Asp Gly Phe Gly
                    460                 465                 470 gcc att gtt aaa aac tgc aag aag cta acc cga ctt gca gta tca ggg      1612
Ala Ile Val Lys Asn Cys Lys Lys Leu Thr Arg Leu Ala Val Ser Gly
                475                 480                 485 tta cta aca gat gaa gct ttt agc tat ata gga gaa tat ggg aaa ttg      1660
Leu Leu Thr Asp Glu Ala Phe Ser Tyr Ile Gly Glu Tyr Gly Lys Leu
        490                 495                 500 atc cgt acg cta tct gta gcg ttt gct ggg aac agt gac aag gct ctg      1708
Ile Arg Thr Leu Ser Val Ala Phe Ala Gly Asn Ser Asp Lys Ala Leu
        505                 510                 515 aga tac gtt ctt gag ggt tgt cct aaa cta caa aag ctt gag atc agg      1756
Arg Tyr Val Leu Glu Gly Cys Pro Lys Leu Gln Lys Leu Glu Ile Arg
520                 525                 530                 535 gac agt ccc ttt gga gat gtt gga ttg cgc tct ggt atg cat cgg tat      1804
Asp Ser Pro Phe Gly Asp Val Gly Leu Arg Ser Gly Met His Arg Tyr
                    540                 545                 550 tcc aat atg agg ttt gtt tgg ttg tcg tca tgt ctc ata tcc cgt gga      1852
Ser Asn Met Arg Phe Val Trp Leu Ser Ser Cys Leu Ile Ser Arg Gly
                555                 560                 565
```

```
ggc tgc agg ggt gtt tct cat gct ctg cct aat gta gtc gtg gaa gta    1900
Gly Cys Arg Gly Val Ser His Ala Leu Pro Asn Val Val Val Glu Val
        570                 575                 580 ttt gga gcc gat ggt gat gat gac gaa gac act gtc act ggg gat tat    1948
Phe Gly Ala Asp Gly Asp Asp Asp Glu Asp Thr Val Thr Gly Asp Tyr
585                 590                 595 gtt gag aca ttg tac ttg tat cga tcc ctt gat ggc cca agg aag gat    1996
Val Glu Thr Leu Tyr Leu Tyr Arg Ser Leu Asp Gly Pro Arg Lys Asp
600                 605                 610                 615 gct cca aag ttt gta aca att tta tga gaaaaacttt ggtgcaaatg          2043
Ala Pro Lys Phe Val Thr Ile Leu
                620 aggccatgat tggggaaaag caaaactagc aagcagaaga taatgtgttt gtaaactgta  2103 agtgcttcag gtacactgca tgatttgttt tgccattttc actcttcttt ggattcgtta  2163 tataccaa gaagagtatt atagctcaaa ggaagacaat gtatgaaaat gaacgaaaga    2223 atcgtctatt attgtttgtg ttgtaataat tgttttttcg caaacattgc cagatttatt  2283 tacagtcatt gcacgattat tatccaaaga attattcgtt atacataaca ttttaagctt  2343 atctattttg ttggcttact agtatttttct tcaccattct tgtcttcctc catcaccaga 2403 tgctctaagg tatcgataaa tgcggtaact ttctccaagc ttttctcatc aagccttggg  2463 acagtatggc ctttgggatg atggacaacc accggattct tgtacgattc tatcagctga  2523 gttccgtaag gtttcagaaa atcagtctct c                                 2554

<210> SEQ ID NO 6
<211> LENGTH: 623
<212> TYPE: PRT
<213> ORGANISM: Arabidopsis thaliana

<400> SEQUENCE: 6

Met Thr Glu Glu Asp Ser Ser Ala Lys Met Ser Glu Asp Val Glu Lys
1               5                   10                  15

Tyr Leu Asn Leu Asn Pro Pro Cys Ser Ser Ser Ser Ser Ser Ser Ser
            20                  25                  30

Ala Ala Thr Phe Thr Asn Lys Ser Arg Asn Phe Lys Ser Ser Pro Pro
        35                  40                  45

Pro Cys Pro Asp His Val Leu Glu Asn Val Leu Glu Asn Val Leu Gln
    50                  55                  60

Phe Leu Thr Ser Arg Cys Asp Arg Asn Ala Val Ser Leu Val Cys Arg
65                  70                  75                  80

Ser Trp Tyr Arg Val Glu Ala Gln Thr Arg Leu Glu Val Phe Ile Gly
                85                  90                  95

Asn Cys Tyr Ser Leu Ser Pro Ala Arg Leu Ile His Arg Phe Lys Arg
            100                 105                 110

Val Arg Ser Leu Val Leu Lys Gly Lys Pro Arg Phe Ala Asp Phe Asn
        115                 120                 125

Leu Met Pro Pro Asn Trp Gly Ala Gln Phe Ser Pro Trp Val Ala Ala
    130                 135                 140

Thr Ala Lys Ala Tyr Pro Trp Leu Glu Lys Val His Leu Lys Arg Met
145                 150                 155                 160

Phe Val Thr Asp Asp Asp Leu Ala Leu Ala Glu Ser Phe Pro Gly
                165                 170                 175

Phe Lys Glu Leu Thr Leu Val Cys Cys Glu Gly Phe Gly Thr Ser Gly
            180                 185                 190

Ile Ala Ile Val Ala Asn Lys Cys Arg Gln Leu Lys Val Leu Asp Leu
```

-continued

```
            195                 200                 205
Met Glu Ser Glu Val Thr Asp Asp Glu Leu Asp Trp Ile Ser Cys Phe
    210                 215                 220
Pro Glu Gly Thr His Leu Glu Ser Leu Ser Phe Asp Cys Val Glu
225                 230                 235                 240
Ser Pro Ile Asn Phe Lys Ala Leu Glu Glu Leu Val Val Arg Ser Pro
                    245                 250                 255
Phe Leu Lys Lys Leu Arg Thr Asn Arg Phe Val Ser Leu Glu Glu Leu
                260                 265                 270
His Arg Leu Met Val Arg Ala Pro Gln Leu Thr Ser Leu Gly Thr Gly
            275                 280                 285
Ser Phe Ser Pro Asp Asn Val Pro Gln Gly Glu Gln Gln Pro Asp Tyr
    290                 295                 300
Ala Ala Ala Phe Arg Ala Cys Lys Ser Ile Val Cys Leu Ser Gly Phe
305                 310                 315                 320
Arg Glu Phe Arg Pro Glu Tyr Leu Leu Ala Ile Ser Ser Val Cys Ala
                    325                 330                 335
Asn Leu Thr Ser Leu Asn Phe Ser Tyr Ala Asn Ile Ser Pro His Met
                340                 345                 350
Leu Lys Pro Ile Ile Ser Asn Cys His Asn Ile Arg Val Phe Trp Ala
            355                 360                 365
Leu Asp Ser Ile Arg Asp Glu Gly Leu Gln Ala Val Ala Ala Thr Cys
    370                 375                 380
Lys Glu Leu Arg Glu Leu Arg Ile Phe Pro Phe Asp Pro Arg Glu Asp
385                 390                 395                 400
Ser Glu Gly Pro Val Ser Gly Val Gly Leu Gln Ala Ile Ser Glu Gly
                    405                 410                 415
Cys Arg Lys Leu Glu Ser Ile Leu Tyr Phe Cys Gln Asn Met Thr Asn
                420                 425                 430
Gly Ala Val Thr Ala Met Ser Glu Asn Cys Pro Gln Leu Thr Val Phe
            435                 440                 445
Arg Leu Cys Ile Met Gly Arg His Arg Pro Asp His Val Thr Gly Lys
    450                 455                 460
Pro Met Asp Asp Gly Phe Gly Ala Ile Val Lys Asn Cys Lys Lys Leu
465                 470                 475                 480
Thr Arg Leu Ala Val Ser Gly Leu Leu Thr Asp Glu Ala Phe Ser Tyr
                    485                 490                 495
Ile Gly Glu Tyr Gly Lys Leu Ile Arg Thr Leu Ser Val Ala Phe Ala
                500                 505                 510
Gly Asn Ser Asp Lys Ala Leu Arg Tyr Val Leu Glu Gly Cys Pro Lys
            515                 520                 525
Leu Gln Lys Leu Glu Ile Arg Asp Ser Pro Phe Gly Asp Val Gly Leu
    530                 535                 540
Arg Ser Gly Met His Arg Tyr Ser Asn Met Arg Phe Val Trp Leu Ser
545                 550                 555                 560
Ser Cys Leu Ile Ser Arg Gly Gly Cys Arg Gly Val Ser His Ala Leu
                    565                 570                 575
Pro Asn Val Val Val Glu Val Phe Gly Ala Asp Gly Asp Asp Asp Glu
                580                 585                 590
Asp Thr Val Thr Gly Asp Tyr Val Glu Thr Leu Tyr Leu Tyr Arg Ser
            595                 600                 605
Leu Asp Gly Pro Arg Lys Asp Ala Pro Lys Phe Val Thr Ile Leu
    610                 615                 620
```

```
<210> SEQ ID NO 7
<211> LENGTH: 1812
<212> TYPE: DNA
<213> ORGANISM: Oryza sativa
<220> FEATURE:
<221> NAME/KEY: CDS
<222> LOCATION: (1)..(1812)

<400> SEQUENCE: 7 atg tcc gag gag gac gac gac cag ccg ccg ccg ctg ccg gcg cag aag       48
Met Ser Glu Glu Asp Asp Asp Gln Pro Pro Pro Leu Pro Ala Gln Lys
1               5                   10                  15 cgg ccg cgc gcg tcg ccg ccg ccg gac cag gtg ctc gac aac gtc ctc       96
Arg Pro Arg Ala Ser Pro Pro Pro Asp Gln Val Leu Asp Asn Val Leu
                20                  25                  30 gag acg gtg ctc cag ttc ctc gac tcg gcg cgg gac cgg tgc gcg gcg      144
Glu Thr Val Leu Gln Phe Leu Asp Ser Ala Arg Asp Arg Cys Ala Ala
            35                  40                  45 tcg ctg gtg tgc cgc tcg tgg agc cgg gcc gag tcc gcc acc cgc gcc      192
Ser Leu Val Cys Arg Ser Trp Ser Arg Ala Glu Ser Ala Thr Arg Ala
        50                  55                  60 tcc gtc gcc gtc cgc aac ctc ctc gcc gcg tcc ccg gcg cgc gtc gcg      240
Ser Val Ala Val Arg Asn Leu Leu Ala Ala Ser Pro Ala Arg Val Ala
65                  70                  75                  80 cga cgc ttc ccg gcc gcg cgg cgc gtc ctc ctc aag ggc cgc ccg cgc      288
Arg Arg Phe Pro Ala Ala Arg Arg Val Leu Leu Lys Gly Arg Pro Arg
                85                  90                  95 ttc gcc gac ttc aac ctc ctc ccg cca ggc tgg gcc ggc gcc gac ttc      336
Phe Ala Asp Phe Asn Leu Leu Pro Pro Gly Trp Ala Gly Ala Asp Phe
                100                 105                 110 cgc ccc tgg gca gcc gcc gtc gcc gcc gcc gcg ttc ccc gcg ctc gcc      384
Arg Pro Trp Ala Ala Ala Val Ala Ala Ala Ala Phe Pro Ala Leu Ala
            115                 120                 125 tcc ctc ttc ctc aag cgc atc acc gtc acc gac gac gac ctg gac ctc      432
Ser Leu Phe Leu Lys Arg Ile Thr Val Thr Asp Asp Asp Leu Asp Leu
        130                 135                 140 gtc tcc cgc tcc ctc ccc gcc tcc ttc cgc gac ctc tcg ctc ctc ctc      480
Val Ser Arg Ser Leu Pro Ala Ser Phe Arg Asp Leu Ser Leu Leu Leu
145                 150                 155                 160 tgc gac ggc ttc tcc tcc gct ggc ctc gca tcc atc gct tcc cat tgc      528
Cys Asp Gly Phe Ser Ser Ala Gly Leu Ala Ser Ile Ala Ser His Cys
                165                 170                 175 agg ggg ctg cga gtg ctc gat gtg gtt gac tgc gag atg aac gac gac      576
Arg Gly Leu Arg Val Leu Asp Val Val Asp Cys Glu Met Asn Asp Asp
                180                 185                 190 gac gac gag gtg gtg gac tgg gtg gcg gcg ttc ccg ccg ggg acg acc      624
Asp Asp Glu Val Val Asp Trp Val Ala Ala Phe Pro Pro Gly Thr Thr
            195                 200                 205 gac ctc gaa tcg ctc tcc ttc gag tgc tac gtc cgg ccg gtg tcc ttc      672
Asp Leu Glu Ser Leu Ser Phe Glu Cys Tyr Val Arg Pro Val Ser Phe
        210                 215                 220 gcc gcg ctc gag gcg ctc gtg gcg cgc tcg ccg cgc ctc acc cgc ctg      720
Ala Ala Leu Glu Ala Leu Val Ala Arg Ser Pro Arg Leu Thr Arg Leu
225                 230                 235                 240 ggc gtc aac gag cac gtg tcg ctg ggg cag ctg cgc cgg ctc atg gcg      768
Gly Val Asn Glu His Val Ser Leu Gly Gln Leu Arg Arg Leu Met Ala
                245                 250                 255 aac acg cct cgc ctg acg cac ctc ggc acc gga gcg ttc cgg ccg ggg      816
Asn Thr Pro Arg Leu Thr His Leu Gly Thr Gly Ala Phe Arg Pro Gly
                260                 265                 270
```

```
gac ggc ccc gag gat gtg ggg ctc gac atc gag cag atg gcg tcc gcg      864
Asp Gly Pro Glu Asp Val Gly Leu Asp Ile Glu Gln Met Ala Ser Ala
        275                 280                 285 ttc gcg tcc gct ggc cgg acg aac acg ctg gtt tcg ctg tct ggc ttc      912
Phe Ala Ser Ala Gly Arg Thr Asn Thr Leu Val Ser Leu Ser Gly Phe
    290                 295                 300 cgc gag ttc gag ccg gag tac ctg ccc acc att gcc gcc gtg tcc ggc      960
Arg Glu Phe Glu Pro Glu Tyr Leu Pro Thr Ile Ala Ala Val Ser Gly
305                 310                 315                 320 aac cta acg aac ctc gac ttc agc tat tgc ccg gtc act ccc gat caa     1008
Asn Leu Thr Asn Leu Asp Phe Ser Tyr Cys Pro Val Thr Pro Asp Gln
                325                 330                 335 ttc ctg ccc ttc atc ggg caa tgc cac aac ctt gag aga cta tat gtg     1056
Phe Leu Pro Phe Ile Gly Gln Cys His Asn Leu Glu Arg Leu Tyr Val
            340                 345                 350 ctt gat tcg gtg cgt gac gag ggg ctc cag gcc acg gcg agg act tgc     1104
Leu Asp Ser Val Arg Asp Glu Gly Leu Gln Ala Thr Ala Arg Thr Cys
        355                 360                 365 aag aag ctc cag gtt ctc cat gtg ctt cca ttg aac gca ctt gag gat     1152
Lys Lys Leu Gln Val Leu His Val Leu Pro Leu Asn Ala Leu Glu Asp
370                 375                 380 gcc gat gag ctg gtg tcg gag gtc ggg ctt act gcc att gct gag ggc     1200
Ala Asp Glu Leu Val Ser Glu Val Gly Leu Thr Ala Ile Ala Glu Gly
385                 390                 395                 400 tgc cga ggg ctc cgt tcg acg ctt tac ttc tgc cag agt atg acc aac     1248
Cys Arg Gly Leu Arg Ser Thr Leu Tyr Phe Cys Gln Ser Met Thr Asn
                405                 410                 415 gct gcg gtg atc gcc att tct caa aat tgc gtg gac ctt aag gta ttc     1296
Ala Ala Val Ile Ala Ile Ser Gln Asn Cys Val Asp Leu Lys Val Phe
            420                 425                 430 cgg tta tgc ata atg gga cgt cac cag cct gac cat gtg act ggg gag     1344
Arg Leu Cys Ile Met Gly Arg His Gln Pro Asp His Val Thr Gly Glu
        435                 440                 445 ccc atg gat gaa ggg ttt ggt gcc att gtt agg aac tgc agc aag ctt     1392
Pro Met Asp Glu Gly Phe Gly Ala Ile Val Arg Asn Cys Ser Lys Leu
450                 455                 460 act agg ctc tcc aca tct gga cac ctg act gat cga gct ttc gag tac     1440
Thr Arg Leu Ser Thr Ser Gly His Leu Thr Asp Arg Ala Phe Glu Tyr
465                 470                 475                 480 att ggc aag tat gcc aag tcg ctc cgg acg ctc tct gtt gcg ttc gct     1488
Ile Gly Lys Tyr Ala Lys Ser Leu Arg Thr Leu Ser Val Ala Phe Ala
                485                 490                 495 gga gac agc aat ctg gcg ttg caa cac atc ctc cag ggg tgc tcg aag     1536
Gly Asp Ser Asn Leu Ala Leu Gln His Ile Leu Gln Gly Cys Ser Lys
            500                 505                 510 ctg gag aag ctg gag ata agg gat tgc cca ttt ggg gat gct ggc ctc     1584
Leu Glu Lys Leu Glu Ile Arg Asp Cys Pro Phe Gly Asp Ala Gly Leu
        515                 520                 525 ctc tcc gga atg cac cat ttc tat aac atg cgg ttc ctc tgg atg tca     1632
Leu Ser Gly Met His His Phe Tyr Asn Met Arg Phe Leu Trp Met Ser
530                 535                 540 ggt tgc aac ctt acg ctg caa ggt tgc aag gag gtc gca cgg agg cta     1680
Gly Cys Asn Leu Thr Leu Gln Gly Cys Lys Glu Val Ala Arg Arg Leu
545                 550                 555                 560 cca aga ttg gtg gtg gag ctg ata aat agc cag cct gag aac gaa agg     1728
Pro Arg Leu Val Val Glu Leu Ile Asn Ser Gln Pro Glu Asn Glu Arg
                565                 570                 575 acc gac agc gtg gac atc tta tac atg tat cgg tcg ctt gaa ggg cca     1776
Thr Asp Ser Val Asp Ile Leu Tyr Met Tyr Arg Ser Leu Glu Gly Pro
```

-continued

```
                580             585             590
aga gag gat gta cca cca ttc gtg aag atc cta taa              1812
Arg Glu Asp Val Pro Pro Phe Val Lys Ile Leu
        595                 600
```

<210> SEQ ID NO 8
<211> LENGTH: 603
<212> TYPE: PRT
<213> ORGANISM: Oryza sativa

<400> SEQUENCE: 8

```
Met Ser Glu Glu Asp Asp Gln Pro Pro Leu Pro Ala Gln Lys
1               5                   10                  15

Arg Pro Arg Ala Ser Pro Pro Asp Gln Val Leu Asp Asn Val Leu
            20                  25                  30

Glu Thr Val Leu Gln Phe Leu Asp Ser Ala Arg Asp Arg Cys Ala Ala
            35                  40                  45

Ser Leu Val Cys Arg Ser Trp Ser Arg Ala Glu Ser Ala Thr Arg Ala
        50                  55                  60

Ser Val Ala Val Arg Asn Leu Leu Ala Ala Ser Pro Ala Arg Val Ala
65                  70                  75                  80

Arg Arg Phe Pro Ala Ala Arg Arg Val Leu Leu Lys Gly Arg Pro Arg
                85                  90                  95

Phe Ala Asp Phe Asn Leu Leu Pro Pro Gly Trp Ala Gly Ala Asp Phe
            100                 105                 110

Arg Pro Trp Ala Ala Ala Val Ala Ala Ala Phe Pro Ala Leu Ala
        115                 120                 125

Ser Leu Phe Leu Lys Arg Ile Thr Val Thr Asp Asp Asp Leu Asp Leu
    130                 135                 140

Val Ser Arg Ser Leu Pro Ala Ser Phe Arg Asp Leu Ser Leu Leu Leu
145                 150                 155                 160

Cys Asp Gly Phe Ser Ser Ala Gly Leu Ala Ser Ile Ala Ser His Cys
                165                 170                 175

Arg Gly Leu Arg Val Leu Asp Val Val Asp Cys Glu Met Asn Asp Asp
            180                 185                 190

Asp Asp Glu Val Val Asp Trp Val Ala Ala Phe Pro Pro Gly Thr Thr
        195                 200                 205

Asp Leu Glu Ser Leu Ser Phe Glu Cys Tyr Val Arg Pro Val Ser Phe
    210                 215                 220

Ala Ala Leu Glu Ala Leu Val Ala Arg Ser Pro Arg Leu Thr Arg Leu
225                 230                 235                 240

Gly Val Asn Glu His Val Ser Leu Gly Gln Leu Arg Arg Leu Met Ala
                245                 250                 255

Asn Thr Pro Arg Leu Thr His Leu Gly Thr Gly Ala Phe Arg Pro Gly
            260                 265                 270

Asp Gly Pro Glu Asp Val Gly Leu Asp Ile Glu Gln Met Ala Ser Ala
        275                 280                 285

Phe Ala Ser Ala Gly Arg Thr Asn Thr Leu Val Ser Leu Ser Gly Phe
    290                 295                 300

Arg Glu Phe Glu Pro Glu Tyr Leu Pro Thr Ile Ala Ala Val Ser Gly
305                 310                 315                 320

Asn Leu Thr Asn Leu Asp Phe Ser Tyr Cys Pro Val Thr Pro Asp Gln
                325                 330                 335

Phe Leu Pro Phe Ile Gly Gln Cys His Asn Leu Glu Arg Leu Tyr Val
            340                 345                 350
```

-continued

Leu Asp Ser Val Arg Asp Glu Gly Leu Gln Ala Thr Ala Arg Thr Cys
        355                 360                 365

Lys Lys Leu Gln Val Leu His Val Leu Pro Leu Asn Ala Leu Glu Asp
    370                 375                 380

Ala Asp Glu Leu Val Ser Glu Val Gly Leu Thr Ala Ile Ala Glu Gly
385                 390                 395                 400

Cys Arg Gly Leu Arg Ser Thr Leu Tyr Phe Cys Gln Ser Met Thr Asn
                405                 410                 415

Ala Ala Val Ile Ala Ile Ser Gln Asn Cys Val Asp Leu Lys Val Phe
            420                 425                 430

Arg Leu Cys Ile Met Gly Arg His Gln Pro Asp His Val Thr Gly Glu
        435                 440                 445

Pro Met Asp Glu Gly Phe Gly Ala Ile Val Arg Asn Cys Ser Lys Leu
    450                 455                 460

Thr Arg Leu Ser Thr Ser Gly His Leu Thr Asp Arg Ala Phe Glu Tyr
465                 470                 475                 480

Ile Gly Lys Tyr Ala Lys Ser Leu Arg Thr Leu Ser Val Ala Phe Ala
                485                 490                 495

Gly Asp Ser Asn Leu Ala Leu Gln His Ile Leu Gln Gly Cys Ser Lys
            500                 505                 510

Leu Glu Lys Leu Glu Ile Arg Asp Cys Pro Phe Gly Asp Ala Gly Leu
        515                 520                 525

Leu Ser Gly Met His His Phe Tyr Asn Met Arg Phe Leu Trp Met Ser
    530                 535                 540

Gly Cys Asn Leu Thr Leu Gln Gly Cys Lys Glu Val Ala Arg Arg Leu
545                 550                 555                 560

Pro Arg Leu Val Val Glu Leu Ile Asn Ser Gln Pro Glu Asn Glu Arg
                565                 570                 575

Thr Asp Ser Val Asp Ile Leu Tyr Met Tyr Arg Ser Leu Glu Gly Pro
            580                 585                 590

Arg Glu Asp Val Pro Pro Phe Val Lys Ile Leu
        595                 600

<210> SEQ ID NO 9
<211> LENGTH: 2581
<212> TYPE: DNA
<213> ORGANISM: Oryza sativa
<220> FEATURE:
<221> NAME/KEY: CDS
<222> LOCATION: (87)..(2000)

<400> SEQUENCE: 9
gcacttcccc ctcctgctcc tcctcctcgc cgatccccca atccctaacc ctagcctcca     60
cctcctcctc ctcctcatcc tccggg atg cgc gat gcg ggg gag ggg tcg gac    113
              Met Arg Asp Ala Gly Glu Gly Ser Asp
                1               5 tcg ccg ccg tcg gag atg tcg gag gat ggg tca gga ggg agc ggg gac    161
Ser Pro Pro Ser Glu Met Ser Glu Asp Gly Ser Gly Gly Ser Gly Asp
10                  15                  20                  25 ggg gac ggg gac ggg gac ggg gga ggg gga ggc ggg gac agg tgg atg    209
Gly Asp Gly Asp Gly Asp Gly Gly Gly Gly Gly Gly Asp Arg Trp Met
                30                  35                  40 ccg gat ctg agg gga ggg aac ggc ggc ggc gga gga ggc gga ggg        257
Pro Asp Leu Arg Gly Gly Asn Gly Gly Gly Gly Gly Gly Gly Gly
            45                  50                  55 gga ggg agg tgg gcg ccg ccg gac cag gtg ctg gag aac gtg ctg gag    305

```
Gly Gly Arg Trp Ala Pro Pro Asp Gln Val Leu Glu Asn Val Leu Glu
         60                  65                  70 agc gtg ctg gag ttc ctg acg gcg gcg cgg gac cgg aac gcg gcg tcg    353
Ser Val Leu Glu Phe Leu Thr Ala Ala Arg Asp Arg Asn Ala Ala Ser
 75                  80                  85 ctg gtg tgc cgg tcg tgg tac cgc gcc gag gcg cag acg cgg cgg gag    401
Leu Val Cys Arg Ser Trp Tyr Arg Ala Glu Ala Gln Thr Arg Arg Glu
 90                  95                 100                 105 ctg ttc atc ggc aac tgc tac gcg gtg tcg ccg cgc cgc gcc gtg gag    449
Leu Phe Ile Gly Asn Cys Tyr Ala Val Ser Pro Arg Arg Ala Val Glu
                    110                 115                 120 cgg ttc gga ggg gtg cgc gcc gtg gtg ctc aag ggg aag ccg cgg ttc    497
Arg Phe Gly Gly Val Arg Ala Val Val Leu Lys Gly Lys Pro Arg Phe
                125                 130                 135 gcg gac ttc agc ctc gtg ccc tac ggc tgg ggc gcc tac gtc tcc ccc    545
Ala Asp Phe Ser Leu Val Pro Tyr Gly Trp Gly Ala Tyr Val Ser Pro
        140                 145                 150 tgg gtc gcc gcg ctc ggc ccc gcc tac ccg cac ctc gag cgc atc tgc    593
Trp Val Ala Ala Leu Gly Pro Ala Tyr Pro His Leu Glu Arg Ile Cys
155                 160                 165 ctc aag cgc atg acc gtc tcc aac gac gac ctc gcg ctc atc gcc aag    641
Leu Lys Arg Met Thr Val Ser Asn Asp Asp Leu Ala Leu Ile Ala Lys
170                 175                 180                 185 tca ttc ccg ctg ttc aag gag ctg tcg ctg gtg tgc tgc gat ggg ttc    689
Ser Phe Pro Leu Phe Lys Glu Leu Ser Leu Val Cys Cys Asp Gly Phe
                    190                 195                 200 agc acg cta ggc ctc gcc gcc atc gcc gag cgg tgc cgg cat ctc cgt    737
Ser Thr Leu Gly Leu Ala Ala Ile Ala Glu Arg Cys Arg His Leu Arg
                205                 210                 215 gtg ctg gat ctg att gaa gac tat att gac gag gag gag gat gag cta    785
Val Leu Asp Leu Ile Glu Asp Tyr Ile Asp Glu Glu Glu Asp Glu Leu
        220                 225                 230 gtg gat tgg atc tcc aag ttc ccg gag tcc aac acg tcg ctg gag tca    833
Val Asp Trp Ile Ser Lys Phe Pro Glu Ser Asn Thr Ser Leu Glu Ser
235                 240                 245 ctt gtg ttt gat tgt gtt agt gtc cca ttc aac ttt gag gcc ctg gag    881
Leu Val Phe Asp Cys Val Ser Val Pro Phe Asn Phe Glu Ala Leu Glu
250                 255                 260                 265 gcg ctt gtt gca cgc tca cca gct atg cgc cgg ttg cga atg aat cac    929
Ala Leu Val Ala Arg Ser Pro Ala Met Arg Arg Leu Arg Met Asn His
                    270                 275                 280 cat gtg aca gta gag caa ttg cgc cgt cta atg gca agg gct ccc cag    977
His Val Thr Val Glu Gln Leu Arg Arg Leu Met Ala Arg Ala Pro Gln
                285                 290                 295 ctc aca cac ctt ggt act ggt gca ttc cgt tct gag cca ggc cct ggt   1025
Leu Thr His Leu Gly Thr Gly Ala Phe Arg Ser Glu Pro Gly Pro Gly
        300                 305                 310 ggt gct ctg tct gtt act gag ctt gct aca tct ttt gcg gca tct agg   1073
Gly Ala Leu Ser Val Thr Glu Leu Ala Thr Ser Phe Ala Ala Ser Arg
315                 320                 325 tct ctg att tgt ttg tca ggt ttc cgg gat gtc aat cca gaa tac ctc   1121
Ser Leu Ile Cys Leu Ser Gly Phe Arg Asp Val Asn Pro Glu Tyr Leu
330                 335                 340                 345 cca gca atc cac cca gtc tgc gct aat ctc act tcc ctt aat ttt agc   1169
Pro Ala Ile His Pro Val Cys Ala Asn Leu Thr Ser Leu Asn Phe Ser
                    350                 355                 360 ttt gca aac cta act gct gag gag ctc aca ccg att att cgc aac tgc   1217
Phe Ala Asn Leu Thr Ala Glu Glu Leu Thr Pro Ile Ile Arg Asn Cys
                365                 370                 375
```

```
gtc cgt ctt cgc act ttc tgg gtt cta gat aca gtg ggt gat gaa ggc      1265
Val Arg Leu Arg Thr Phe Trp Val Leu Asp Thr Val Gly Asp Glu Gly
        380                 385                 390 ctt cgg gct gtg gct gag aca tgc tca gat ctt cgt gag ctg cga gtt      1313
Leu Arg Ala Val Ala Glu Thr Cys Ser Asp Leu Arg Glu Leu Arg Val
    395                 400                 405 ttt cct ttc gat gcc act gag gat tct gag gga tcg gtt tca gat gtt      1361
Phe Pro Phe Asp Ala Thr Glu Asp Ser Glu Gly Ser Val Ser Asp Val
410                 415                 420                 425 ggt ctt cag gca atc tcg gaa ggg tgc cgg aag ctt gaa tca att ctc      1409
Gly Leu Gln Ala Ile Ser Glu Gly Cys Arg Lys Leu Glu Ser Ile Leu
                430                 435                 440 tac ttt tgc cag cgc atg aca aat gca gca gta att gct atg tcc aag      1457
Tyr Phe Cys Gln Arg Met Thr Asn Ala Ala Val Ile Ala Met Ser Lys
        445                 450                 455 aac tgt tct gac ctg gta aca ttc cgt ctt tgt att atg ggg cga cac      1505
Asn Cys Ser Asp Leu Val Thr Phe Arg Leu Cys Ile Met Gly Arg His
    460                 465                 470 cgc cct gat cgg atc act ggg gag ccc atg gat gat ggt ttt ggg gca      1553
Arg Pro Asp Arg Ile Thr Gly Glu Pro Met Asp Asp Gly Phe Gly Ala
475                 480                 485 att gtg atg aac tgc aag aag ctc act aga ctt tca gtc tct ggt ctg      1601
Ile Val Met Asn Cys Lys Lys Leu Thr Arg Leu Ser Val Ser Gly Leu
490                 495                 500                 505 ctc act gat aag gcg ttt gca tac att gga aaa tat ggg aaa cta ata      1649
Leu Thr Asp Lys Ala Phe Ala Tyr Ile Gly Lys Tyr Gly Lys Leu Ile
                510                 515                 520 aag aca ctg tct gtt gcc ttc gct gga aat agt gac atg tct ctc caa      1697
Lys Thr Leu Ser Val Ala Phe Ala Gly Asn Ser Asp Met Ser Leu Gln
        525                 530                 535 tct gtg ttt gaa gga tgc act agg ttg caa aag ctt gag gtc aga gat      1745
Ser Val Phe Glu Gly Cys Thr Arg Leu Gln Lys Leu Glu Val Arg Asp
    540                 545                 550 agt cct ttt agt gat aag gga ttg ctc tct ggc ctg agc tat ttt tac      1793
Ser Pro Phe Ser Asp Lys Gly Leu Leu Ser Gly Leu Ser Tyr Phe Tyr
555                 560                 565 aac atg agg ttc tta tgg atg aat tca tgc agg cta acc atg agg ggt      1841
Asn Met Arg Phe Leu Trp Met Asn Ser Cys Arg Leu Thr Met Arg Gly
570                 575                 580                 585 tgt aga gat gta gct cag caa atg cct gac ttg gtg gtt gaa gtg atg      1889
Cys Arg Asp Val Ala Gln Gln Met Pro Asp Leu Val Val Glu Val Met
                590                 595                 600 aag gat cat ctt gat gat gaa ggg gag atg gag act gtt gat aaa ctg      1937
Lys Asp His Leu Asp Asp Glu Gly Glu Met Glu Thr Val Asp Lys Leu
        605                 610                 615 tac ttg tat cga tca ctg gca gga gca agg aat gat gca cct tca ttt      1985
Tyr Leu Tyr Arg Ser Leu Ala Gly Ala Arg Asn Asp Ala Pro Ser Phe
    620                 625                 630 gtc aac atc ttg tag tactgctaca ggaagaagtt tgttgtactc acaaaacaag      2040
Val Asn Ile Leu
635 tttgttctat taaaccttat cattgctatt gtattcctga accctgatca gtctatcaga   2100 atcagacaca gaagcttccc gcagatgatt ttcaaatgtc gtgggaact tcgattatgc    2160 ggatctccaa attgttcttt tctttgctga caatgaggca tatgaggctc ttcttgatgt   2220 atgtattgtt gctgaggaga agttcgtcga gtgagctacc tgatgcctga tgggatcct    2280 tcttttcctt gctgtgactc gactgatgcc taccattta ctgttagatg aagagtagga    2340 actgattcca atcagcaggg ttagattagc catctttga tctgctcaga cgaaggaatg    2400
```

```
gcaatgctcc aatattccat catccgttgc cttatgtttt agatctcaaa actcaactat    2460
gataattgtt tccttttca ttttttggg gttctctctt gagttatttt tgtagtccat    2520 tttaccccccc ttttacttgg tcacgtcgct gttatgaatc aagaagctat tggaggaatt    2580
g                                                                    2581
```

<210> SEQ ID NO 10
<211> LENGTH: 637
<212> TYPE: PRT
<213> ORGANISM: Oryza sativa

<400> SEQUENCE: 10

```
Met Arg Asp Ala Gly Glu Gly Ser Asp Ser Pro Pro Ser Glu Met Ser
1               5                   10                  15

Glu Asp Gly Ser Gly Gly Ser Gly Asp Gly Asp Gly Asp Gly Asp Gly
                20                  25                  30

Gly Gly Gly Gly Gly Asp Arg Trp Met Pro Asp Leu Arg Gly Gly Asn
            35                  40                  45

Gly Gly Gly Gly Gly Gly Gly Gly Gly Arg Trp Ala Pro Pro
        50                  55                  60

Asp Gln Val Leu Glu Asn Val Leu Glu Ser Val Leu Glu Phe Leu Thr
65                  70                  75                  80

Ala Ala Arg Asp Arg Asn Ala Ala Ser Leu Val Cys Arg Ser Trp Tyr
                85                  90                  95

Arg Ala Glu Ala Gln Thr Arg Arg Glu Leu Phe Ile Gly Asn Cys Tyr
            100                 105                 110

Ala Val Ser Pro Arg Arg Ala Val Glu Arg Phe Gly Gly Val Arg Ala
        115                 120                 125

Val Val Leu Lys Gly Lys Pro Arg Phe Ala Asp Phe Ser Leu Val Pro
130                 135                 140

Tyr Gly Trp Gly Ala Tyr Val Ser Pro Trp Val Ala Ala Leu Gly Pro
145                 150                 155                 160

Ala Tyr Pro His Leu Glu Arg Ile Cys Leu Lys Arg Met Thr Val Ser
                165                 170                 175

Asn Asp Asp Leu Ala Leu Ile Ala Lys Ser Phe Pro Leu Phe Lys Glu
            180                 185                 190

Leu Ser Leu Val Cys Cys Asp Gly Phe Ser Thr Leu Gly Leu Ala Ala
        195                 200                 205

Ile Ala Glu Arg Cys Arg His Leu Arg Val Leu Asp Leu Ile Glu Asp
210                 215                 220

Tyr Ile Asp Glu Glu Glu Asp Glu Leu Val Asp Trp Ile Ser Lys Phe
225                 230                 235                 240

Pro Glu Ser Asn Thr Ser Leu Glu Ser Leu Val Phe Asp Cys Val Ser
                245                 250                 255

Val Pro Phe Asn Phe Glu Ala Leu Glu Ala Leu Val Ala Arg Ser Pro
            260                 265                 270

Ala Met Arg Arg Leu Arg Met Asn His His Val Thr Val Glu Gln Leu
        275                 280                 285

Arg Arg Leu Met Ala Arg Ala Pro Gln Leu Thr His Leu Gly Thr Gly
290                 295                 300

Ala Phe Arg Ser Glu Pro Gly Pro Gly Gly Ala Leu Ser Val Thr Glu
305                 310                 315                 320

Leu Ala Thr Ser Phe Ala Ala Ser Arg Ser Leu Ile Cys Leu Ser Gly
                325                 330                 335
```

Phe Arg Asp Val Asn Pro Glu Tyr Leu Pro Ala Ile His Pro Val Cys
                340                 345                 350

Ala Asn Leu Thr Ser Leu Asn Phe Ser Phe Ala Asn Leu Thr Ala Glu
            355                 360                 365

Glu Leu Thr Pro Ile Ile Arg Asn Cys Val Arg Leu Arg Thr Phe Trp
        370                 375                 380

Val Leu Asp Thr Val Gly Asp Glu Gly Leu Arg Ala Val Ala Glu Thr
385                 390                 395                 400

Cys Ser Asp Leu Arg Glu Leu Arg Val Phe Pro Phe Asp Ala Thr Glu
                405                 410                 415

Asp Ser Glu Gly Ser Val Ser Asp Val Gly Leu Gln Ala Ile Ser Glu
            420                 425                 430

Gly Cys Arg Lys Leu Glu Ser Ile Leu Tyr Phe Cys Gln Arg Met Thr
        435                 440                 445

Asn Ala Ala Val Ile Ala Met Ser Lys Asn Cys Ser Asp Leu Val Thr
450                 455                 460

Phe Arg Leu Cys Ile Met Gly Arg His Arg Pro Asp Arg Ile Thr Gly
465                 470                 475                 480

Glu Pro Met Asp Asp Gly Phe Gly Ala Ile Val Met Asn Cys Lys Lys
                485                 490                 495

Leu Thr Arg Leu Ser Val Ser Gly Leu Leu Thr Asp Lys Ala Phe Ala
            500                 505                 510

Tyr Ile Gly Lys Tyr Gly Lys Leu Ile Lys Thr Leu Ser Val Ala Phe
        515                 520                 525

Ala Gly Asn Ser Asp Met Ser Leu Gln Ser Val Phe Glu Gly Cys Thr
530                 535                 540

Arg Leu Gln Lys Leu Glu Val Arg Asp Ser Pro Phe Ser Asp Lys Gly
545                 550                 555                 560

Leu Leu Ser Gly Leu Ser Tyr Phe Tyr Asn Met Arg Phe Leu Trp Met
                565                 570                 575

Asn Ser Cys Arg Leu Thr Met Arg Gly Cys Arg Asp Val Ala Gln Gln
            580                 585                 590

Met Pro Asp Leu Val Val Glu Val Met Lys Asp His Leu Asp Asp Glu
        595                 600                 605

Gly Glu Met Glu Thr Val Asp Lys Leu Tyr Leu Tyr Arg Ser Leu Ala
        610                 615                 620

Gly Ala Arg Asn Asp Ala Pro Ser Phe Val Asn Ile Leu
625                 630                 635

<210> SEQ ID NO 11
<211> LENGTH: 2646
<212> TYPE: DNA
<213> ORGANISM: Populus
<220> FEATURE:
<221> NAME/KEY: CDS
<222> LOCATION: (345)..(2252)

<400> SEQUENCE: 11
gccggccgcc atggatcatc ctaatacgac tcactatagg gctcgagcgg ccgcccgggc      60
aggtaggcag catggagaat cccgatgctt tactcagtct atcagacatc acagcctact     120
actcttcttc tcaccaatta tactaagata aactaagcaa ttcttcgctt cctcgcctct     180
ctcttcaatc cccatcaaac cctctctctc tctatcgaaa cccataatcc cagacccaac     240
tgacaaaaag tcactcaaaa ctttccccga tcgaaaacct tcaatatata tatatgtata     300

-continued

```
tatactttta agattcctgt tttttttct cccttcaaat ttgt atg atc acc aac         356
                                                Met Ile Thr Asn
                                                  1 aaa aag cct aga tca tca gaa acc gac tct aat tac atg aga gac gat         404
Lys Lys Pro Arg Ser Ser Glu Thr Asp Ser Asn Tyr Met Arg Asp Asp
  5              10                  15                  20 cga act gaa atg tcc gaa gac gac gac aga tct cct ccc tcc aac tca         452
Arg Thr Glu Met Ser Glu Asp Asp Asp Arg Ser Pro Pro Ser Asn Ser
             25                  30                  35 atc acc cat gat tct agc cca acc cgg acc tgc acc ccc ggg ccc ggg         500
Ile Thr His Asp Ser Ser Pro Thr Arg Thr Cys Thr Pro Gly Pro Gly
         40                  45                  50 tcg ggt tca tct tca gtc ccc gaa tac tta gct ccg tac ccg gac caa         548
Ser Gly Ser Ser Ser Val Pro Glu Tyr Leu Ala Pro Tyr Pro Asp Gln
     55                  60                  65 gtc ctt gaa aac gtc tta gaa aac gtt ctc tgg ttc cta acc tca cgt         596
Val Leu Glu Asn Val Leu Glu Asn Val Leu Trp Phe Leu Thr Ser Arg
 70                  75                  80 aag gac cga aac gct gcg tca ttg gtt tgt agg tca tgg tac cgg gtc         644
Lys Asp Arg Asn Ala Ala Ser Leu Val Cys Arg Ser Trp Tyr Arg Val
 85                  90                  95                 100 gag gct ctg acc cga tcc gat ttg ttc atc ggt aac tgc tac gcg gtg         692
Glu Ala Leu Thr Arg Ser Asp Leu Phe Ile Gly Asn Cys Tyr Ala Val
                105                 110                 115 tct cca aag cga gcc atg tcg cgg ttt acc cga atc agg tcg gtg acg         740
Ser Pro Lys Arg Ala Met Ser Arg Phe Thr Arg Ile Arg Ser Val Thr
                120                 125                 130 ctg aaa ggg aag cca agg ttt gct gat ttt aac ctg atg ccg cct tat         788
Leu Lys Gly Lys Pro Arg Phe Ala Asp Phe Asn Leu Met Pro Pro Tyr
            135                 140                 145 tgg gga gcc cac ttc gcg cct tgg gtc tct gct atg gca atg act tac         836
Trp Gly Ala His Phe Ala Pro Trp Val Ser Ala Met Ala Met Thr Tyr
        150                 155                 160 cct tgg tta gag aag gtt cat ttg aag agg atg tca gtg acg gat gat         884
Pro Trp Leu Glu Lys Val His Leu Lys Arg Met Ser Val Thr Asp Asp
165                 170                 175                 180 gat ctg gct ttg ctt gcg gag tcg ttt tcg gga ttc aaa gag ctc gtg         932
Asp Leu Ala Leu Leu Ala Glu Ser Phe Ser Gly Phe Lys Glu Leu Val
                185                 190                 195 ctt gtt tgt tgt gag ggg ttc ggt act agt gga ctt gct att gtc gtt         980
Leu Val Cys Cys Glu Gly Phe Gly Thr Ser Gly Leu Ala Ile Val Val
                200                 205                 210 agc agg tgc agg caa ctc aaa gtg ctt gat ctg att gaa tca gat gta        1028
Ser Arg Cys Arg Gln Leu Lys Val Leu Asp Leu Ile Glu Ser Asp Val
            215                 220                 225 tca gat gat gaa gtg gat tgg att tcg tgt ttt cca gat acc gaa aca        1076
Ser Asp Asp Glu Val Asp Trp Ile Ser Cys Phe Pro Asp Thr Glu Thr
        230                 235                 240 tgc ctc gaa tcc ctg att ttt gat tgt gta gat tgc ccc att gat ttt        1124
Cys Leu Glu Ser Leu Ile Phe Asp Cys Val Asp Cys Pro Ile Asp Phe
245                 250                 255                 260 gat gaa ctg gag agg ctg gtg gct agg tct cca tca ctt aag aaa ctt        1172
Asp Glu Leu Glu Arg Leu Val Ala Arg Ser Pro Ser Leu Lys Lys Leu
                265                 270                 275 agg ctg aac cga tat gtt tcg att gga caa ctt tac cgt cta atg att        1220
Arg Leu Asn Arg Tyr Val Ser Ile Gly Gln Leu Tyr Arg Leu Met Ile
                280                 285                 290 cga gct cca cac ctc aca cat ctt ggg aca ggc tct ttt agc cca tca        1268
Arg Ala Pro His Leu Thr His Leu Gly Thr Gly Ser Phe Ser Pro Ser
            295                 300                 305
```

```
gag gat gta tct cag gtt gaa cag gga cca gat tat gct tct gca ttt      1316
Glu Asp Val Ser Gln Val Glu Gln Gly Pro Asp Tyr Ala Ser Ala Phe
    310                 315                 320 gct gct tgc aaa tcc tta gtt tgc cta tct gga ttc agg gaa atc att      1364
Ala Ala Cys Lys Ser Leu Val Cys Leu Ser Gly Phe Arg Glu Ile Ile
325                 330                 335                 340 cca gat tac ttg cct gca ata aac cct gta tgt gcc aat ctc act tca      1412
Pro Asp Tyr Leu Pro Ala Ile Asn Pro Val Cys Ala Asn Leu Thr Ser
                345                 350                 355 ctg aac ttt agt ttt gca gat gtt agt gca gaa cag ctc aaa cca atc      1460
Leu Asn Phe Ser Phe Ala Asp Val Ser Ala Glu Gln Leu Lys Pro Ile
            360                 365                 370 ata agc aat tgc cac aag ctt cag att ttc tgg gtt ctt gat tca ata      1508
Ile Ser Asn Cys His Lys Leu Gln Ile Phe Trp Val Leu Asp Ser Ile
        375                 380                 385 tgc gat gaa gga ctg cag gct gtg gct gca aca tgc aag gag cta cga      1556
Cys Asp Glu Gly Leu Gln Ala Val Ala Ala Thr Cys Lys Glu Leu Arg
    390                 395                 400 gag ctt cgg gtc ttc cct gtt gac cct agg gag gac att gag ggc cct      1604
Glu Leu Arg Val Phe Pro Val Asp Pro Arg Glu Asp Ile Glu Gly Pro
405                 410                 415                 420 gtt tct gaa gtg ggc ctc caa gca att tca gag ggt tgc agg aag ctt      1652
Val Ser Glu Val Gly Leu Gln Ala Ile Ser Glu Gly Cys Arg Lys Leu
                425                 430                 435 caa tct att ttg tat ttt tgc cat cgg atg aca aat gct gct gtt gta      1700
Gln Ser Ile Leu Tyr Phe Cys His Arg Met Thr Asn Ala Ala Val Val
            440                 445                 450 gct atg tca aag aac tgc cca gac ctt gtg gtc ttc cgt ctc tgc ata      1748
Ala Met Ser Lys Asn Cys Pro Asp Leu Val Val Phe Arg Leu Cys Ile
        455                 460                 465 atg ggg cgt cac cag cct gat cat gtc act gga gaa cct atg gat gaa      1796
Met Gly Arg His Gln Pro Asp His Val Thr Gly Glu Pro Met Asp Glu
    470                 475                 480 gga ttt gga gcc att gtc aag aat tgc aag aag ctc act cga ctc gcg      1844
Gly Phe Gly Ala Ile Val Lys Asn Cys Lys Lys Leu Thr Arg Leu Ala
485                 490                 495                 500 gta tct ggt tta ttg act gat aga gct ttt gct tat att gga aaa tat      1892
Val Ser Gly Leu Leu Thr Asp Arg Ala Phe Ala Tyr Ile Gly Lys Tyr
                505                 510                 515 ggg aaa att gta agg acc cta tcg gtt gct ttt gct gga gat agt gac      1940
Gly Lys Ile Val Arg Thr Leu Ser Val Ala Phe Ala Gly Asp Ser Asp
            520                 525                 530 atg ggg ctg aaa tat gtg ctt gag ggt tgt ccc aga ttg cag aag ctt      1988
Met Gly Leu Lys Tyr Val Leu Glu Gly Cys Pro Arg Leu Gln Lys Leu
        535                 540                 545 gag att aga gac agt cca ttc ggg gat gca gct cta ctt tct ggt ctg      2036
Glu Ile Arg Asp Ser Pro Phe Gly Asp Ala Ala Leu Leu Ser Gly Leu
    550                 555                 560 cac cac tat tac aat atg aga ttc ctt tgg atg tct gct tgc aag ttg      2084
His His Tyr Tyr Asn Met Arg Phe Leu Trp Met Ser Ala Cys Lys Leu
565                 570                 575                 580 tct cgc caa ggc tgc caa cag att act caa gcg ttg cct cgg ctg gtg      2132
Ser Arg Gln Gly Cys Gln Gln Ile Thr Gln Ala Leu Pro Arg Leu Val
                585                 590                 595 gtg gaa gtg att aag cat gac gat aat gtg gac atg gat gag tat gtt      2180
Val Glu Val Ile Lys His Asp Asp Asn Val Asp Met Asp Glu Tyr Val
            600                 605                 610 gat acg ttg tat atg tac cgg tct ctt gaa ggg cca aga gat gat gcg      2228
Asp Thr Leu Tyr Met Tyr Arg Ser Leu Glu Gly Pro Arg Asp Asp Ala
```

-continued

```
                615                 620                 625
cca cga ttt gtt tcc atc ttg tag ggcatttgtg ctacaagaag ttgcatcagc    2282
Pro Arg Phe Val Ser Ile Leu
        630             635 tgttctgatg gtggttatgg gcatcttttc ctggaaatta aatcttgcag gtaccttta    2342 catagcccgc aagaaagtca tggtgatcct tgcaagagaa agttgagtaa aacttcaggc   2402
cttgtgctgt gttgttgcaa atggcattca atccagaagc cctataattt aagaggacag   2462
acatcgaggg ggctgatgtg gagttggata tctctgcaag gtattggacc acccattgga   2522
tcttgttgta ttgatatgct tcaaaatttt atgtttcttt ttttcttttc gaactcattt   2582
gatcataaat gagaaggctg ctccggagga aagggatgga tgggccttga ggcgcataaa   2642
aaaa                                                               2646
```

<210> SEQ ID NO 12
<211> LENGTH: 635
<212> TYPE: PRT
<213> ORGANISM: Populus

<400> SEQUENCE: 12

```
Met Ile Thr Asn Lys Lys Pro Arg Ser Ser Glu Thr Asp Ser Asn Tyr
1               5                   10                  15

Met Arg Asp Asp Arg Thr Glu Met Ser Glu Asp Asp Arg Ser Pro
            20                  25                  30

Pro Ser Asn Ser Ile Thr His Asp Ser Ser Pro Thr Arg Thr Cys Thr
            35                  40                  45

Pro Gly Pro Gly Ser Gly Ser Ser Val Pro Glu Tyr Leu Ala Pro
        50                  55                  60

Tyr Pro Asp Gln Val Leu Glu Asn Val Leu Glu Asn Val Leu Trp Phe
65                  70                  75                  80

Leu Thr Ser Arg Lys Asp Arg Asn Ala Ala Ser Leu Val Cys Arg Ser
                85                  90                  95

Trp Tyr Arg Val Glu Ala Leu Thr Arg Ser Asp Leu Phe Ile Gly Asn
            100                 105                 110

Cys Tyr Ala Val Ser Pro Lys Arg Ala Met Ser Arg Phe Thr Arg Ile
        115                 120                 125

Arg Ser Val Thr Leu Lys Gly Lys Pro Arg Phe Ala Asp Phe Asn Leu
    130                 135                 140

Met Pro Pro Tyr Trp Gly Ala His Phe Ala Pro Trp Val Ser Ala Met
145                 150                 155                 160

Ala Met Thr Tyr Pro Trp Leu Glu Lys Val His Leu Lys Arg Met Ser
                165                 170                 175

Val Thr Asp Asp Asp Leu Ala Leu Leu Ala Glu Ser Phe Ser Gly Phe
            180                 185                 190

Lys Glu Leu Val Leu Val Cys Cys Glu Gly Phe Gly Thr Ser Gly Leu
        195                 200                 205

Ala Ile Val Val Ser Arg Cys Arg Gln Leu Lys Val Leu Asp Leu Ile
    210                 215                 220

Glu Ser Asp Val Ser Asp Asp Glu Val Asp Trp Ile Ser Cys Phe Pro
225                 230                 235                 240

Asp Thr Glu Thr Cys Leu Glu Ser Leu Ile Phe Asp Cys Val Asp Cys
                245                 250                 255

Pro Ile Asp Phe Asp Glu Leu Glu Arg Leu Val Ala Arg Ser Pro Ser
            260                 265                 270
```

-continued

```
Leu Lys Lys Leu Arg Leu Asn Arg Tyr Val Ser Ile Gly Gln Leu Tyr
    275                 280                 285

Arg Leu Met Ile Arg Ala Pro His Leu Thr His Leu Gly Thr Gly Ser
290                 295                 300

Phe Ser Pro Ser Glu Asp Val Ser Gln Val Glu Gln Gly Pro Asp Tyr
305                 310                 315                 320

Ala Ser Ala Phe Ala Ala Cys Lys Ser Leu Val Cys Leu Ser Gly Phe
                325                 330                 335

Arg Glu Ile Ile Pro Asp Tyr Leu Pro Ala Ile Asn Pro Val Cys Ala
            340                 345                 350

Asn Leu Thr Ser Leu Asn Phe Ser Phe Ala Asp Val Ser Ala Glu Gln
        355                 360                 365

Leu Lys Pro Ile Ile Ser Asn Cys His Lys Leu Gln Ile Phe Trp Val
    370                 375                 380

Leu Asp Ser Ile Cys Asp Glu Gly Leu Gln Ala Val Ala Ala Thr Cys
385                 390                 395                 400

Lys Glu Leu Arg Glu Leu Arg Val Phe Pro Val Asp Pro Arg Glu Asp
                405                 410                 415

Ile Glu Gly Pro Val Ser Glu Val Gly Leu Gln Ala Ile Ser Glu Gly
            420                 425                 430

Cys Arg Lys Leu Gln Ser Ile Leu Tyr Phe Cys His Arg Met Thr Asn
        435                 440                 445

Ala Ala Val Val Ala Met Ser Lys Asn Cys Pro Asp Leu Val Val Phe
    450                 455                 460

Arg Leu Cys Ile Met Gly Arg His Gln Pro Asp His Val Thr Gly Glu
465                 470                 475                 480

Pro Met Asp Glu Gly Phe Gly Ala Ile Val Lys Asn Cys Lys Lys Leu
                485                 490                 495

Thr Arg Leu Ala Val Ser Gly Leu Leu Thr Asp Arg Ala Phe Ala Tyr
            500                 505                 510

Ile Gly Lys Tyr Gly Lys Ile Val Arg Thr Leu Ser Val Ala Phe Ala
        515                 520                 525

Gly Asp Ser Asp Met Gly Leu Lys Tyr Val Leu Glu Gly Cys Pro Arg
    530                 535                 540

Leu Gln Lys Leu Glu Ile Arg Asp Ser Pro Phe Gly Asp Ala Ala Leu
545                 550                 555                 560

Leu Ser Gly Leu His His Tyr Tyr Asn Met Arg Phe Leu Trp Met Ser
                565                 570                 575

Ala Cys Lys Leu Ser Arg Gln Gly Cys Gln Gln Ile Thr Gln Ala Leu
            580                 585                 590

Pro Arg Leu Val Val Glu Val Ile Lys His Asp Asp Asn Val Asp Met
        595                 600                 605

Asp Glu Tyr Val Asp Thr Leu Tyr Met Tyr Arg Ser Leu Glu Gly Pro
    610                 615                 620

Arg Asp Asp Ala Pro Arg Phe Val Ser Ile Leu
625                 630                 635

<210> SEQ ID NO 13
<211> LENGTH: 10
```

```
<212> TYPE: PRT
<213> ORGANISM: Artificial Sequence
<220> FEATURE:
<223> OTHER INFORMATION: Epitope -- synthetic

<400> SEQUENCE: 13

Glu Gln Lys Leu Ile Ser Glu Glu Asp Leu
1               5                   10
```